United States Patent
Beemiller et al.

(10) Patent No.: US 11,993,766 B2
(45) Date of Patent: May 28, 2024

(54) FUNCTIONALIZED WELL PLATE, METHODS OF PREPARATION AND USE THEREOF

(71) Applicant: BRUKER CELLULAR ANALYSIS, INC., Emeryville, CA (US)

(72) Inventors: Peter J. Beemiller, Emeryville, CA (US); Alexander J. Mastroianni, Alameda, CA (US); Randall D. Lowe, Jr., Emeryville, CA (US); Yelena Bronevetsky, Alameda, CA (US)

(73) Assignee: BRUKER CELLULAR ANALYSIS, INC., Emeryville, CA (US)

( * ) Notice: Subject to any disclaimer, the term of this patent is extended or adjusted under 35 U.S.C. 154(b) by 1000 days.

(21) Appl. No.: 16/578,026

(22) Filed: Sep. 20, 2019

(65) Prior Publication Data

US 2020/0123491 A1   Apr. 23, 2020

Related U.S. Application Data

(60) Provisional application No. 62/893,712, filed on Aug. 29, 2019, provisional application No. 62/734,924, filed on Sep. 21, 2018.

(51) Int. Cl.
| | |
|---|---|
| C12M 1/12 | (2006.01) |
| C07K 17/02 | (2006.01) |
| C12M 1/00 | (2006.01) |
| C12M 1/32 | (2006.01) |
| C12N 5/0783 | (2010.01) |

(52) U.S. Cl.
CPC .............. *C12M 25/06* (2013.01); *C07K 17/02* (2013.01); *C12M 23/12* (2013.01); *C12M 23/20* (2013.01); *C12N 5/0636* (2013.01)

(58) Field of Classification Search
CPC ...... C12M 25/06; C12M 23/12; C12M 23/20; C12N 5/0636
See application file for complete search history.

(56) References Cited

U.S. PATENT DOCUMENTS

| | | |
|---|---|---|
| 4,690,915 A | 9/1987 | Rosenberg |
| 5,827,642 A | 10/1998 | Riddell et al. |
| 6,040,177 A | 3/2000 | Riddell et al. |
| 6,294,063 B1 | 9/2001 | Becker et al. |
| 6,942,776 B2 | 9/2005 | Medoro |
| 7,090,759 B1 | 8/2006 | Seul |
| 7,699,969 B2 | 4/2010 | Manaresi et al. |
| 7,956,339 B2 | 6/2011 | Ohta et al. |
| 8,581,167 B2 | 11/2013 | Lean et al. |
| 9,068,281 B2 | 6/2015 | Wu et al. |
| 9,144,806 B2 | 9/2015 | Chen et al. |
| 9,403,172 B2 | 8/2016 | Short et al. |
| 10,723,988 B2 | 7/2020 | Lowe et al. |
| 10,799,865 B2 | 10/2020 | Lowe et al. |
| 11,007,520 B2 | 5/2021 | Lowe et al. |
| 2002/0058019 A1 | 5/2002 | Berenson et al. |
| 2003/0008364 A1 | 1/2003 | Wang et al. |
| 2003/0170238 A1 | 9/2003 | Gruenberg et al. |
| 2003/0198968 A1 | 10/2003 | Matson |
| 2004/0072278 A1 | 4/2004 | Chou et al. |
| 2004/0115216 A1 | 5/2004 | Schneck et al. |
| 2004/0191789 A1 | 9/2004 | Manaresi et al. |
| 2004/0197905 A1 | 10/2004 | Hafeman |
| 2004/0248205 A1 | 12/2004 | Stern et al. |
| 2005/0089993 A1 | 4/2005 | Boccazzi et al. |
| 2005/0112548 A1 | 5/2005 | Segawa et al. |
| 2005/0129581 A1 | 6/2005 | McBride et al. |
| 2005/0152916 A1 | 7/2005 | Cai et al. |
| 2005/0164402 A1 | 7/2005 | Belisle et al. |
| 2005/0175981 A1 | 8/2005 | Voldman et al. |
| 2005/0274456 A1 | 12/2005 | Roitman et al. |
| 2006/0091015 A1 | 5/2006 | Lau |
| 2006/0154361 A1 | 7/2006 | Wikswo et al. |
| 2006/0240548 A1 | 10/2006 | Deutsch et al. |
| 2006/0263612 A1 | 11/2006 | Chen et al. |
| 2006/0269973 A1 | 11/2006 | Yee |
| 2007/0095669 A1 | 5/2007 | Lau et al. |
| 2007/0183934 A1 | 8/2007 | Diercks et al. |
| 2007/0264481 A1 | 11/2007 | DeSimone et al. |
| 2008/0013092 A1 | 1/2008 | Maltezos et al. |
| 2008/0153134 A1 | 6/2008 | Wiyatno et al. |

(Continued)

FOREIGN PATENT DOCUMENTS

| | | |
|---|---|---|
| CN | 1419597 A | 5/2003 |
| CN | 101275114 A | 10/2008 |

(Continued)

OTHER PUBLICATIONS

Huxley et al. High-affinity small molecule inhibitors of T cell costimulation: Compounds for immunotherapy. Chemistry & Biology 2004, 11;12:1651-1658. (Year: 2004).*
Doh et al. Immunological synapse array: Patterned protein surfaces that modulate immunological synapse structure formation in T cells. PNAS 2006, 103;15:5700-5705. (Year: 2006).*
Shen et al. Micropatterning of costimulatory ligands enhances CD4+ T cell function. PNAS 2008, 105;22:7791-7796. (Year: 2008).*
Vila et al. Identification of protein targets of 4-hydroxynonenal using click chemistry for ex vivo biotinylation of azido and alkynyl derivatives. Chemical Research in Toxicology 2008: 21:432-444. (Year: 2008).*
Miltenyi. Product datasheet, 2008. (Year: 2008).*
Maduro. Structural and biophysical insights from targeting melanoma using genetically modified T cell receptors. PhD dissertation, Cardiff University, 2013. (Year: 2013).*

(Continued)

*Primary Examiner* — Allison M Fox
*Assistant Examiner* — Jennifer S Spence
(74) *Attorney, Agent, or Firm* — Shay Glenn LLP

(57) ABSTRACT

In biosciences and related fields, it can be useful to modify surfaces of apparatuses, devices, and materials that contact biomaterials such as biomolecules and biological microobjects. Described herein are surface modifying and surface functionalizing reagents, preparation thereof, and methods for modifying surfaces of wells within a well plate to activate lymphocytes, including but not limited to T lymphocytes, in a controllable and reproducible manner.

27 Claims, 15 Drawing Sheets

(56) References Cited

U.S. PATENT DOCUMENTS

| | | |
|---|---|---|
| 2008/0223721 A1 | 9/2008 | Cohen et al. |
| 2008/0241892 A1* | 10/2008 | Roitman ............ C40B 50/14 |
| | | 435/174 |
| 2008/0302732 A1 | 12/2008 | Soh et al. |
| 2008/0318203 A1 | 12/2008 | Tran et al. |
| 2009/0023608 A1 | 1/2009 | Hung et al. |
| 2009/0136912 A1 | 5/2009 | Kurokawa et al. |
| 2009/0170186 A1 | 7/2009 | Wu et al. |
| 2010/0000366 A1 | 1/2010 | Nomura et al. |
| 2010/0273681 A1 | 10/2010 | Cerrina et al. |
| 2011/0053151 A1 | 3/2011 | Hansen et al. |
| 2011/0053783 A1 | 3/2011 | Du et al. |
| 2011/0117634 A1 | 5/2011 | Halamish et al. |
| 2011/0143964 A1 | 6/2011 | Zhou et al. |
| 2011/0186165 A1 | 8/2011 | Borenstein et al. |
| 2011/0250614 A1 | 10/2011 | Perez et al. |
| 2011/0262906 A1 | 10/2011 | Dimov et al. |
| 2011/0293637 A1 | 12/2011 | Hacohen et al. |
| 2011/0301058 A1 | 12/2011 | Cheng et al. |
| 2012/0009671 A1 | 1/2012 | Hansen et al. |
| 2012/0015347 A1 | 1/2012 | Singhal et al. |
| 2012/0118740 A1 | 5/2012 | Garcia et al. |
| 2012/0121649 A1 | 5/2012 | Santamaria |
| 2012/0156675 A1 | 6/2012 | Lueerssen et al. |
| 2012/0208266 A1 | 8/2012 | Bookbinder et al. |
| 2012/0325665 A1 | 12/2012 | Chiou et al. |
| 2013/0115606 A1 | 5/2013 | Hansen et al. |
| 2013/0118905 A1 | 5/2013 | Morimoto et al. |
| 2013/0130232 A1 | 5/2013 | Weibel et al. |
| 2013/0146459 A1 | 6/2013 | Bazant et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2014/0045277 A1 | 2/2014 | Gordon et al. |
| 2014/0116881 A1 | 5/2014 | Chapman et al. |
| 2014/0154703 A1 | 6/2014 | Skelley et al. |
| 2014/0154791 A1 | 6/2014 | North et al. |
| 2014/0235507 A1 | 8/2014 | Snyder et al. |
| 2014/0274771 A1 | 9/2014 | Elizazu et al. |
| 2015/0018226 A1 | 1/2015 | Hansen et al. |
| 2015/0151298 A1 | 6/2015 | White et al. |
| 2015/0151307 A1 | 6/2015 | Breinlinger et al. |
| 2015/0165436 A1 | 6/2015 | Chapman et al. |
| 2015/0167043 A1 | 6/2015 | Goluch et al. |
| 2016/0184821 A1 | 6/2016 | Hobbs et al. |
| 2016/0199837 A1 | 7/2016 | Breinlinger et al. |
| 2016/0252495 A1 | 9/2016 | Ricicova et al. |
| 2017/0307502 A1 | 10/2017 | Mason et al. |
| 2018/0298318 A1 | 10/2018 | Kurz et al. |
| 2019/0240665 A1 | 8/2019 | Lionberger et al. |

FOREIGN PATENT DOCUMENTS

| | | | |
|---|---|---|---|
| EP | 0421380 B1 | 12/1995 | |
| JP | 2012184233 A | 9/2012 | |
| JP | 2016516406 A | 6/2016 | |
| JP | 2017513891 A | 6/2017 | |
| JP | 2019508050 A | 3/2019 | |
| KR | 20100008222 A | 1/2010 | |
| WO | WO02/088702 A2 | 11/2002 | |
| WO | WO-2004017042 A2 * | 2/2004 | ............ B82Y 30/00 |
| WO | WO2005/100541 A2 | 10/2005 | |
| WO | WO2008/057366 A2 | 5/2008 | |
| WO | WO2008/119066 A1 | 10/2008 | |
| WO | WO2009/045308 A2 | 4/2009 | |
| WO | WO2010/115167 A2 | 10/2010 | |
| WO | WO2010/147078 A1 | 12/2010 | |
| WO | WO2010/147942 A1 | 12/2010 | |
| WO | WO2012/037030 A2 | 3/2012 | |
| WO | WO2012/072823 A1 | 6/2012 | |
| WO | WO2013/019491 A1 | 2/2013 | |
| WO | WO2016/105542 A2 | 6/2016 | |
| WO | WO2016/105542 A3 | 6/2016 | |
| WO | WO2017/161210 A1 | 9/2017 | |
| WO | WO2017/205830 A1 | 11/2017 | |
| WO | WO2018/018017 A1 | 1/2018 | |
| WO | WO2019/018801 A1 | 1/2019 | |

OTHER PUBLICATIONS

Skanland et al. T cell co-stimulation through the CD2 and CD28 co-receptors induces distinct signalling responses. Biochemical Journal 2014, 460:399-410. (Year: 2014).*

JenKem Technology USA. Webpage capture (https://web.archive.org/web/20170511033319/https://www.jenkemusa.com/product-category/click-chemistry-pegs/), 2017. (Year: 2017).*

Banuls et al. Chemical surface modifications for the development of silicon-based label-free integrated optical (IO) biosensors: A review; ? Analytica Chimica Acta; 777; pp. 1-16 ; May 13, 2013.

Bellis; Advantages of RGD peptides for directing cell association with biomaterials; PMC manuscript of Biomaterials; 32; pp. 4205-4210; 12 pages (Author Manuscript); Jun. 2011.

Chen et al.; Regioselective Patterning ot Multiple SAMs and Applications in Surface-Guided Smart Microfluidics; ACS Applied Materials & Interfaces; 6(24); p. 21961-21969; Dec. 24, 2014.

Chiou et al.; Massively Parallel Manipulation of Single Cells and Microparticles Using Optical Images; Nature; (436) pp. 370-372; Jul. 2005.

Chiou; Massively parallel optical manipulation of single cells, mirco- and nano-particles on optoelectronic devices; University of California at Berkeley; 147 pages; (Dissertation); 2005 (the year of publication is sufficiently earlier than the effective U.S. filing date and any foreign priority date so that the particular month of publication is not an issue).

Chow et al.; Peptide-based biopolymers in biomedicine and biotechnology; Materials Science and Engineering; 62(4); p. 125-155; Sep. 2008.

Chung et al., Imaging single-cell signaling dynamics with a deterministic high-density single-cell trap array; Anal.Chem.; 83(18); pp. 7044-7052; 14 pages (Author Manuscript); Aug. 23, 2011.

CN101275114A, Lou—Machine Translation, Oct. 1, 2008, 8 pages.

Hsu et al.; Sorting of Differentiated Neurons Using Phototransistor-Based Optoelectronic Tweezers for Cell Replacement Therapy of Neurodegenerative Diseases; Transducers 2009 Conf.; pp. 1598-1601; Jun. 2009.

Hung et al.; Continuous Perfusion Microfluidic Cell Culture Array for High-Throughput Cell-Based Assays; Biotech and Bioengineering 89(1); pp. 1-8 ; Jan. 2005.

Iliescu et al.; Continuous field-flow separation of particle populations in a dielectrophoretic chip with three dimensional electrodes; Applied Physics Letters 90(23); pp. 234104, 4pages; Jun. 2007.

Kim et al.; A practical guide to microfluidic perfusion culture of adherent mammalian cells; Lab on a Chip; 7(6); pp. 681-694; 2007 (the year of publication is sufficiently earlier than the effective U.S. filing date and any foreign priority date so that the particular month of publication is not an issue).

KIPO computer-generated English language translation of KR 201000008222A _Kyun; 10 pages; Jan. 2010.

Lowe; Controlled Vapor Deposition of Azide-Terminated Siloxane Monolayers: A Platform for Tailoring Oxide Surfaces; (dissertation); Stanford University: 152 pgs.; published: Aug. 2011.

Lowe et al.; Deposition of dense siloxane monolayers from water and trimethoxyorganosilane; Langmuir; 27(16); pp. 9928-9935; Aug. 2011.

Mazurek et al.; Preparing mono-dispersed liquid core PDMS microcapsules from thiol-ene-epoxy-tailored flow-focusing microfluidic devices; RSC Advances; 5(20); pp. 15379-15386; Jan. 26, 2015.

Mehling et al.; Microfluidic Cell Culture, Current Opinion in Biotechnology; 25; pp. 95-102; Feb. 2014.

Nevill et al.; Integrated Microfluidic Cell Culture and Lysis on a Chip; Lab Chip; (12) pp. 1689-1695; Oct. 2007.

Somaweera et al.; "Generation of a Chemical Gradient Across an Array of 256 Cell Cultures in a Single Chip"; Analyst; 138(19); doi:10.1039/C3an00946g; 14 pgs.; (Author Manuscript); Oct. 2013.

(56) References Cited

OTHER PUBLICATIONS

Valley et al.; Optoelectronic Tweezers as a Tool for Parallel Single-Cell Manipulation and Stimulation; IEEE Trans Biomed Circuits Syst.; 3(6); pp. 424-431; Dec. 2009.
WO2010147078, University of Tokyo, Machine Translation, Dec. 23, 2010; 12 pages.
Xu et al.; Recent Trends in Dielectrophoresis; Informacije Midem; 40(4) pp. 253-262; Dec. 2010.
Yi et al.; Microfluidics Technology for Manipulation and Analysis of Biological Cells; Anal Chim Acta; (560) pp. 1-23; Feb. 2006.
Young et al.; Fundamentals of Microfluidic Cell Culture in Controlled Microenvironments; cited as Chem Soc Rev.; Mar. 2010; 39(3); pp. 1036-1048; pub online Feb. 2010; doi: 10.1039/b909900j; (24 pgs).
Zhang et al.; "Click" Chemistry-Based Surface Modification of poly(dimethylsiloxane) for Protein Separation in a Microfluidic Chip; Electrophoresis; 31(18); p. 3129-3136; Sep. 20, 2010.
Zhang et al.;Azide Functional Monolayers Grafted to a Germanium Surface Model Substrates for ATR-IR Studies of interfacial Click Reactions; Langmuir ; 28(1); pp. 486-493; Dec. 8, 2011.
Chang et al.; Phase II trial of autologous tumor vaccination, anti-CD3-activated vaccine-primed lymphocytes, and interleukin-2 in stage IV renal cell cancer; Journal of Clinical Oncology; 21(5); pp. 884-890; Mar. 2003.
Alajez et al.; Therapeutic potential of a tumor-secific, MHC-unrestricted T-cell receptor expressed on effector cells of the innate and the adaptive immune system through bone marrow transduction and immune reconstitution; Blood; 105(12); pp. 4583-4589; Jun. 2005.
Bear et al.; Adoptive immunotherapy of cancer with pharmacologically activated lymph mode lymphocytes: a polit clinical trial; Cancer Immunology, Immunotherapy; 50(5); pp. 269-274; Jul. 2001.
Cooper et al.; T-cell clones can be rendered specific for CD19: toward the selective augmentation of the graft-versus-B-lineage leukemia effect; Blood; 101(4); pp. 1637-1644; Feb. 15, 2003.
Dudley et al.; Cancer regression and autoimmunity in patients after clonal repopulation with antitumor lymphocytes; Science; 298(5594); pp. 850-854; 10 pages (Author Manuscript); Oct. 2002.
EBioMedicine; Natural killer cells for cancer immunotherapy: a new car is catching up; EBioMedicine; 39; pp. 1-2; Jan. 2019.
Powell et al.; Transition of late-stage effector t cells to CD27+ CD28+ tumor-reactive effector memory t cells in humans after adoptive cell transfer therapy; Blood; 105(1); pp. 241-250; 25 pages; (Author Manuscript); Jan. 2005.
Roszowski et al.; Simultaneous generation of CD8+ and CD4+ melanoma-reactive t cells by retroviral-mediated transfer of a single t-cell receptor; Cancer Research; 65(4); pp. 1570-1576; Feb. 15, 2005.
Schultze et al.; A pilot study of combined immunotherapy with autologous adoptive tumour-specific T-cell transfer, vaccination with CD40-activated malinant B cells and interleukin 2; British Journal of Haematology; 113(2); pp. 455-460; May 2001.
Kelly-Greene et al.; U.S. Appl. No. 17/819,447 entitled "Well-plate incubator," filed Aug. 12, 2022.
Newstrom et al.; U.S. Appl. No. 17/936,478 entitled "Well-plate incubator," filed Sep. 29, 2022.

\* cited by examiner

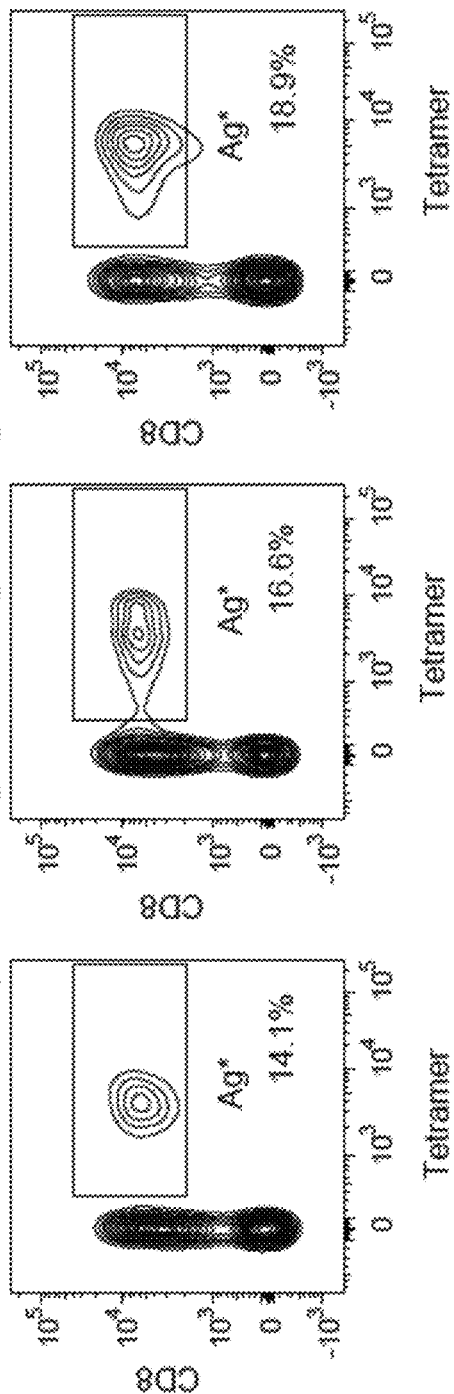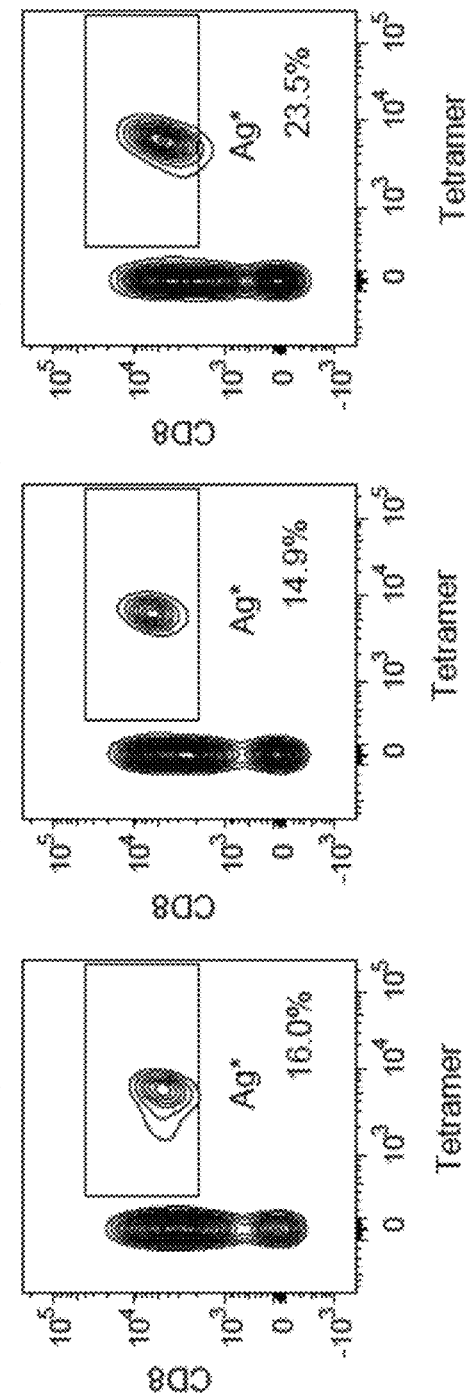
FIG. 7A
FIG. 7B

FUNCTIONALIZED WELL PLATE, METHODS OF PREPARATION AND USE THEREOF

CROSS REFERENCE TO RELATED APPLICATIONS

This application claims the benefit of U.S. Provisional Application No. 62/734,924, filed on Sep. 21, 2018, entitled "FUNCTIONALIZED WELL PLATE, METHODS OF PREPARATION AND USE THEREOF"; and U.S. Provisional Application No. 62/893,712, filed on Aug. 29, 2019, entitled "FUNCTIONALIZED WELL PLATE, METHODS OF PREPARATION AND USE THEREOF", each of which disclosures are herein incorporated by reference in its entirety.

BACKGROUND OF THE INVENTION

Immunotherapy offers a potentially powerful approach to treating cancers successfully. T lymphocyte activation by antigen presenting dendritic cells is one aspect of preparing tumor-targeting cytotoxic T lymphocytes for use in immunotherapy. Activation by dendritic cells may be improved by using more reproducible and better characterizable technologies. Some embodiments of the present invention include modified surfaces of a well plate configured to activate T lymphocytes, related methods of using such modified surfaces to activate T lymphocytes, and compositions containing such activated T lymphocytes.

SUMMARY OF THE INVENTION

In a first aspect, a well plate is provided, including a surface having a first region which is a reactive moiety-presenting covalently functionalized region or an activating moiety-presenting covalently functionalized region, where the reactive moiety is an azido moiety, a biotin moiety or a streptavidin moiety and the activating moiety is a lymphocyte-activating moiety. The first region may have an area of at least 0.5 mm$^2$ (e.g., about 0.5 mm$^2$ to about 50 mm$^2$, about 1.0 mm$^2$ to about 40 mm$^2$, about 2 mm$^2$ to about 35 mm$^2$, about 3 mm$^2$ to about 30 mm$^2$, or about 4 mm$^2$ to about 25 mm$^2$). The first region may be substantially circular and have a diameter of about 0.5 mm to about 4.0 mm (e.g., about 1.0 mm to about 35 mm, or about 1.5 mm to about 3.0 mm). The first region may have a density of respective reactive moieties or activating moieties of at least 50/um$^2$. The reactive moieties or activating moieties may be linked covalently to the surface via a linker, such as an organic linker. The linker can have from 5 to about 20 backbone atoms, about 10 to about 40 backbone atoms, or about 15 to about 50 backbone atoms selected from carbon, silicon, nitrogen and oxygen. The surface of the well plate may further include a second region which is a covalently modified region including surface blocking ligands. Optionally, the second region may surround the first region. In some embodiments, each of the surface blocking ligands may include a hydrophilic or negatively charged moiety. In some embodiments, each of the surface blocking ligands may include polyethylene glycol (PEG) moieties. The surface of the well plate may include glass or polystyrene. In some variations, the surface of the well plate may include polypropylene, polycarbonate, polyethylene, cycloolefin copolymer, or melamine.

In some variations, the reactive moiety may be streptavidin, and the streptavidin functionality is covalently attached to the first region of the surface of the well plate. In other variations, the reactive moiety may be streptavidin, and the streptavidin functionality is non-covalently attached to a biotin moiety which is itself covalently attached to the first region of the surface of the well plate.

In some variations, the first region may be an activating moiety-presenting covalently functionalized region including a plurality of specifically bound primary activating molecular ligands and a plurality of specifically bound co-activating molecular ligands. A ratio of the primary activating molecular ligands to the co-activating molecular ligands on the first region of the surface may be about 1:10 to about 2:1 (e.g., about 1:5 to about 2:1, about 1:2 to about 2:1, about 1:10 to about 1:1, about 1:5 to about 1:1, about 1:1 to about 2:1, or about 1:2 to about 1:1). In some embodiments, each ligand of the plurality of specifically bound primary activating molecular ligands may include a major histocompatibility complex (MHC) molecule configured to bind to a T cell receptor (TCR) of a T cell. The MHC molecule may be a Class I or Class II molecule and may further include an antigenic peptide. The antigenic peptide may be a tumor-associated antigen, a viral antigen, a bacterial antigen, a fungal antigen, or a protozoan antigen. In some variations, each ligand of the plurality of specifically bound co-activating molecular ligands may include a T cell receptor (TCR) co-activating molecule or an adjunct TCR activating molecule. A ratio of the TCR co-activating molecules to the adjunct TCR activating molecules of the plurality of co-activating molecular ligands is about 100:1 to about 1:100 (e.g., about 20:1 to about 1:20, or about 3:1 to about 1:3). In some variations, the TCR co-activating molecules may include a CD28 binding protein (e.g., a CD80 molecule or an anti-CD28 antibody), or a fragment thereof, which retains binding ability to CD28. In some variations, the adjunct TCR activating molecule may include a CD2 binding protein (e.g., a CD58 molecule or an anti-CD2 antibody), or a fragment thereof, which retains binding activity to CD2.

The plurality of specifically bound primary activating molecular ligands may have a density of at least about $1\times10^2$ molecules per square micron in the first region, and optionally, a density of about $1\times10^2$ to about $1\times10^5$ molecules per square micron in the first region. The plurality of specifically bound co-activating molecular ligands has a density of at least $1\times10^2$ molecules per square micron in the first region, and optionally, a density of about $1\times10^3$ to about $1\times10^5$ molecules per square micron in the first region.

In another aspect, a well plate is provided, where each of one or more wells (e.g., all wells) of the well plate includes the surface and the first region thereof, where the first region is a reactive moiety-presenting covalently functionalized region or an activating moiety-presenting covalently functionalized region like any well plate having the surface and first region as described above or elsewhere herein. The first region of each of the one or more wells may be located on a bottom surface of the corresponding well(s). An area of each first region may be less than about 50% (e.g., less than about 40%, less than about 30%, less than about 25%, less than about 20%, less than about 15%, less than about 10%, less than about 5%, or less than about 2%) of the area of the bottom surface of the corresponding well(s). In some embodiments, each of the one or more wells further comprises a second region which is a covalently modified region including surface blocking ligands. Each second region can optionally surround the first region of the corresponding well(s). Each of the surface blocking ligands of the second region, when present, may include a hydrophilic or negatively charged moiety. In some embodiments, the surface blocking ligands may include polyethylene glycol (PEG) moieties.

In another aspect, a well plate including a surface having an azido-presenting covalently functionalized region is provided. The azido-presenting covalently functionalized region may encompass part or all of the well plate surfaces, or may be distributed on fewer than all the surfaces of the well plate. In some variations, one or more wells of the well plate may include a surface having an azido-presenting covalently functionalized region. The azido-presenting covalently functionalized region of each of the one or more wells may encompass the entire surface (i.e., inner surface) of the corresponding well or may be located on a bottom surface of the corresponding well. The surface of the well plate or the surface of the one or more wells of the well plate may comprise glass or polymer, which may be any suitable type of polymer.

In some embodiments, the azido-presenting covalently functionalized region may have an area of at least 0.5 $mm^2$ (e.g., at least 1 $mm^2$, at least 10 $mm^2$, at least 100 $mm^2$, at least 1000 $mm^2$, at least 10,000 $mm^2$, at least 100,000 $mm^2$, or any range defined by two of the foregoing endpoints). The azido-presenting covalently functionalized region may have a density of azido groups of at least 50/$um^2$. In some embodiments, the azido functionalities linked covalently to the surface may be linked via a linker having at least 5 backbone atoms selected from carbon, silicon, nitrogen and oxygen. For example, the azido functionalities may be linked covalently to the surface through a series of 5 to about 20 backbone atoms, or about 10 to about 40 backbone atoms, or about 5, 7, 9, 10, 11, 13, 15, 20, 25, 30, 35, 40, 45, 50, 55, 60, 65, 70, 75, 80, 90, 100, 200 bond lengths, of a linker or any number of backbone atoms therebetween.

In another aspect, a well plate including a surface including a biotin-presenting covalently functionalized region is provided, and may encompass part of the well plate surface, and/or may be distributed on fewer than all the surfaces of the well plate. In some embodiments, one or more wells of the well plate may include a surface having a biotin-presenting covalently functionalized region. In some embodiments, the biotin-presenting covalently functionalized region of the one or more wells may be located on a bottom surface of the corresponding well. The surface of the well plate or the surface of the one or more wells of the well plate may comprise glass or polymer, which may be any suitable type of polymer.

In some variations, the biotin-presenting covalently functionalized region may have an area of at least 0.5 $mm^2$ (e.g., at least 1.0 $mm^2$, at least 2.0 $mm^2$, at least 3.0 $mm^2$, at least 4.0 $mm^2$, at least 5.0 $mm^2$, at least 6.0 $mm^2$, at least 7.0 $mm^2$, at least 8.0 $mm^2$, at least 9.0 $mm^2$, at least 10.0 $mm^2$, at least 15 $mm^2$, at least 20 $mm^2$, at least 25 $mm^2$, or at least 50 $mm^2$, or any range defined by two of the foregoing endpoints). In some embodiments, the biotin-presenting covalently functionalize region may have an area of less than 100 $mm^2$. In some embodiments, the biotin-presenting covalently functionalized region may have a density of biotin functionalities of at least 50/$um^2$. In some variations, the biotin-presenting covalently functionalized region may include biotin functionalities linked covalently to the surface via a linker having at least 10 backbone atoms selected from carbon, silicon, nitrogen and oxygen. For example, the linker can have about 5 to about 200 backbone atoms, or about 10 to about 40 backbone atoms selected from carbon, silicon, nitrogen and oxygen, or any number of backbone atoms therebetween.

In some embodiments, the area of the biotin-presenting covalently functionalized region may be from about less than 2% to about less than about 50% of the area of the bottom of each of the one or more wells. In some embodiments, the biotin-presenting covalently functionalized region may have a dimension of 0.5 to 4.0 mm (e.g., about 1.0 mm to about 35 mm). In various embodiments, the biotin presenting covalently functionalized region may be substantially circular and has a diameter of 0.5 to 4.0 mm (e.g., about 1.0 mm to about 35 mm).

In some embodiments, the surface of the well plate or each of the one or more wells further may include a second covalently modified region including surface blocking ligands. In some embodiments, each of the surface blocking ligands may include a hydrophilic or negatively charged moiety. In some embodiments, the surface blocking ligands may include polyethylene glycol (PEG) moieties. In some embodiments, the second covalently modified region further may include at least one ligand providing a moiety stimulating adherence.

In another aspect, a well plate including a surface having a streptavidin-presenting covalently functionalized region is provided. The streptavidin-presenting covalently functionalized region may encompass part of the well plate surface, and/or may be distributed on fewer than all the surfaces of the well plate. In some variations, one or more wells of the well plate may include a surface having a streptavidin-presenting covalently functionalized region. In some embodiments, the streptavidin-presenting covalently functionalized region of the one or more wells may be located on a bottom surface of the corresponding well. The surface of the well plate or the surface of the one or more wells of the well plate may comprise glass or polymer, which may be any suitable type of polymer.

In some embodiments, the streptavidin functionality may be covalently attached to the covalently functionalized region of the surface of the well plate or the one or more wells of the well plate. The streptavidin functionalities may be linked covalently to the surface via a linker having about 5 to about 200 backbone atoms, or about 10 to about 50 backbone atoms selected from carbon, silicon, nitrogen and oxygen, or any number of backbone atoms therebetween. When streptavidin is itself covalently linked to the surface, the linkage may be via coupling to azido functionalities of any azido-presenting covalently functionalized region of a surface as described herein. In some other embodiments, the streptavidin functionality may be non-covalently attached to a biotin moiety, which is itself covalently attached to the covalently functionalized region of the surface of the well plate or the one or more wells of the well plate, as previously mentioned.

The streptavidin-presenting covalently functionalized region may have an area of at least 0.5 $mm^2$ (e.g., at least 1.0 $mm^2$, at least 2.0 $mm^2$, at least 3.0 $mm^2$, at least 4.0 $mm^2$, at least 5.0 $mm^2$, at least 6.0 $mm^2$, at least 7.0 $mm^2$, at least 8.0 $mm^2$, at least 9.0 $mm^2$, at least 10.0 $mm^2$, at least 15 $mm^2$, at least 20 $mm^2$, at least 25 $mm^2$, or at least 50 $mm^2$, or any range defined by two of the foregoing endpoints). In some embodiments, the biotin-presenting covalently functionalize region may have an area of less than 100 $mm^2$. In some embodiments, the streptavidin-presenting covalently functionalized region may have a density of streptavidin functionalities of at least 50/$um^2$. In some embodiments, the streptavidin-presenting covalently functionalized region may have an area of less than about 2% to less than about 50% of an area of a bottom surface of each of the one or more wells, or any area therebetween. In some embodiments, the streptavidin-presenting covalently functionalized region may have a dimension of 0.5 to 4.0 mm (e.g., about 1.0 mm to about 35 mm). In some embodiments, the streptavidin-presenting covalently functionalized region may be substantially circular and has a diameter of 0.5 to 4.0 mm (e.g., about 1.0 mm to about 35 mm).

In some embodiments, the surface of the well plate or each of the one or more wells further may include a second covalently modified region including surface blocking ligands. In some embodiments, each of the surface blocking ligands may include a hydrophilic or negatively charged moiety. In some embodiments, the surface blocking ligands may include polyethylene glycol (PEG) moieties. In some embodiments, the second covalently modified region further may include at least one ligand providing a moiety stimulating adherence.

In another aspect, a well plate including a surface including an antigen-presenting covalently functionalized region of the well plate for activating a T cell is provided. The antigen-presenting covalently functionalized region may encompass part of the well plate surfaces, and/or may be distributed on fewer than all the surfaces of the well plate. In some embodiments, one or more wells of the well plate may include a surface having an antigen-presenting covalently functionalized region. In some embodiments, the antigen-presenting covalently functionalized region of the one or more wells may be located on a bottom surface of the corresponding well.

The antigen-presenting covalently functionalized region may include a plurality of specifically bound primary activating molecular ligands and a plurality of specifically bound co-activating molecular ligands. A ratio of the primary activating molecular ligands to the co-activating molecular ligands on the covalently functionalized region may be about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1. In some variations, the plurality of specifically bound primary activating molecular ligands each may include a major histocompatibility complex (MHC) molecule (e.g., Class I or Class II) configured to bind to a T cell receptor of the T cell. In some embodiments, the MHC molecule may include an MHC Class I protein sequence and a beta microglobulin protein sequence. The protein sequence of the MHC molecule may be connected to the antigen-presenting synthetic surface via a C-terminal connection of the protein sequence. In some embodiments, each of the plurality of primary activating molecules including an MHC molecule further may include an antigenic peptide, such as a tumor associated antigenic peptide, a viral antigen, a bacterial antigen, a fungal antigen, or a protozoan antigen. In some embodiments, the antigenic peptide is a tumor associated antigenic peptide, which may be SLC45A2, TCL1, VCX3A, MART1 or NYESO1.

In some variations, the plurality of specifically bound co-activating molecular ligands each may include a T cell receptor (TCR) co-activating molecule or an adjunct TCR activating molecule. A ratio of the TCR co-activating molecules to the adjunct TCR activating molecules of the plurality of co-activating molecular ligands may be about 100:1 to about 1:100, about 20:1 to about 1:20 or about 3:1 to about 1:3. In some embodiments, the TCR co-activating molecules may include a CD28 binding protein or a fragment thereof, which retains binding ability to CD28. The CD28 binding protein may be a CD80 molecule or a fragment thereof, where the fragment retains binding activity to CD28; an anti-CD28 antibody or a fragment thereof, which retains binding activity to CD28. In some embodiments, the adjunct TCR activating molecule may include a CD2 binding protein, or a fragment thereof retaining binding activity to CD2. The CD2 binding protein may be a CD58 molecule or fragment thereof, where the fragment retains binding activity with CD2; or an anti-CD2 antibody or a fragment thereof where the fragment retains binding activity with CD2. In some embodiments, the plurality of specifically bound primary activating molecular ligands and a plurality of specifically bound co-activating molecular ligands may be specifically bound to streptavidin functionalities of a streptavidin-presenting covalently functionalized region of a well plate like any well plate having a surface including a streptavidin-presenting covalently functionalized region described herein.

In some embodiments, the plurality of specifically bound primary activating molecular ligands may have a density of at least about $1 \times 10^2$ molecules per square micron or from about $1 \times 10^2$ to about $1 \times 10^5$ molecules per square micron in the antigen-presenting covalently functionalized region. In some embodiments, the plurality of specifically bound co-activating molecular ligands may have a density from about $1 \times 10^2$ to about $1 \times 10^5$ molecules per square micron or about $1 \times 10^3$ to about $1 \times 10^5$ molecules per square micron on the antigen-presenting synthetic surface in the antigen-presenting covalently functionalized region.

In another aspect, a method of activating T lymphocytes (T cells) is providing, where the method includes contacting a plurality of T cells with an antigen-presenting covalently functionalized region of a surface of a well plate, thereby converting at least a portion of the plurality of T cells to activated T cells. The antigen-presenting covalently functionalized region may include a plurality of primary activating molecular ligands, each including a major histocompatibility (MHC) molecule (e.g., Class I or Class II) configured to bind to a T cell receptor (TCR) of a T cell and, further, each of the plurality of primary activating molecular ligands may be linked to the surface. The antigen-presenting covalently functionalized region may further include a plurality of co-activating molecular ligands, each including a T cell receptor (TCR) co-activating molecule or an adjunct TCR activating molecule and each of the co-activating molecular ligands may be linked to the surface. The plurality of T cells may be cultured in contact with the antigen-presenting covalently functionalized region of the surface, thereby converting at least a portion of the plurality of T cells to activated T cells. The T cells may include CD8+ T cells.

The antigen-presenting covalently functionalized region may be a first region of a surface of a well plate like any well plate having an activating moiety-presenting covalently functionalized region as described above or elsewhere herein.

In some variations, the plurality of co-activating molecular ligands may include TCR co-activating molecules and adjunct TCR activating molecules. A ratio of the TCR co-activating molecules to the adjunct TCR activating molecules of the plurality of co-activating molecular ligands may be about 100:1 to about 1:100, about 20:1 to about 1:20, or about 3:1 to about 1:3.

Each molecule of the plurality of MHC molecules may include an MHC Class I protein sequence, a beta microglobulin protein sequence, and an antigenic peptide. In some variations, the protein sequence of the MHC molecule is connected to the antigen-presenting covalently functionalized region of the surface via a C-terminal connection. The MHC molecule may include a biotin moiety and may be attached to the antigen-presenting covalently functionalized region of the surface via a noncovalent interaction with streptavidin. In some embodiments, the streptavidin is itself covalently bonded to the antigen-presenting covalently functionalized region of the surface. In other embodiments, the streptavidin may be noncovalently associated with the antigen-presenting covalently functionalized region of the surface. When streptavidin is noncovalently associated with a biotin moiety, the biotin moiety may be covalently bonded to the antigen-presenting covalently functionalized region of the surface.

In some variations, the antigenic peptide may be a tumor-associated antigen, a viral antigen, a bacterial antigen, a fungal antigen, or a protozoan antigen. In some embodiments, the antigenic peptide may be a tumor-associated antigen. In some variations, the tumor-associated antigen may be SLC45A2, TCL1, VCX3A, MART1 or NYESO1.

In some variations, each of the plurality of co-activating molecule ligands may be linked to the antigen-presenting covalently functionalized region of the surface.

In some variations, the T cell receptor (TCR) co-activating molecule may include a CD28 binding protein, or a fragment thereof which retains binding ability to CD28; a CD80 molecule or a fragment thereof, where the fragment retains binding activity to CD28; or an anti-CD28 antibody or a fragment thereof, where the fragment retain binding activity to CD28.

In some variations, the adjunct TCR activating molecule may include a CD2 binding protein, or a fragment thereof, which retains binding ability to CD2. The adjunct TCR activating molecule may include a CD58 molecule or fragment thereof, where the fragment retains binding activity with CD2; or an anti-CD2 antibody or a fragment thereof, where the fragment retains binding activity with CD2.

The plurality of specifically bound primary activating molecular ligands may have a density of at least about $1\times10^2$ molecules per square micron in the antigen-presenting covalently functionalized region of the surface. In some embodiments, the plurality of specifically bound primary activating molecular ligands may have a density from about $1\times10^2$ to about $1\times10^5$ molecules per square micron in the antigen-presenting covalently functionalized region of the surface. The plurality of specifically bound co-activating molecular ligands may have a density of at least $1\times10^2$ to about $1\times10^5$ molecules per square micron in the antigen-presenting covalently functionalized region of the surface. In some embodiments, the plurality of specifically bound co-activating molecular ligands may have about $1\times10^3$ to about $1\times10^5$ molecules per square micron in the antigen-presenting covalently functionalized region of the surface. A ratio of the primary activating molecular ligands to the co-activating molecular ligands in the antigen-presenting covalently functionalized region of the surface may be about 1:10 to about 2:1, about 1:5 to about 2:1, about 1:2 to about 2:1, about 1:10 to about 1:1, about 1:5 to about 1:1, about 1:1 to about 2:1, or optionally, about 1:2 to about 1:1. In some variations, a ratio of the TCR co-activating molecules to the adjunct TCR activating molecules of the plurality of co-activating molecular ligands may be about 3:1 to about 1:3. In some embodiments, the ratio of the TCR co-activating molecules to the adjunct TCR activating molecules of the plurality of co-activating molecular ligands may be about 2:1 to about 1:2. In some embodiments, the ratio of the TCR co-activating molecules to the adjunct TCR activating molecules of the plurality of co-activating molecular ligands may be about 1:1.

In some variations, the method may further include contacting the plurality of T cells with a plurality of adhesion-stimulating molecular ligands. The plurality of adhesion-stimulating molecular ligands may include an ICAM molecule.

In some variations, the method may further include contacting the plurality of T cells with a plurality of growth stimulatory molecular ligands. In some embodiments, each of the growth stimulatory molecular ligands may include a growth factor receptor ligand. The growth factor receptor ligand may include IL-21 or a fragment thereof.

In some variations, contacting the plurality of T cells with the plurality of growth stimulatory molecular ligands may be performed after a first period of culturing of at least one day. Culturing in contact with the antigen-presenting synthetic surface may be performed for a period from about four days to about seven days.

In some variations, the activated T cell may be CD45RO+. In some variations, the activated T cell is CD28 positive.

In some variations, an area of the antigen-presenting functionalized region may be less than about 25%, less than about 15%, less than about 10%, less than about 5%, or less than about 2% of the area of a bottom surface of a well of the well plate.

In another aspect, a method of activating a lymphocyte is provided, the method including contacting a plurality of lymphocytes with an activating moiety-presenting covalently functionalized region of a surface of a well plate, where the activating moiety-presenting covalently functionalized region includes a plurality of primary activating molecular ligands linked to the surface; and a plurality of co-activating molecular ligands linked to the surface; and culturing the plurality of lymphocytes, thereby converting at least a portion of the plurality of lymphocytes to activated lymphocytes. The lymphocytes may include B cells, T cells or NK cells.

The activating moiety-presenting covalently functionalized region may be a first region of a surface of a well plate like any well plate including an activating moiety-presenting covalently functionalized region as described herein. The well plate including the activating moiety-presenting covalently functionalized region of the surface may be produced by any method of producing a well plate having a surface including a lymphocyte-activating covalently functionalized region as described herein.

In some variations, the primary activating molecular ligands may include a CD3 binding molecule or an MHC molecule. In some embodiments, the plurality of MHC molecules may each include an MHC Class I protein sequence and a beta microglobulin protein sequence. The MHC molecule may further include an antigenic peptide. In some variations, the CD3 binding protein may be an antibody or a fragment thereof that retains binding affinity.

In some variations, the plurality of co-activating molecular ligands may include TCR co-activating molecules and adjunct TCR activating molecules. In some variations, the plurality of co-activating molecular ligands may include a CD2 binding molecule and/or a CD28 binding molecule. In some variations, where more than one type of co-activating molecular ligands are present, the ratio of differing co-activating molecular ligands may be about 20:1 to about 1:20 or about 3:1 to about 1:3.

In some variations, the plurality of specifically bound primary activating molecular ligands may have a density of at least about $1\times10^2$ molecules per square micron or from about $1\times10^2$ to about $1\times10^5$ molecules per square micron in the activating moiety-presenting covalently functionalized region of the surface. In some variations, the plurality of specifically bound co-activating molecular ligands may have a density from about $1\times10^2$ to about $1\times10^5$ molecules per square micron or about $1\times10^3$ to about $1\times10^5$ molecules per square micron in the activating moiety-presenting covalently functionalized region of the surface. A ratio of the primary activating molecular ligands to the co-activating molecular ligands in the activating moiety-presenting covalently functionalized region is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

In some variations, an area of the activating moiety-presenting functionalized region may be less than about 25%, less than about 15%, less than about 10%, less than about 5%, or less than about 2% of an area of a bottom surface of a well of the well plate.

In another aspect, a kit for preparing a well plate including a surface having an activating moiety-presenting covalently functionalized region is provided, where the kit includes a well plate including a surface including a reactive moiety-presenting covalently functionalized region, where the reactive moiety is an azido moiety, a biotin moiety or a streptavidin moiety. The kit may include an activating reagent. In some variations, the kit may further include a surface functionalization reagent. In some variations, the well plate including the surface having an activating moiety-presenting covalently functionalized region may be any well plate having an azido-presenting, biotin-presenting or streptavidin presenting covalently functionalized region as described herein.

In some variations, the kit may include the surface functionalization reagent, where the surface functionalization reagent may be a biotin containing reagent or a streptavidin containing reagent configured to react with the reactive moiety. In some embodiments, the kit may further include both the biotin containing reagent and the streptavidin containing reagent.

In some variations, the activating reagent may include a primary activating reagent including a plurality of major histocompatibility complex (MHC) molecules (e.g., Class I or Class II) configured to bind with a T cell receptor of the T cell, and configured to bind to a binding site of streptavidin or a plurality of CD3 binding molecules.

In some variations, the kit may further include a co-activating reagent including a plurality of co-activating molecules, each configured to bind a binding site of streptavidin, and where each of the co-activating molecules includes a CD2 binding molecule or a CD28 binding molecule.

BRIEF DESCRIPTION OF THE DRAWINGS

FIGS. 7A to 7D are graphical representations of cell population characteristics of T cells activated according to some embodiments of the disclosure.

DETAILED DESCRIPTION OF THE INVENTION

Figure 1A:
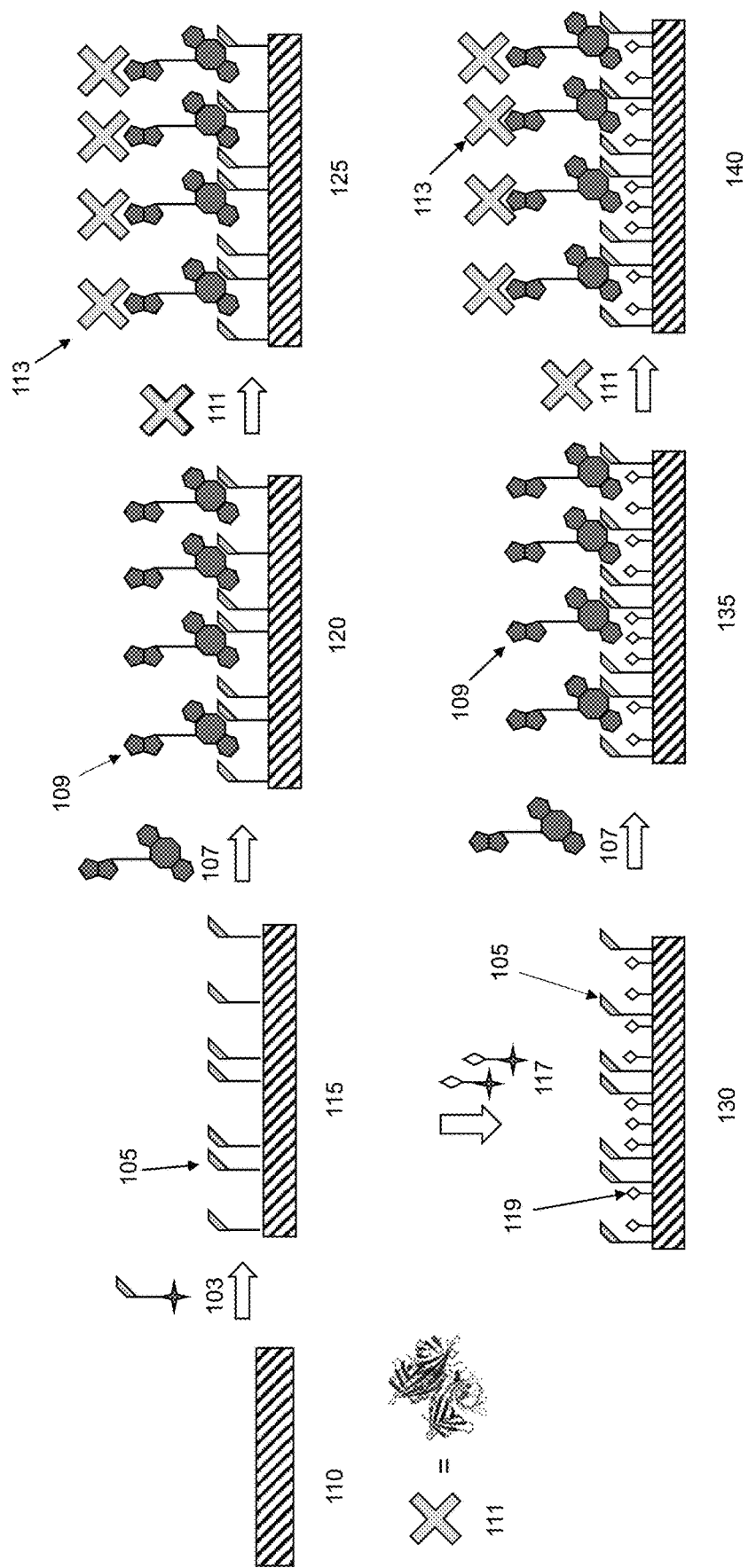
FIGS. 1A to 1C are schematic representations of alternative routes for introduction of streptavidin binding moieties to the surface of wells in an azido-functionalized well plate according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. The term "or" is used in an inclusive sense, i.e., equivalent to "and/or," unless the context dictates otherwise. It is noted that, as used in this specification and the appended claims, the singular forms "a," "an," and "the," and any singular use of any word, include plural referents unless expressly and unequivocally limited to one referent. As used herein, the terms "comprise," "include," and grammatical variants thereof are intended to be non-limiting, such that recitation of items in a list is not to the exclusion of other like items that can be substituted or added to the listed items. Section divisions in the specification are for ease of review only and do not limit any combination of elements discussed. In case of any contradiction or conflict between material incorporated by reference and the expressly described content provided herein, the expressly described content controls.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axially-axial area.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one. As used herein, the term "plurality" can be 2, 3, 4, 5, 6, 7, 8, 9, 10, or more.

As used herein, the term "plurality" can be 2, 3, 4, 5, 6, 7, 8, 9, 10, or more.

As used herein, the term "disposed" encompasses within its meaning "located."

Whether represented as square micron, mm², or mm2, all of these notations refer to the same measure of an area having dimensions of micron×micron.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

As used herein, "synthetic surface" refers to an interface between a support structure and a gaseous/liquid medium, where the synthetic surface is prepared by non-biological processes. The synthetic surface may have biologically derived materials connected to it, e.g., primary and co-activating molecules as described herein, to provide an antigen-presenting synthetic surface, provided that the synthetic surface is not expressed by a biological organism. Typically, the support structure is solid, such as the non-surface exposed portions of a bead, a wafer, or a substrate, cover or circuit material of a microfluidic device and does not enclose a biological nucleus or organelle.

As used herein, a "well plate" is a device used to culture biological cells. A well plate can include a plurality of wells (e.g., 2, 6, 12, 24, 96, 384, or any number of wells therebetween). Alternatively, a well plate can include a single well, and thus the term "well plate" can encompasses traditional culture plates (e.g., round culture plates) and culture flasks. The well plate may include a cover or a cap which is suitable for covering or capping one or more wells of the well plate.

As used herein, "streptavidin" generally refers to any protein which binds to biotin with high affinity and shares structural and/or protein sequence homology with the streptavidin protein originally isolated from the bacterium *Streptomyces avidinii*. As such, the term "streptavidin" encompasses mutated versions and/or fragments of *Streptomyces avidinii* streptavidin that retain binding to biotin, and biotin-binding mutated versions and/or fragments of proteins homologous to *Streptomyces avidinii* streptavidin (e.g., avidin) that retain binding to biotin. Streptavidin is typically tetrameric in structure, but the term "streptavidin" encompasses non-tetrameric forms as well.

As used herein, "co-activating" refers to a binding interaction between a biological macromolecule, fragment thereof, or synthetic or modified version thereof and a T cell (other than the primary T cell receptor/antigen:MHC binding interaction) that enhances a productive immune response to produce activation of the T cell. Co-activating interactions are antigen-nonspecific interactions, e.g., between a T-cell surface protein able to engage in intracellular signaling such as CD28, CD2, ICOS, etc., and an agonist thereof. "Coactivation" and "co-activating" as used herein is equivalent to the terms co-stimulation and co-stimulating, respectively.

Figure 2:
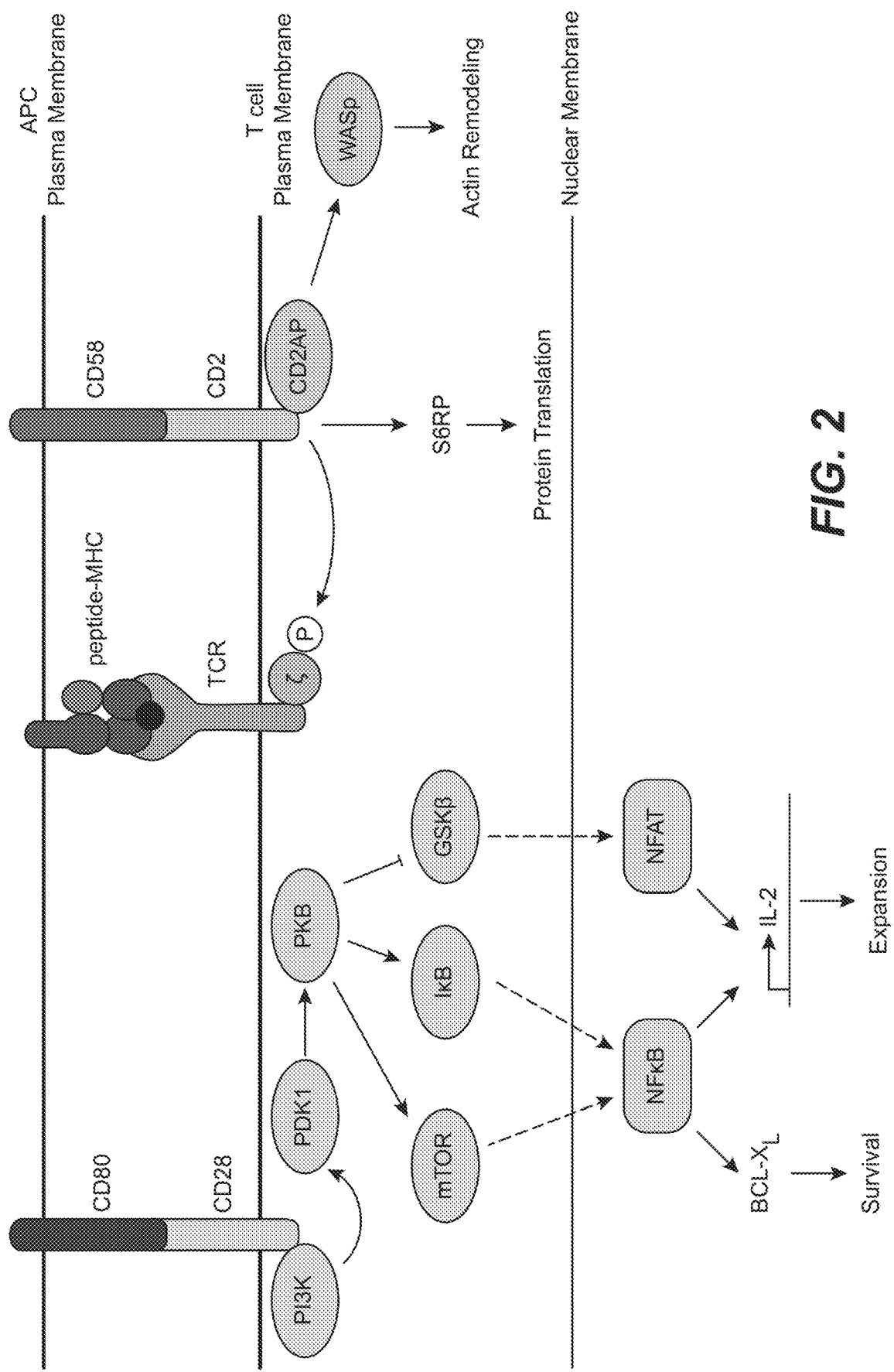
FIG. 2 is a schematic representation of activation pathways for T cell activation according to some embodiments of the disclosure.

As used herein, a "TCR co-activating molecule" is a biological macromolecule, fragment thereof, or synthetic or modified version thereof that binds to one or more co-receptors on a T Cell that activate distal signaling molecules which amplify and/or complete the response instigated by antigen specific binding of the TCR. In one example, signaling molecules such as transcription factors Nuclear Factor kappa B (NF kB) and Nuclear factor of activated T cells (NFAT) are activated by the TCR co-activating molecule. The TCR co-activating molecule can be, for example, an agonist of the CD28 receptor, which signals through the phosphoinositide 3 kinase (PI3K)/Akt pathway. See FIG. 2.

As used herein, "CD28high" or "CD28(High)" refers to a phenotype of high CD28 surface expression in a T cell. Those skilled in the art are familiar with the CD28high phenotype and appropriate ways of identifying CD28high T cells. Unless otherwise indicated, CD28high T cells include T cells that meet any of the following criteria. In some claims, a CD28high T cell is a T cell that expresses higher levels of CD28 than a resting CD8+ T cell. A CD28high T cell may also express higher levels of CD28 than an irrelevant non-antigen specific T cell. In some claims, CD28high T cells are a population in which the level of surface CD28 which can be measured by FACS is equal to or greater than the level of surface CD28 present on circulating memory T cells which can be measured by FACS. In some claims, a CD28high T cell has a level of surface CD28 equal to or greater than the level of surface CD28 present on circulating memory T cells from the same sample or individual. Expression of surface CD28 can be determined by FACS and the mean (e.g., geometric mean) or median level of surface CD28 present on circulating memory T cells can be used for determining whether a given T cell is CD28high. In some claims, a CD28high T cell is a T cell that expresses CD28 at a significantly higher level than expression typical of naïve CD8 T cells from the same sample or individual, e.g., higher than 75%, 80%, 85%, 87.5%, 90%, 92.5%, or 95% of the naïve T cells. Naïve CD8 T cells can be identified and characterized by known methods, e.g., flow cytometrically, as CD8+ cells expressing detectable CD28 and minimal or no CD45RO.

As used herein, a "TCR adjunct activating molecule" stimulates classes of signaling molecules which amplify the antigen-specific TCR interaction and are distinct from the TCR co-activating molecules. For example, TCR proximal signaling by phosphorylation of the TCR proximal signaling complex is one route by which TCR adjunct activating molecules can act. The TCR adjunct activating molecule may be, for example, an agonist of the CD2 receptor. See FIG. 2.

As used herein, an "activated T cell" is a T cell that has experienced antigen (or a descendant thereof) and is capable of mounting an antigen-specific response to that antigen. Activated T cells are generally positive for at least one of CD28, CD45RO, CD127, and CD197.

As used herein, "antibody" refers to an immunoglobulin (Ig) and includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof.

Immunotherapy for cancer is a promising development, but in some embodiments, requires specifically activated T lymphocytes which are compatible with the subject of the therapy. However, the current use of antigen presenting dendritic cells to activate T lymphocytes presents several disadvantageous aspects. Dendritic cells must be obtained from donor sources, limiting throughput. Dendritic cells must be matured for each sequence of T lymphocyte activation, which requires a lead time of about 7 days. Irradiation of dendritic cells is also required, which limits where such processing can be performed.

Replacing the use of autologous antigen presenting dendritic cells with antigen presenting synthetic surfaces within one or more wells of a well plate for activating T lymphocytes may afford greater reproducibility to stimulate and expand T lymphocytes for a therapeutically relevant population. Antigen presenting synthetic surfaces of a well plate may be engineered for antigen-specific activation of T lymphocytes, providing more controllable and/or characterizable and/or reproducible and/or more rapid development of populations of activated T lymphocytes having desirable phenotypes for treatment of cancer. Antigen-presenting synthetic surfaces of one or more wells of a well plate can also allow for more control and selectivity over T cell activation, including more precise targeting of desired T cell phenotypes following activation, e.g., enrichment of particular forms of memory T cells. Furthermore, antigen-presenting synthetic surfaces of one or more wells of a well plate can also exploit economies of scale and/or provide reproducibility to a greater degree than using autologous antigen presenting dendritic cells. As such, this technology can make cellular therapies available to patients in need thereof in greater numbers and/or in less time. Providing T cells useful for cellular therapies more rapidly can be especially important for patients with advanced disease. The structure of such antigen-presenting synthetic surfaces of one or more wells of a well plate and their methods of preparation and use are described herein. In some embodiments, the antigen-presenting synthetic surfaces of one or more wells of a well plate comprise primary activating ligands in combination with TCR co-activating molecules and/or adjunct TCR activating molecules, which together serve to activate T cells. Surface density ranges for these components and ratios of one to another that can further improve efficacy are also disclosed herein. In some embodiments, the antigen-presenting synthetic surfaces of one or more wells of a well plate and their methods of preparation and use provide one or more of the foregoing advantages.

Further, lymphocytes other than T lymphocytes may be activated by contact with an appropriately prepared lymphocyte activating covalently-functionalized surfaces within a well plate as described herein. B lymphocytes and NK cells may be activated and/or expanded using the activating surfaces of the well plates described herein for any purpose, including immunotherapies and cell production generally.

In order to provide lymphocyte activating synthetic surfaces within a well of a well plate, controllably covalently functionalized well plates having a defined region for such activation have been discovered by Applicant and are described.

Accordingly, a well plate is provided, including a surface having a first region which is a reactive moiety-presenting covalently functionalized region or an activating moiety-presenting covalently functionalized region, where the reactive moiety is an azido moiety, a biotin moiety or a streptavidin moiety and the activating moiety is a lymphocyte-activating moiety. The first region may have an area of at least 0.5 mm² (e.g., at least 0.6 mm², at least 0.7 mm², at least 0.8 mm², at least 0.9 mm², at least 1.0 mm², at least 1.1 mm², at least 1.2 mm², at least 1.3 mm², at least 1.4 mm², at least 1.5 mm², at least 1.6 mm², at least 1.7 mm², at least 1.8 mm², at least 1.9 mm², at least 2.0 mm², at least 2.5 mm², at least 3.0 mm², at least 35 mm², at least 4.0 mm², at least 4.5 mm², at least 5.0 mm², at least 6.0 mm², at least 7.0 mm², at least 8.0 mm², at least 9.0 mm², at least 10 mm², at least 15 mm², at least 20 mm², at least 25 mm², at least 30 mm², at least 35 mm², at least 40 mm², at least 45 mm², at least 50 mm², at least 75 mm², at least 100 mm², at least 150 mm², at least 200 mm², at least 250 mm², at least 300 mm², at least 400 mm², at least 500 mm², at least 600 mm², at least 700 mm², at least 800 mm², at least 900 mm², at least 1000 mm², or more). In some embodiment, such as those in which the reactive moiety being presented is a biotin moiety or a streptavidin moiety or the first region is an activating moiety-presenting covalently functionalized region, the first region will typically have an area that is less than 100 mm², less than 75 mm², or less than 50 mm². In other embodiments, such as those in which the reactive moiety is an azido moiety, the first region may have an area that exceeds 1000 mm², e.g., the first region may have an area of at least 2,000 mm², at least 3,000 mm², at least 4,000 mm², at least 5,000 mm², at least 6,000 mm², at least 7,000 mm², at least 8,000 mm², at least 9,000 mm², at least 10,000 mm², 20,000 mm², at least 30,000 mm², at least 40,000 mm², at least 50,000 mm², at least 60,000 mm², at least 70,000 mm², at least 80,000 mm², at least 90,000 mm², at least 100,000 mm², or more (e.g., substantially all of the inner surface of a well, or each of two or more wells, of the well plate). In some variations, the first region may have a dimension of about 0.5 mm to about 4.0 mm (e.g., about 1.0 mm to about 35 mm, or about 1.5 mm to about 3.0 mm). The first region may be substantially circular and have a diameter of about 0.5 mm to about 4.0 mm (e.g., about 1 mm to about 35 mm, or about 1.5 mm to about 3.0 mm).

The surface of the well plate may further include a second region which is a covalently modified region including surface blocking ligands. Optionally, the second region may surround the first region. In some embodiments, each of the surface blocking ligands may include a hydrophilic or negatively charged moiety (e.g., a carboxylate group). In some embodiments, each of the surface blocking ligands may include polyethylene glycol (PEG) moieties The surface of the well plate may include glass or polystyrene. In some variations, the surface of the well plate may include polypropylene, polycarbonate, polyethylene, cycloolefin copolymer, or melamine.

The first region may have a density of respective reactive moieties or activating moieties of at least 50/um², e.g. from about 50 reactive moieties or activating moieties/um² to about $8\times10^5$/um², about $1\times10^2$/um² to about $8\times10^5$/um²; about 50/um² to about $5\times10^5$/um²; about $1\times10^2$/um² to about $1\times10^5$/um²; about 50/um² to about $5\times10^4$/um²; about $1\times10^2$/um² to about $1\times10^4$/um²; about $1\times10^2$/um² to about $5\times10^3$/um²; about $1\times10^2$/um² to about $1\times10^3$/um²; about 50/um² to about $5\times10^2$/um²; about 50/um² to about $1\times10^2$/um²; or any value therebetween for the number of reactive moieties or activating moieties/um². The first region including respective reactive moieties or activating moieties may be linked covalently to the surface via a linker having from 5 to about 20 backbone atoms, about 10 to about 40 backbone atoms, about 15 to about 50 backbone atoms, or more than 50 backbone atoms, where the backbone atoms are selected from carbon, silicon, nitrogen and oxygen. Thus, e.g., the reactive moieties or activing moieties may be linked covalently to the surface through a series of about 5, 7, 9, 10, 11, 13, 15, 20, 25, 30, 35, 40, 45, 50, 55, 60, 65, 70, 75, 80, 90, 100, 200 bond lengths of a linker or any number of bond lengths therebetween.

In some variations, the reactive moiety may be streptavidin, and the streptavidin functionality is covalently attached to the first region of the surface of the well plate. In other variations, the reactive moiety may be streptavidin, and the streptavidin functionality is non-covalently attached to a biotin moiety which is itself covalently attached to the first region of the surface of the well plate.

In some variations, the first region may be an activating moiety-presenting covalently functionalized region including a plurality of specifically bound primary activating molecular ligands and a plurality of specifically bound co-activating molecular ligands. A ratio of the primary activating molecular ligands to the co-activating molecular ligands on the first region of the surface is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

In some embodiments, each ligand of the plurality of specifically bound primary activating molecular ligands may include a major histocompatibility complex (MHC) molecule (e.g., Class I or Class II) configured to bind to a T cell receptor (TCR) of a T cell. The MHC molecule may include an MHC Class I protein sequence and a beta microglobulin protein sequence. In some variations, the MHC molecule may be connected to the activating moiety-presenting covalently functionalized region via a C-terminal linkage.

The MHC molecule may further include an antigenic peptide. The antigenic peptide may be a tumor-associated antigen, a viral antigen, a bacterial antigen, a fungal antigen, or a protozoan antigen. In some variations, the antigenic peptide may be a tumor-associated antigen. In some embodiments, the tumor-associated antigen may be SLC45A2, TCL1, VCX3A, MART1 or NYESO1.

In some variations, each ligand of the plurality of specifically bound co-activating molecular ligands may include a T cell receptor (TCR) co-activating molecule or an adjunct TCR activating molecule. A ratio of the TCR co-activating molecules to the adjunct TCR activating molecules of the plurality of co-activating molecular ligands is about 100:1 to about 1:100. In some embodiments, the ratio of the TCR co-activating molecules to the adjunct TCR activating molecules of the plurality of co-activating molecular ligands may be 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, where each of the foregoing values is modified by "about". In other embodiments, the ratio of the TCR co-activating molecules to the adjunct TCR activating molecules of the plurality of specifically bound co-activating molecular ligands may be from about 20:1 to about 1:20 or about 3:1 to about 1:3.

In some variations, the TCR co-activating molecules may include a CD28 binding protein, or a fragment thereof, which retains binding ability to CD28. In some embodiments, the CD28 binding protein or the fragment thereof may further include a site-specific C-terminal biotin moiety. In some embodiments, the TCR co-activating molecules may include a CD80 molecule or a fragment thereof, where the fragment retains binding activity to CD28. In some other embodiments, the TCR co-activating molecules may include an anti-CD28 antibody or a fragment thereof, where the fragment retains binding activity to CD28.

In some variations, the adjunct TCR activating molecule may include a CD2 binding protein, or a fragment thereof, which retains binding activity to CD2. In some embodiments, the CD2 binding protein or the fragment thereof further includes a site-specific C-terminal biotin moiety. In some embodiments, the adjunct TCR activating molecule may include a CD58 molecule or fragment thereof, where the fragment retains binding activity with CD2. In some other embodiments, the adjunct TCR activating molecule may include an anti-CD2 antibody or a fragment thereof, where the fragment retains binding activity with CD2.

In some variations, the plurality of specifically bound primary activating molecular ligands and the plurality of specifically bound co-activating molecular ligands may be specifically bound to streptavidin functionalities of a streptavidin-presenting first region of the well plate.

The plurality of specifically bound primary activating molecular ligands may have a density of at least about $1\times10^2$ molecules per square micron in the first region, and optionally, a density of about $1\times10^2$ to about $1\times10^5$ molecules per square micron in the first region. The plurality of specifically bound co-activating molecular ligands has a density of at least $1\times10^2$ molecules per square micron or about $1\times10^3$ to about $1\times10^5$ molecules per square micron in the first region.

In some variations, a well plate is provided, where each of one or more wells of the well plate includes the surface and the first region thereof, where the first region is a reactive moiety-presenting covalently functionalized region or an activating moiety-presenting covalently functionalized region like any well plate having the surface and first region as described herein. The first region of each of the one or more wells may be located on a bottom surface of the corresponding well(s). An area of each first region may be less than about 50%, less than about 25%, less than about 15%, less than about 10%, less than about 5%, or less than about 2% of the area of the bottom surface of the corresponding well(s). In some embodiments, when the area of the first region is less than the whole area of the bottom surface of the well(s), then the reactive-moiety is not an azido-moiety. In some embodiments, each of the surface blocking ligands may include a hydrophilic or negatively charged moiety. In some embodiments, the surface blocking ligands may include polyethylene glycol (PEG) moieties.

As described above, a well plate having a surface including a reactive moiety-presenting covalently functionalized region, e.g., azido-presenting or alkynyl-presenting moiety, may be used as a centrally accessible functionalized form, which may be modified in many different ways to with a wide variety of covalent ligand partner molecules for a myriad of biological and chemical transformations of micro-objects of various classes including, but not limited to biological cells and fragments thereof and used in methods, including but not limited to the methods described herein, for activating lymphocyte cells to obtain desired populations having controllable, selected phenotypes. As used herein, azido-presenting refers to a covalently functionalized region of the surface having ligands covalently attached thereto, where the ligands have azido functional groups at or near a first terminus of the ligand opposite from a surface-bound second terminus of the ligand. The azido groups at or near the terminus opposite from the surface bound terminus are substantially available for reaction with reaction pair moieties with which an azido group may react, such as, but not limited to an alkyne, cyclic strained alkyne, alpha keto chlorides, and the like. A covalently functionalized surface as referred to herein includes any kind of glass or polymer surface to which covalently linked molecules (e.g., ligands) have been coupled, as described in detail below. The region of the surface that is covalently functionalized may be the entire surface, a portion of the surface or a selected portion of the surface, as described more fully below.

Other useful controllably covalently functionalized well plates have also been discovered by Applicant and described herein. Biotin or streptavidin may be introduced to the azido-presenting covalently functionalized surface of the well plate, in particular within one or more wells of the well plates, producing biotin-presenting covalently functionalized region(s) of a surface of a well plate or streptavidin-presenting covalently functionalized region(s) of a surface of a well plate. In one arrangement, the streptavidin is itself covalently linked to the surface of the well plate via a linker including a reactive group that is configured to react with the azido functionality of the azido-presenting covalently functionalized surface of the well plate. In another arrangement, the streptavidin moiety is non-covalently attached to a biotin moiety, where the biotin moiety is itself covalently linked to the surface via a linker including a reactive group configured to react with the azido functionality of the azido-presenting functionalized surface of the well plate. In either case, a streptavidin-presenting covalently functionalized region is introduced to the surface, where the streptavidin moieties, similarly to the azido moieties, are covalently linked to the surface such that at least one of the binding sites of streptavidin is available for binding with biomolecular ligands for use in the methods of activating lymphocytes as described herein.

A streptavidin-presenting covalently functionalized region of a surface of a well plate may be used for a wide variety of applications, but one important, but nonlimiting, use is for activation of lymphocytes, including but not limited to antigen-specific activation of T cells. Applicant has discovered that the ability to limit the density of streptavidin ligands present within a well of a well plate and/or ability to limit the size of the region that presents streptavidin ligands and/or select the location of the region that presents streptavidin ligands can be important for effective and efficient activation of T cells. Without wishing to be bound by theory, a high density of streptavidin moieties present on a functionalized surface of a well of a well plate can permit a high concentration of MHC complexes, presenting the antigen, and co-stimulatory ligands to bind to the multiple binding sites available on each streptavidin, providing a highly stimulatory antigen-presenting synthetic surface. This highly stimulatory antigen-presenting synthetic surface may actually overstimulate T cells, pushing the overactivated cells towards exhausted or morbid phenotypes, and providing a lower number of antigen specific cells that are physiologically able to be expanded to an effective cell product. Alternatively, or in addition, a well having a large region of primary and secondary (or co-activating) activating ligands may also over-stimulate lymphocytes as well, and lead to activated lymphocytes with undesirable phenotypes, such as exhausted T cells, and the like. Restricting the area of lymphocyte activating ligands to a smaller region of a well of a wellplate may advantageously provide areas to which lymphocytes may migrate, thereby preventing morbid phenotype production. Additionally, with the restricted activating regions used in the well plates described herein, it may be useful in some embodiments, to use round bottomed wells, to employ gravity to bring cells to the activating region(s) within the well.

Similarly, a well having a large region or non-controlled surface area such as the entire bottom or cell-containing region of the well modified to present one or more activating species such as cell surface markers such as CD2, CD4, CD8, CD28 and the like, antigen-presenting species such as a peptide loaded MHC molecule, cytokines, cell adhesion ligands and growth stimulatory molecules, may induce overly activating contact with the cell to be activated and, in some embodiments, expanded, which may lead to down regulation of desired cell surface markers and other internal signaling pathways, again leading to undesirable cell populations such as, but not limited to, exhausted or non-expanding activated T cells.

Therefore, Applicants describe functionalized well plates having controllable, defined and limited contact regions and contact densities of streptavidin moieties within specified regions of a well within the functionalized well plate. These limited regions/concentrations of streptavidin moieties may then be used to introduce the activating species for effective and efficient activation of lymphocytes, which can include, but are not limited to, T cells having antigen specificity and desirable phenotype for a cellular product for use in immunotherapy of an individual. It is proposed that by limiting the area of the region having activating ligands present that cells can move away from the activating region after receiving the stimulatory signals, maintaining the stimulation, without over activation. Additionally, surface blocking ligands, which do not themselves permit attachment of activating molecular species, may be used to either limit the density or physical location of the streptavidin functionalities (and hence, activating ligands introduced thereto) and provide supporting surface modification conducive to cell maintenance, expansion and portability, without adding to stimulatory signaling. The specific and controllable introduction of restricted regions for activation of a surface of a well plate is described more fully below.

Figure 1B:
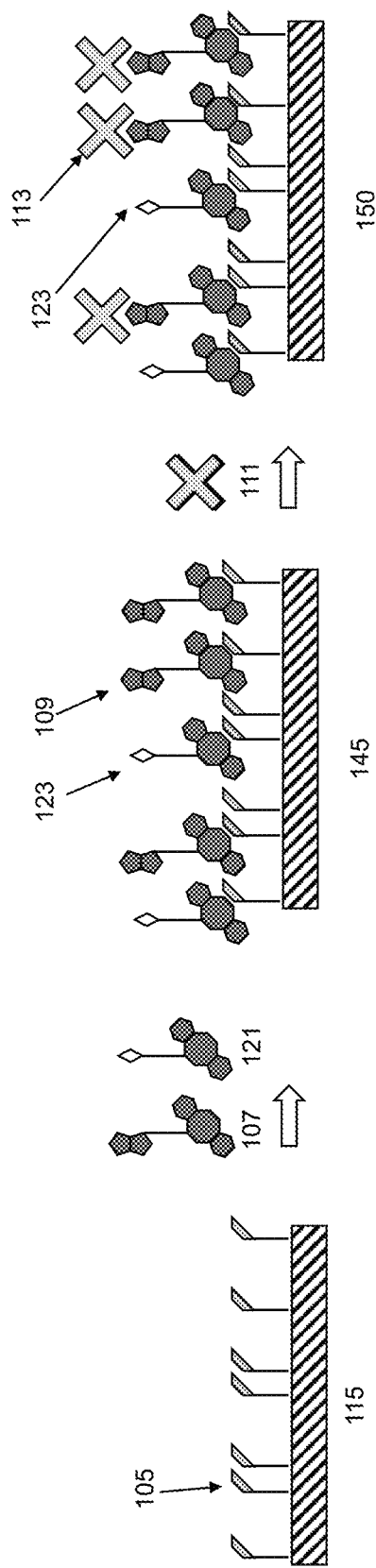
Figure 1C:
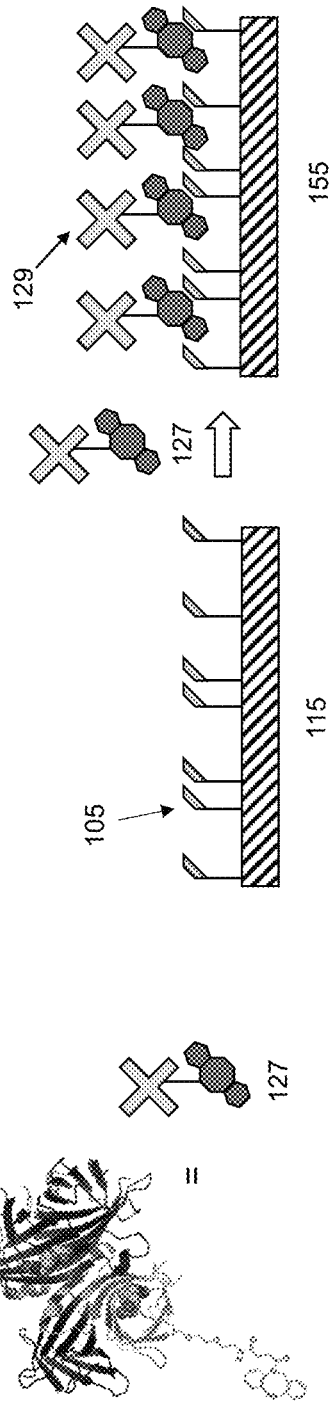

The controllable and flexible introduction of covalently functionalized regions of a surface within a well plate can be understood by reviewing FIGS. 1A to 1C and the accompanying description. As shown in FIG. 1A, a well plate 110 is provided. The well plate may be a glass or polymer, e.g., a plastic polymer, or may comprise a glass or polymer surface. The well plate 110 well plate may comprise, consist of, or consist essentially of glass, polystyrene, polypropylene, polycarbonate, polyethylene, cycloolefin copolymer or melamine e polystyrene, polypropylene, polycarbonate, cycloolefin copolymer, melamine, and the like. The well plate 110 may have 16, 48, 96, 384 or more wells within the well plate. The well plate 110 may be treated or cleaned prior to functionalization in order to remove impurities and to introduce a plurality of reactive functionalities at the surface. The treatment/cleaning may include plasma cleaning, which may be performed as described herein or in any suitable variation of plasma cleaning as is known in the art. Alternatively, or in addition, the surface of the well plate 110 may be treated with piranha solution to achieve similar introduction of reactive functionalities, such as oxide, on the surface of the well plate.

The well plate 110, which may be treated or cleaned, may be reacted with a reagent 103, which provides synthetically accessible handles including reactive moieties at the surface of the well plate for further elaboration. A generally useful reactive moiety that may be easily introduced includes, but is not limited to azide or alkyne, each of which can be further reacted with reagents classed within the group of Click chemistry reagents to provide a wide variety of surface modifications to the well plate surfaces. However, other chemical couplings as are known in the art, e.g., Suzuki borane-type coupling reactions, Michael reactions, and the like, may also be used to couple a surface functionalization reagent or a surface blocking reagent to a suitably reactive surface, and other reactive moieties such as carbonyls, conjugated carbonyls, and other activated moieties may be used. The disclosure is not limited to the use of Click chemistry and respective reagent pairs to introduce the modified surfaces and activating species supported thereupon, but introduction of azido moieties are described in detail herein for simplicity.

Further examples of chemistry performed either on internal surfaces of microfluidic devices or on surfaces of beads, such as glass or polymeric beads, which can be applied to modification of the wells of well plates are described in PCT/US2017/034832, filed May 26, 2017 (Lowe et al.) and PCT/US2018/043146, filed on Jul. 20, 2018 (Beemiller, et al.), each of which disclosures are herein incorporated by reference in its entirety.

One very useful class of reagents 103 for initial functionalization of the surface include azido-substituted trialkoxysiloxanes, where trialkoxysiloxane reacts with the surface exposed moieties (e.g., oxide) of the cleaned surface of well plate 110. The siloxane may have a linker linking the azido reactive moiety to the siloxane, which includes a hydrocarbon, substituted hydrocarbon or an alkylene oxide chain. The reaction may be performed in solution or under gaseous conditions, and in some variations, reaction of the azido-substituted trialkoxysiloxane is performed under vacuum with volatilized azido-substituted trialkoxysiloxane. The choice of the specific azido-trialkoxysiloxane depends on the material of the well plate as differing polymeric well plates are resistant to differing elevated temperatures. The length of the linker determines what the temperature must be used to volatilize the azido-trialkoxysiloxane, and has an effect on the nature of the modified reactive surface introduced. The introduction of the azido-substituted ligands to the surface by reaction of the trialkoxysiloxane portion of the molecule with surface exposed moieties on the well plate surface, such as oxide moieties. The reaction may be performed in solution, or may be performed under conditions where the azido-substituted trialkoxysiloxane is volatilized to react with the surface exposed moieties. The area of the well plate reacting with the azido-substituted trialkoxysiloxane may be the entire well plate, may be masked to limit reaction to a portion of the well plates (e.g., masked such that only one or more wells of the well plate may react) or any variation thereof. In some other embodiments, only a region of a bottom of a well (or more wells) of a well plate may be an azido-presenting covalently functionalized region of the well plate. As referred to herein, a bottom surface is located on a wall of an enclosure forming the well, where the bottom surface is disposed opposite the opening at the top of the well in the well plate. In some embodiments, the azido-presenting covalently functionalized region is not located on a side wall of the enclosure forming the well, where the side wall is adjacent to the opening of the well in the well plate. In some other embodiments, the azido-presenting covalently functionalized region is not located on a side wall of the enclosure forming the well, where the side wall is substantially perpendicular to the opening at the top of the well.

In some variations, the azido-presenting covalently functionalized region may have an area of at least 0.5 mm$^2$ (e.g., at least 1.0 mm$^2$, at least 1.5 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, at least 50 mm$^2$, at least 75 mm$^2$, at least 100 mm$^2$, at least 150 mm$^2$, at least 200 mm$^2$, at least 250 mm$^2$, at least 300 mm$^2$, at least 400 mm$^2$, at least 500 mm$^2$, at least 600 mm$^2$, at least 700 mm$^2$, at least 800 mm$^2$, at least 900 mm$^2$, at least 1,000 mm$^2$, at least 2,000 mm$^2$, at least 3,000 mm$^2$, at least 4,000 mm$^2$, at least 5,000 mm$^2$, at least 6,000 mm$^2$, at least 7,000 mm$^2$, at least 8,000 mm$^2$, at least 9,000 mm$^2$, at least 10,000 mm$^2$, at least 20,000 mm$^2$, at least 30,000 mm$^2$, at least 40,000 mm$^2$, at least 50,000 mm$^2$, at least 60,000 mm$^2$, at least 70,000 mm$^2$, at least 80,000 mm$^2$, at least 90,000 mm$^2$, at least 100,000 mm$^2$, or more).

The azido-presenting covalently functionalized region may have a density of azido groups of at least 50/um$^2$ (e.g., from about 50 azido groups/um$^2$ to about 2×10$^7$/um$^2$, about 1×10$^2$/um$^2$ to about 1×10$^7$/um$^2$; about 50/um$^2$ to about 5×10$^6$/um$^2$; about 1×10$^2$/um$^2$ to about 1×10$^6$/um$^2$; about 1×10$^2$/um$^2$ to about 5×10$^5$/um$^2$; about 1×10$^2$/um$^2$ to about 1×10$^5$/um$^2$; about 1×10$^2$/um$^2$ to about 5×10$^4$/um$^2$; about 50/um$^2$ to about 5×10$^4$/um$^2$; about 1×10$^2$/um$^2$ to about 5×10$^3$/um$^2$; about 50/um$^2$ to about 5×10$^2$/um$^2$; or any value therebetween for the number of azido groups/um$^2$).

The linker may have a length of bond lengths which may be 5, 7, 9, 10, 11, 13, 15, 20, 25, 30, 35, 40, 45, 50, 55, 60, 65, 70, 75, 80, 90, 100, 200 bond lengths, or any number of bond lengths therebetween. In some embodiments, the azido-presenting covalently functionalized region comprises azido functionalities linked covalently to the surface through a series of about 5 bond lengths to about 20 bond lengths or about 10 bond lengths to about 40 bond lengths. In some embodiments, the atoms of a linker linking the azido functionalities to the surface may be selected from carbon, silicon, nitrogen, sulfur, and oxygen. In some embodiments, the atoms of the linker may be selected from carbon, silicon, and oxygen. In some variations, the linker has from about seven to about seventeen backbone atoms, which may be selected from carbon, silicon, and oxygen. In some embodiments, the linker is a linear linker and the linker has only one first terminus attached to the azido moiety and one second terminus which is bound to the surface. In other embodiments, the linker is a branched linker and the branched linker may have one second terminus attached to the surface and a plurality of first termini, each attached to an azido moiety, e.g., an azido functionalized brush polymer. In various embodiments, the azido-presenting surface bound ligands of the surface form a monolayer on the surface of the well plate. In some embodiments, the azido-presenting surface bound ligands form a self-assembled monolayer, which may have a thickness from the surface of the well plate of about 10 angstroms, about 20 angstroms, about 30 angstroms, about 40 angstroms, about 50 angstrom, about 70 angstroms, to about 100 angstroms, or any value therebetween.

In some variations, the linker linking the azido moiety to the trialkoxysiloxane has a backbone length of about 20, about 18, about 16, about 14, about 12, about 10, about 9, about 8, about 7, about 6, about 5, or about 4 atoms long. In some embodiments, the backbone is about 7 atoms in length, and is a hydrocarbon chain. While glass well plates can generally tolerate considerably elevated reaction conditions, other polymeric well plates can deform or otherwise become unusable after exposure to greatly elevated temperatures. What has found to be effective to modify polymer well plates such as polystyrene or polycarbonate is use of an azido-substituted trialkoxysiloxane having a length of seven carbon atoms. As shown in FIG. 1A, the surface functionalizing reagent 103 may therefore be 7-azidoheptyl-trimethoxysilane, particularly for use with polymeric well plates, to produce a functionalized well plate 115, presenting functionalizing ligands 105 at the surface. In the specific case using 7-azidoheptyl-trimethoxysilane, the ligand 105 is an azidoheptyl ligand, covalently attached via a siloxane moiety to the surface.

Routes to provide a streptavidin-presenting covalently functionalized region(s) of a surface of a well plate. The covalently functionalized well plate surface 115 (in one specific example, azido-presenting covalently functionalized well plate surface) may be modified to present streptavidin moieties. This may be obtained in one of several ways.

Biotin-presenting covalently functionalized region(s) of a surface of a well plate. One approach to producing a streptavidin-presenting covalently functionalized region of a surface of a well plate is via a covalently bound biotin group to the surface of the well plate. Azido-functionalized well plate 115 may be reacted with a biotin linked-alkyne containing reagent such as a dicyclooctynyl containing Click reagent. In FIG. 1A, a dibenzocyclooctynyl (DBCO) Click reagent including biotin, DBCO reagent 107, as one example, may be used, where the biotin moiety is linked to the DBCO moiety by a linker including an alkyl, alkyleneoxide, or cleavable alkyl or alkyleneoxide backbone, amongst others. The linker may have a backbone length of at least 4 atoms, at least 8 atoms, at least 12 atoms, at least 16 atoms, at least 20 atoms, at least 50 atoms or at least 100 atoms, or more, which may be carbon, oxygen, nitrogen or sulfur. Reaction of the DBCO moiety of reagent 107 with the azido ligand 105 yields a covalently bound biotin-containing ligand 109 to yield a biotin-presenting covalently functionalized region of a surface of well plate 120.

In some variations of a biotin-presenting covalently functionalized region of a surface of a well plate, azido-functionalized surface of well plate 115 may be reacted first with a surface blocking reagent 117 to produce azido-presenting covalently functionalized region 130 of a surface of a well plate. Surface blocking reagent 117 may have a reactive moiety configured to react with remaining surface exposed moieties of the cleaned/prepared surface, which had not been bound with reagent 103 in the azido functionalization step. The surface blocking reagent 117 includes one reactive functionality such as a trialkoxysiloxane, configured to react with the surface exposed moieties introduced by cleaning. The surface blocking reagent 117, however, does not include a functionality configured to react with any of the biotin-containing reagents, streptavidin, streptavidin containing reagents, or lymphocyte activating reagents. The surface blocking reagent 117 may be like any suitable blocking reagent described more fully below.

Introduction of covalently bound biotin to surface 130 may be performed as for the reaction of surface 115 described above, with a DBCO-linked-biotin moiety 107, which reacts only with the azide functionalities of azide ligands 105 to yield biotin-presenting covalently modified region 135 of the surface of the well plate having covalently linked biotin ligands 109 and the surface blocking ligands 119.

In yet another alternative shown in FIG. 1B, the azido-presenting covalently functionalized surface of well plate 115 may be reacted with a mixture of the biotin-containing DBCO reagent 107 and a surface blocking DBCO reagent 121, having a surface blocking moiety and a DBCO moiety configured to react with azido moieties of surface 115. The surface blocking moiety which may be any suitable surface blocking DBCO reagent described more fully below. The product of this reaction is a biotin-presenting covalently modified region 145 of the surface of the well plate, having both biotin containing ligands 109 and surface blocking ligands 123. The proportions of the ligands on the mixed surface may be modified in any suitable proportion to "tune" the density of biotin moieties per unit area to a desired amount. The proportion of biotin ligands to surface blocking ligands may be about 3:1; about 2:1; about 1:1; about 1:2; about 1:3; about 1:4; about 1:5; about 1:6, about 1:8; about 1:10, or more. The chemical nature of the surface blocking moiety of the surface blocking ligands 123 may be varied as well to provide optimized surfaces for selected lymphocyte activations.

For biotin-presenting covalently functionalized regions 135, 145, the surface blocking reagent 117 and surface blocking DBCO reagent 121 may include more than one type of surface blocking moiety. For example, a mixture of reagents having differing chain length, charged moieties and/or hydrophilic character may be used.

A biotin-presenting covalently functionalized region 120, 135, 145 may have an area of at least 0.5 mm$^2$, e.g., at least 0.6 mm$^2$, at least 0.7 mm$^2$, at least 0.8 mm$^2$, at least 0.9 mm$^2$, at least 1.0 mm$^2$, at least 1.1 mm$^2$, at least 1.2 mm$^2$, at least 1.3 mm$^2$, at least 1.4 mm$^2$, at least 1.5 mm$^2$, at least 1.6 mm$^2$, at least 1.7 mm$^2$, at least 1.8 mm$^2$, at least 1.9 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, at least 50 mm$^2$, or any range defined by two of the foregoing end points. Thus, for example, the area of the biotin-presenting covalently functionalized region 120, 135, 145 may range from about 0.5 mm$^2$ to about 50 mm$^2$, about 1 mm$^2$ to about 40 mm$^2$, 2 mm$^2$ to about 35 mm$^2$, about 3 mm$^2$ to about 30 mm$^2$, or about 4 mm$^2$ to about 25 mm$^2$. Typically, the biotin-presenting covalently functionalized region 120, 135, 145 has an area equal to or less than 100 mm$^2$ (e.g., equal to or less than 75 mm$^2$, or equal to or less than 50 mm$^2$).

A biotin-presenting covalently functionalized region 120, 135, 145 may have a density of biotin functionalities of at least 50/um$^2$ (e.g., from about 50 biotin groups/um$^2$ to about 5×10$^6$/um$^2$, about 1×10$^2$/um$^2$ to about 1×10$^6$/um$^2$; about 1×10$^2$/um$^2$ to about 5×10$^5$/um$^2$; about 1×10$^2$/um$^2$ to about 1×10$^5$/um$^2$; about 1×10$^2$/um$^2$ to about 5×10$^4$/um$^2$; about 1×10$^2$/um$^2$ to about 1×10$^4$/um$^2$; about 1×10$^2$/um$^2$ to about 5×10$^3$/um$^2$; about 1×10$^2$/um$^2$ to about 1×10$^3$/um$^2$; about 50/um$^2$ to about 5×10$^2$/um$^2$; about 50/um$^2$ to about 1×10$^2$/um$^2$; or any value therebetween for the number of biotin groups/um$^2$).

The biotin-presenting covalently functionalized region comprises biotin functionalities linked covalently to the surface via a linker linked covalently to the surface through a series of about 5, 7, 9, 10, 11, 13, 15, 20, 25, 30, 35, 40, 45, 50, 55, 60, 65, 70, 75, 80, 90, 100, 200 bond lengths of a linker or any number of bond lengths therebetween. In some embodiments, the atoms of a linker linking the biotin functionalities to the surface may be selected from carbon, silicon, nitrogen, sulfur and oxygen. In some embodiments, the atoms of the linker are selected from carbon, silicon, and oxygen. In some embodiments, the linker linking the biotin to the DBCO moiety may have from about 10 to 40 backbone atoms selected from carbon, silicon, nitrogen and oxygen. In some embodiments, the linker is a linear linker and the linker has only one first terminus attached to the biotin moiety and one second terminus bound to the surface. In some embodiments, the linker is a substantially linear linker where the substantially linear linker may include, or be interrupted by a cyclic moiety such as a triazolyl or substituted triazolyl moiety. A cyclic moiety such as a triazolyl or substituted triazolyl group may be part of the substantially linear linker, introduced through a Click coupling to introduce the covalently bound biotin. In other embodiments, the linker is a branched linker and the branched linker may have one second terminus that is bound to the surface and a plurality of first termini each having a biotin moiety attached thereto, e.g., a biotin-presenting functionalized brush polymer, which may include cyclic groups such as triazolyl and/or substituted triazolyl groups. In some other embodiments, the linker linking the biotin moiety to the surface may further include a disulfide moiety or a photocleavable moiety. In various embodiments, the ligands of the biotin-presenting covalently functionalized surface form a monolayer on the surface of the region 120, 135, 145. In some embodiments, the biotin-presenting surface bound ligands form a self-assembled monolayer, which may have a thickness from the surface of the well plate of about 10 angstroms to about 100 angstroms, or any value therebetween.

The biotin-presenting covalently functionalized regions 120, 135, 145 of the surface of the wellplate may be further modified immediately or may be stored for later use. While FIGS. 1A, 1B shows biotin-presenting covalently functionalized regions 120, 135, 145 of the surface transformed further to a streptavidin-presenting covalently functionalized region of a surface of the well plate, the invention is not so limited. Any suitable binding pair to biotin may be bound to the biotin-presenting covalently functionalized region 120 of the surface of the well plate.

Streptavidin-presenting functionalized region(s) of a surface of a well plate. Any of biotin-presenting covalently functionalized regions 120, 135, 140 may couple streptavidin to the biotin moieties thereupon, as shown in FIGS. 1A and 1B. The streptavidin, which may be natural streptavidin or a modified streptavidin having binding affinity with biotin, having four binding sites, and shown schematically as structure 111, may then be reacted with the biotin containing ligand 109 of regions 120, 135, 145, binding at one of the four available sites of streptavidin, yielding respective streptavidin-presenting covalently functionalized regions 125, 140, 150, having streptavidin ligands 113. The streptavidin may be considered to be non-covalently bound itself, but is bound to the surface via biotin, which is itself covalently bound to the surface, thereby forming a streptavidin-presenting covalently functionalized region of a surface of a well plate. The strength of the biotin/streptavidin binding pair (the dissociation constant $K_d$ is about $10^{-14}$ mol/L) may be considered to be equivalent in strength to a covalent bond, thus permitting strong association to the surface.

As mentioned above, the streptavidin-presenting covalently functionalized region(s) 140, 150 include surface blocking ligands 119 and 123, respectively, permitting selective design of the activating surfaces Directly coupled Streptavidin to the azido-presenting covalently functionalized region of the surface. In yet a further alternative, shown in FIG. 1C, a streptavidin-presenting covalently functionalized region of the surface of the well plate may be produced directly from the azide-presenting covalently functionalized surface 115 having azido functionality ligands 105. Streptavidin may be covalently bound to the surface 115 in one step by reaction with a Click chemistry reagent having a streptavidin molecule covalently linked to an alkynyl moiety, such as reagent 127, where a DBCO moiety is linked covalently via a linker to a streptavidin tetrameric molecule (having four binding sites). The linker linking the DBCO to the streptavidin may be an alkenyloxide, alkyl or cleavable alkenyloxide or alkyl linear moiety. The linker may have from 10 to 50 backbone atoms selected from carbon, silicon, nitrogen and oxygen. (e.g., the streptavidin functionalities may be linked covalently to the surface through a series of about 5, 7, 9, 10, 11, 13, 15, 20, 25, 30, 35, 40, 45, 50, 55, 60, 65, 70, 75, 80, 90, 100, 200 bond lengths of a linker or any number of bond lengths therebetween. In some embodiments, the atoms of a linker linking the streptavidin functionalities to the surface may be selected from carbon, silicon, nitrogen, sulfur and oxygen. In some embodiments, the atoms of the linker are selected from carbon, silicon, and oxygen. In some embodiments, the linker is a linear linker and the linker has only one first terminus covalently attached to a streptavidin and one second terminus which is bound to the surface directly or indirectly. In some embodiments, the linker is a substantially linear linker and the linker has only one first terminus attached to a streptavidin moiety and one second terminus bound to the surface directly or indirectly, where the substantially linear linker may include, or be interrupted by a cyclic moiety such as a triazolyl or substituted triazolyl moiety. A cyclic moiety such as a triazolyl or substituted triazolyl group may be part of the substantially linear linker, introduced through a Click coupling to introduce the covalently bound streptavidin. In other embodiments, the linker is a branched linker and the branched linker may have one second terminus bound to the surface directly or indirectly and a plurality of first termini each bound to a streptavidin moiety, e.g., a streptavidin functionalized brush polymer, which may include cyclic groups such as triazolyl and/or substituted triazolyl groups. In other variations, streptavidin may be covalently attached to the surface at more than one point of the streptavidin molecule. In some other embodiments, the linker linking the streptavidin moiety to the surface may further include a disulfide moiety or a photocleavable moiety. In some embodiments, the streptavidin-presenting surface bound ligands form a layer having have a thickness from the surface of the well plate of about 10 angstroms to about 100 angstroms, or any value therebetween.

This one-step route as shown in FIG. 1C may also use a mixture of the streptavidin linked DBCO Click reagent 127 and surface blocking reagents like surface blocking reagents 121, where the surface blocking reagents may have any composition as described above. A mixture of streptavidin DBCO reagent 127 and surface blocking reagent 121 may be employed in any desired ratio to provide a selected density/distribution of streptavidin moieties on the modified surface 155 (mixture not shown). The proportion of streptavidin ligands to surface blocking ligands may be about 3:1; about 2:1; about 1:1; about 1:2; about 1:3; about 1:4; about 1:5; about 1:6, about 1:8; about 1:10, or more.

In yet another alternative, while the preceding exemplar has been discussed using DBCO Click reagents, all of the same surfaces may be introduced using non-cyclic alkyne-linked biotin, surface blocking reagents and streptavidin linked reagents in corresponding routes equivalent to those shown in FIGS. 1A-1C. In some variations, using alkyne-linked Click reagents to react with the azido ligands 105, with copper catalysis, may be helpful to slow the Click reaction sufficiently to obtain more precisely delimited regions of modification, as discussed in further detail below.

The streptavidin-presenting covalently functionalized region, like any described herein, may have a density of streptavidin functionalities of at least 50/um2, (e.g., from about 50 streptavidin groups/um$^2$ to about 8×10$^5$/um2, about 1×10$^2$/um2 to about 8×10$^5$/um2; about 50/um2 to about 5×10$^5$/um2; about 1×10$^2$/um2 to about 1×10$^5$/um2; about 50/um2 to about 5×10$^4$/um2; about 1×10$^2$/um2 to about 1×10$^4$/um2; about 1×10$^2$/um2 to about 5×10$^3$/um2; about 1×10$^2$/um2 to about 1×10$^3$/um2; about 50/um2 to about 5×10$^2$/um2; about 50/um2 to about 1×10$^2$/um2; or any value therebetween for the number of streptavidin groups/um2).

A streptavidin-presenting covalently functionalized region, like any described herein, may have an area of at least 0.5 mm$^2$, e.g., at least 0.6 mm$^2$, at least 0.7 mm$^2$, at least 0.8 mm$^2$, at least 0.9 mm$^2$, at least 1.0 mm$^2$, at least 1.1 mm$^2$, at least 1.2 mm$^2$, at least 1.3 mm$^2$, at least 1.4 mm$^2$, at least 1.5 mm$^2$, at least 1.6 mm$^2$, at least 1.7 mm$^2$, at least 1.8 mm$^2$, at least 1.9 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, at least 50 mm$^2$, or any range defined by two of the foregoing end points. Thus, for example, the area of the streptavidin-presenting covalently functionalized region may range from about 0.5 mm$^2$ to about 50 mm$^2$, about 1 mm$^2$ to about 40 mm$^2$, 2 mm$^2$ to about 35 mm$^2$, about 3 mm$^2$ to about 30 mm$^2$, or about 4 mm$^2$ to about 25 mm$^2$. Typically, the streptavidin-presenting covalently functionalized region has an area equal to or less than 100 mm$^2$ (e.g., equal to or less than 75 mm$^2$, or equal to or less than 50 mm$^2$).

It can be desirable to use the control afforded by the above routes of preparation, to select the density of streptavidin moieties to provide sufficient numbers of binding sites (streptavidin having up to four available binding sites) to bind one or more different activating molecules within the activating region of the surface, while providing an upper limit to the density at which activating molecules can be present. Without wishing to be bound by theory, it may be possible to over stimulate lymphocytes with a density of stimulating ligands over the highest density described here, which may drive the lymphocyte to less desired physiological states, e.g., exhausted phenotypes or non-specifically activated phenotypes.

Selectively introduced covalently functionalized regions. As mentioned, Applicants have discovered that creating limited regions of activation within a volume accessible to lymphocytes, offers greatly improved activated phenotypes. Accordingly, the introduction of the covalently functionalized surfaces capable of binding lymphocyte activating ligands may be performed within a prescribed region of a surface of a wellplate. In some embodiments, one or more surfaces of the wellplate may have an azido-presenting covalently functionalized region introduced. The one or more surfaces may be one or more wells of the well plate and further, may be a bottom surface of one or more wells of the well plate, where the bottom surface. As referred to herein, a bottom surface is located on a wall of an enclosure forming the well, where the bottom surface is disposed opposite the opening at the top of the well in the well plate. In some embodiments, the azido-presenting covalently functionalized region is not located on a side wall of the enclosure forming the well, where the side wall is adjacent to the opening of the well in the well plate.

However, in various embodiments, all of the surfaces of a well plate may have an azido-presenting covalently functionalized surface introduced, particularly when the azido-linked trialkoxysiloxane is reacted as a volatilized reagent contacting the surface of the well plate to react with the surface exposed moieties. As mentioned, less than all of the surfaces may be reacted to form azido-presenting covalently functionalized surfaces, when masking of any suitable type is employed. For example, the upper and lower sides of a well plate may be masked, such that only the surfaces inside one or more of the wells are reacted to form the azido-presenting covalently functionalized region. Alternatively, only selected wells of the well plate may be reacted to have an azido-presenting covalently functionalized region, which extends on all of the surfaces inside the well, including the bottom and the side walls. In yet another variation, only the bottom surface of one or more wells of the well plate may be reacted to have an azido-presenting covalently functionalized region within the bottom of the one or more wells of the well plate.

The azido-presenting covalently functionalized region of any of these surfaces may have an area of at least 0.5 mm$^2$ (e.g., at least 1.0 mm$^2$, at least 1.5 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, at least 50 mm$^2$, at least 75 mm$^2$, at least 100 mm$^2$, at least 150 mm$^2$, at least 200 mm$^2$, at least 250 mm$^2$, at least 300 mm$^2$, at least 400 mm$^2$, at least 500 mm$^2$, at least 600 mm$^2$, at least 700 mm$^2$, at least 800 mm$^2$, at least 900 mm$^2$, at least 1,000 mm$^2$, at least 2,000 mm$^2$, at least 3,000 mm$^2$, at least 4,000 mm$^2$, at least 5,000 mm$^2$, at least 6,000 mm$^2$, at least 7,000 mm$^2$, at least 8,000 mm$^2$, at least 9,000 mm$^2$, at least 10,000 mm$^2$, at least 20,000 mm$^2$, at least 30,000 mm$^2$, at least 40,000 mm$^2$, at least 50,000 mm$^2$, at least 60,000 mm$^2$, at least 70,000 mm$^2$, at least 80,000 mm$^2$, at least 90,000 mm$^2$, at least 100,000 mm$^2$, or more (e.g., substantially all of the inner surface of a well, or each of two or more wells, of the well plate)). Additionally, the azido-presenting covalently functionalized region has a density of azido groups of at least 50/um$^2$, e.g., from about 50 azido groups/um$^2$ to about 2×10$^7$/um$^2$, about 1×10$^2$/um$^2$ to about 1×10$^7$/um$^2$; about 50/um$^2$ to about 5×10$^6$/um$^2$; about 1×10$^2$/um$^2$ to about 1×10$^6$/um$^2$; about 1×10$^2$/um$^2$ to about 5×10$^5$/um$^2$; about 1×10$^2$/um$^2$ to about 1×10$^5$/um$^2$; about 1×10$^2$/um$^2$ to about 5×10$^4$/um$^2$; about 50/um$^2$ to about 5×10$^4$/um$^2$; about 1×10$^2$/um$^2$ to about 5×10$^3$/um$^2$; about 50/um$^2$ to about 5×10$^2$/um$^2$; or any value therebetween for the number of azido groups/um$^2$.

Similarly, the biotin-presenting covalently functionalizes region of the surface of the well plate may be introduced over all the surfaces of the well plate or at selected and/or restricted regions of a surface of the well plate. In some embodiments, a well plate having an azido-presenting covalently functionalized region on at least the surfaces of one or more wells of the well plate has a biotin-presenting covalently functionalized region within at least one surface of the one or more wells. In particular, the biotin-presenting covalently functionalized region similar to region 120 may be formed on a portion of the bottom of the one or more wells of the well plate, by adding the biotin linked Click reagent 107 only to the region within the desired portion of the bottom of the well, where the bottom surface is disposed opposite the opening at the top of the well in the well plate. In some embodiments, the biotin-presenting covalently functionalized region is not located on a side wall of the enclosure forming the well, where the side wall is adjacent to the opening of the well in the well plate. In some embodiments, this may be an alkyne Click reagent rather than a DBCO Click reagent, and a copper catalyzed Click reaction performed to obtain selected boundaries of the region.

The biotin-presenting covalently functionalized region of a surface of a well plate may have an area of at least 0.5 mm$^2$, e.g., at least 0.6 mm$^2$, at least 0.7 mm$^2$, at least 0.8 mm$^2$, at least 0.9 mm$^2$, at least 1.0 mm$^2$, at least 1.1 mm$^2$, at least 1.2 mm$^2$, at least 1.3 mm$^2$, at least 1.4 mm$^2$, at least 1.5 mm$^2$, at least 1.6 mm$^2$, at least 1.7 mm$^2$, at least 1.8 mm$^2$, at least 1.9 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, at least 50 mm$^2$, or more. Thus, the area of the biotin-presenting covalently functionalized region may range from about 0.5 mm$^2$ to about 50 mm$^2$, about 1 mm$^2$ to about 40 mm$^2$, 2 mm$^2$ to about 35 mm$^2$, about 3 mm$^2$ to about 30 mm$^2$, or about 4 mm$^2$ to about 25 mm$^2$. Typically, the biotin-presenting covalently functionalized region has an area equal to or less than 100 mm$^2$ (e.g., equal to or less than 75 mm$^2$, or equal to or less than 50 mm$^2$). The area of the biotin-presenting covalently functionalized region may be less than about 50%, less than about 25%, less than about 15%, less than about 10%, less than about 5%, or less than about 2% of the area of the bottom of each of one or more wells of the well plate. Alternatively, this relationship can be stated as the area of the biotin-presenting covalently functionalized region has an area of less than about 35 mm$^2$, less than about 20 mm$^2$, less than about 12 mm$^2$, less than about 5 mm$^2$, less than about 2 mm$^2$, less than about 1 mm$^2$, or less than about 0.5 mm$^2$. The biotin-presenting covalently functionalized region may have a dimension of about 0.5 mm to about 4.0 mm (e.g., about 1.0 mm to about 35 mm, or about 1.5 mm to about 3.0 mm). The biotin-presenting covalently functionalized region may have any desired shape: round, oval, irregular, rectangular, square, or polygonal. In some embodiments, the biotin presenting covalently functionalized region may be substantially circular and has a diameter of about 0.5 mm to about 4.0 mm (e.g., about 1.0 mm to about 35 mm, or about 1.5 mm to about 3.0 mm).

Additionally, the surface of the well plate may include a plurality of biotin-presenting covalently functionalized regions. Further, biotin containing reagents may be coupled to the reactive moieties of a surface one or more wells of the well plate wherein the plurality of biotin-presenting covalently functionalized regions may be clustered on the bottom of a well of the well plate. An area of each of the plurality of biotin-presenting covalently functionalized regions may be less than about 5% of an area of the bottom of one or more wells. A total area of the plurality of biotin-presenting covalently functionalized regions may be less than about 50% or about 25% of the area of the bottom of the at least one well.

The biotin-presenting covalently functionalized region(s) may have a density of biotin functionalities of at least 50/um$^2$ (e.g., from about 50 biotin groups/um$^2$ to about 5×10$^6$/um$^2$, about 1×10$^2$/um$^2$ to about 1×10$^6$/um$^2$; about 1×10$^2$/um$^2$ to about 5×10$^5$/um$^2$; about 1×10$^2$/um$^2$ to about 1×10$^5$/um$^2$; about 1×10$^2$/um$^2$ to about 5×10$^4$/um$^2$; about 1×10$^2$/um$^2$ to about 1×10$^4$/um$^2$; about 1×10$^2$/um$^2$ to about 5×10$^3$/um$^2$; about 1×10$^2$/um$^2$ to about 1×10$^3$/um$^2$; about 50/um$^2$ to about 5×10$^2$/um$^2$; about 50/um$^2$ to about 1×10$^2$/um$^2$; or any value therebetween for the number of biotin groups/um$^2$).

The streptavidin-presenting covalently functionalized region of a surface of a well plate may be similarly be formed at selected regions, whether directly coupled to azido moieties as shown for region 155 of FIG. 1C, via Click or copper-mediated Click reactions, or coupled via binding to biotin moieties of biotin-presenting covalently functionalized regions as shown for regions 125, 140, 150 of FIGS. 1A and 1B. In any case, the streptavidin-presenting covalently functionalized region may be formed on a surface within one or more wells of a well plate. Further, the streptavidin-presenting covalently functionalized region may be formed on a surface only a desired portion of the bottom of the well, where the bottom surface is disposed opposite the opening at the top of the well in the well plate. In some embodiments, the streptavidin—presenting covalently functionalized region is not located on a side wall of the enclosure forming the well, where the side wall is adjacent to the opening of the well in the well plate.

The streptavidin-presenting covalently functionalized region(s) may have an area of at least 0.5 mm$^2$, e.g., at least 0.6 mm$^2$, at least 0.7 mm$^2$, at least 0.8 mm$^2$, at least 0.9 mm$^2$, at least 1.0 mm$^2$, at least 1.1 mm$^2$, at least 1.2 mm$^2$, at least 1.3 mm$^2$, at least 1.4 mm$^2$, at least 1.5 mm$^2$, at least 1.6 mm$^2$, at least 1.7 mm$^2$, at least 1.8 mm$^2$, at least 1.9 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, at least 50 mm$^2$, or more. Thus, the area of the streptavidin-presenting covalently functionalized region may range from about 0.5 mm$^2$ to about 50 mm$^2$, about 1 mm$^2$ to about 40 mm$^2$, 2 mm$^2$ to about 35 mm$^2$, about 3 mm$^2$ to about 30 mm$^2$, or about 4 mm$^2$ to about 25 mm$^2$. Typically, the streptavidin-presenting covalently functionalized region has an area equal to or less than 100 mm$^2$ (e.g., equal to or less than 75 mm$^2$, or equal to or less than 50 mm$^2$). The streptavidin-presenting covalently functionalized region(s) may have a density of streptavidin functionalities of at least 50/um$^2$). from about 50 streptavidin groups/um$^2$ to about 8×10$^5$/um$^2$, about 1×10$^2$/um$^2$ to about 8×10$^5$/um$^2$; about 50/um$^2$ to about 5×10$^5$/um$^2$; about 1×10$^2$/um$^2$ to about 1×10$^5$/um$^2$; about 50/um$^2$ to about 5×10$^4$/um$^2$; about 1×10$^2$/um$^2$ to about 1×10$^4$/um$^2$; about 1×10$^2$/um$^2$ to about 5×10$^3$/um$^2$; about 1×10$^2$/um$^2$ to about 1×10$^3$/um$^2$; about 50/um$^2$ to about 5×10$^2$/um$^2$; about 50/um$^2$ to about 1×10$^2$/um$^2$; or any value therebetween for the number of streptavidin groups/um$^2$).

The streptavidin-presenting covalently functionalized region(s) may have an area of less than about 50% of an area of a bottom surface of each of the one or more wells. The area of the streptavidin-presenting covalently functionalized region(s) may be less than about 25%, less than about 15%, less than about 10%, less than about 5%, or less than about 2% of the area of the bottom of each of the one or more wells. Alternatively, this relationship can be stated as the area of the streptavidin-presenting covalently functionalized region(s) may have an area of less than about 35 mm$^2$, less than about 20 mm$^2$, less than about 12 mm$^2$, less than about 5 mm$^2$, less than about 2 mm$^2$, or less than about 1 mm$^2$. In some embodiments, the streptavidin-presenting covalently functionalized region(s) may have a dimension of about 0.5 mm to about 4.0 mm (e.g., about 1.0 mm to about 35 mm, or about 1.5 mm to about 3.0 mm).

The streptavidin-presenting covalently functionalized region(s) may have any desired shape: round, oval, irregular, rectangular, square, or polygonal. In some embodiments, the streptavidin-presenting covalently functionalized region may be substantially circular and has a diameter of about 0.5 mm to about 4.0 mm (e.g., about 1.0 mm to about 35 mm, or about 1.5 mm to about 3.0 mm). In some embodiments, the streptavidin-presenting covalently functionalized region(s) may be substantially circular and may have a diameter of about 0.5 mm to about 4.0 mm (e.g., about 1.0 mm to about 3.5 mm, or about 1.5 mm to about 3.0 mm).

Additionally, the surface of the well plate may include a plurality of streptavidin-presenting covalently functionalized regions. Further, streptavidin containing reagents may be coupled to the reactive moieties of a surface of one or more wells of the well plate or streptavidin may be bound to biotin moieties of a biotin-presenting covalently functionalized region of a surface, wherein the plurality of streptavidin-presenting covalently functionalized regions may be clustered on the bottom of a well of the well plate. An area of each of the plurality of streptavidin-presenting covalently functionalized regions may be less than about 5% of an area of the bottom of one or more wells. A total area of the plurality of streptavidin-presenting covalently functionalized regions may be less than about 50% or about 25% of the area of the bottom of the at least one well.

Figure 1D:
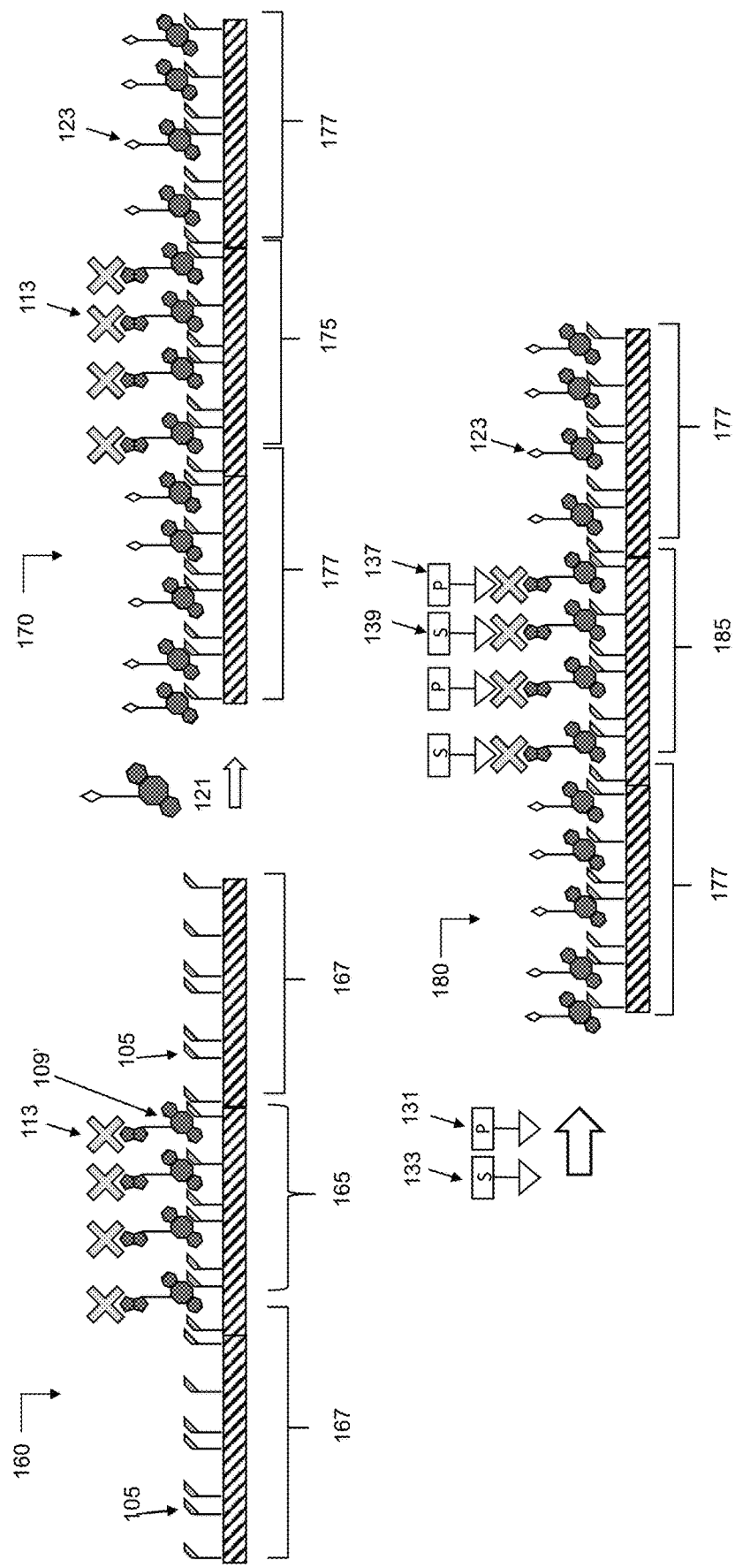
FIG. 1D is a schematic representation for introducing a restricted region of a surface having streptavidin-presenting covalently linked ligands, and subsequent introduction of activating ligands for activating a lymphocyte according to some embodiments of the disclosure.

Surface blocking modified regions. In some embodiments, the surface of the well plate or each of the one or more wells further comprises another (e.g., second) covalently modified region comprising surface blocking ligands. As shown in FIG. 1D, surface 160, has a streptavidin-presenting covalently functionalized region 165, with streptavidin ligands 113, which is like region 125, via initial covalent functionalization by biotinyl ligands 109', followed by streptavidin binding to the biotin moiety. A second region 167, surrounding streptavidin-presenting covalently functionalized region 165, may be further modified with surface blocking ligands, by reacting the reactive moieties (in this case, azido moieties of azido-presenting ligands 105) with surface blocking DBCO reagent 121. The surface blocking ligands may have any surface blocking moiety as described herein (e.g., containing a hydrophilic or negatively charged moiety and/or polyethylene glycol (PEG) moieties). The resulting surface 170, has the streptavidin-presenting covalently functionalized region 165, surrounded by a second region, 177, having modified surface 177 containing surface blocking ligands 123. The surface blocking ligands may be a single type of surface blocking ligands or may be a mixture of surface blocking ligands. The selection of the type/mixture of surface blocking ligands 123 may provide optimized support for lymphocyte cell culturing. While illustrated in FIG. 1D for a surface 160 having a streptavidin-presenting covalently functionalized region 165, similar surfaces having covalently functionalized regions 120, 125, 135, 140, 145, 150, 155 may have similar surrounding second regions containing reactive moiety presenting ligands, e.g., azido-presenting ligands 105, and may be similarly modified to introduce surface blocking ligands 123 in the respective surrounding second region. In some embodiments, the surface modified region such as region 177, does not overlap the biotin-presenting covalently functionalized region 120, 135, 145 or the streptavidin-presenting covalently functionalized regions 125, 135, 145, 155.

In some variations, the second covalently modified region may further include at least one ligand providing a moiety stimulating adherence. For example, a peptide sequence attached to a DBCO Click coupling reagent may be introduced into region 177. The peptide sequence may include a RGD (Arg-Gly-Asp) motif, which may stimulate a lymphocyte during culture by providing mechanical adherence. Any other adherence stimulating moiety may be adapted and similarly introduced. The adherence stimulating moiety may be introduced after the introduction of streptavidin-presenting region 165, and prior to, contemporaneously with or subsequent to the introduction of surface blocking ligands 123 forming surface blocking region 177.

Well plate having a surface including a lymphocyte-activating covalently functionalized region. As mentioned above, Applicants have discovered that using activating surfaces of a wellplate, where activation is limited to a region of the surface provides more controllable and efficient activation of lymphocytes. The lymphocyte may be any suitable lymphocyte, including but not limited to a T cell, a Natural killer T (NKT) cell, or a B cell. As shown in FIG. 1D, activating moieties may be introduced and bound to a streptavidin-presenting covalently functionalized region of a surface. Introduction of activating moieties is shown for surface 170, but the invention is not so limited. Any surface incorporating covalently functionalized regions like regions 125, 140, 150, 155 may have activating moieties introduced, to form the lymphocyte-activating covalently functionalized region like region 185 of surface 180. In some embodiments, the blocking ligand-modified region 177 and the lymphocyte activating covalently functionalized region 185 cover an entire surface of a well plate. In some embodiments, the blocking ligand-modified region 177 and the lymphocyte activating covalently functionalized region 185 are non-overlapping regions of the surface. The lymphocyte activating covalently functionalized region 185 may be introduced onto a surface within each of one or more wells of the well plate. In some variations, the lymphocyte activating covalently functionalized region 185 may be introduced on a bottom surface of each of the one or more wells. In some embodiments, the lymphocyte activating covalently functionalized region is disposed only on the bottom surface of the corresponding well. The lymphocyte activating covalently functionalized region may have an area of less than about 50% of an area of the bottom of the one or more wells. An area of the lymphocyte activating covalently functionalized region is less than about 50%, less than about 25%, less than about 15%, less than about 10%, less than about 5%, less than about 2%, or less than about 1% of the area of the bottom of the one or more wells. An area of the lymphocyte activating covalently functionalized region has an area of less than about 35 mm$^2$, about 20 mm$^2$, about 12 mm$^2$, about 5 mm$^2$, less than about 2 mm$^2$, or less than about 1 mm$^2$. In some embodiments, the lymphocyte activating covalently functionalized region has a dimension of about 0.5 mm to about 4.0 mm (e.g., about 1.0 mm to about 35 mm, or about 1.5 mm to about 3.0 mm). The lymphocyte activating covalently functionalized region(s) may have any desired shape: round, oval, irregular, rectangular, square, or polygonal. In some embodiments, the lymphocyte activating covalently functionalized region may be substantially circular and has a diameter of about 0.5 mm to about 4.0 mm (e.g., about 1.0 mm to about 35 mm, or about 1.5 mm to about 3.0 mm). In some embodiments, the lymphocyte activating covalently functionalized region(s) may be substantially circular and may have a diameter of about 0.5 mm to about 4.0 mm (e.g., about 1.0 mm to about 35 mm, or about 1.5 mm to about 3.0 mm).

In some variations, activating molecules 131, each comprising an activating moiety, e.g., "P" of molecule 131, and a binding moiety, such as biotin, which can bind a binding site of streptavidin, and form the lymphocyte activating covalently functionalized region 185. The bound first activating molecule complex 137 may be referred to as a specifically bound activating molecular ligand. In some variations, there may be only one kind of activating molecule. In other variations, there may be a first activating molecule 131, which may be a primary activating molecule, as well as other types of activating molecules 133. The activating molecules 133 may be additional activating molecules, co-activating molecules, adjunct activating molecules, or secondary activating molecules. The ratio of first activating molecule to second activating molecules may be any suitable ratio for activating a lymphocyte, such as, 10:1; 8:1; 6:1: 5:1: 3:1; 2:1; 1:1; 1:2; 1:3; 1:5; 1:6: 1:8; 1:10, or more.

In some variations, first activating molecules 131 may be, but are not limited to, cell surface clusters of differentiation binding molecule, immunoglobulin-binding molecules, T-cell receptor molecule activating molecules, TNF receptor superfamily binding molecules, chemokine receptor binding molecules, growth factor molecules, or adhesion promoting molecules. In some variations, the first activating molecules may include an MHC molecule (e.g., Class I or Class II), a protein or fragment thereof retaining cell surface clusters of differentiation binding activity, a protein or fragment thereof retaining T cell receptor binding activity, a protein or fragment thereof retaining TNF receptor superfamily binding activity, a protein or fragment thereof retaining chemokine receptor binding activity, a protein or fragment thereof retaining growth stimulatory activity or a protein or fragment thereof retaining adhesion promoting activity. A protein may be an antibody or a fragment thereof, that can retain binding activity to the specified target.

The specifically bound first activating molecular ligands may have a density of at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, or from about $1\times10^2$ to about $1\times10^5$ molecules per square micron in the lymphocyte activating covalently functionalized region.

In some variations, second activating molecules 133, each including an activating moiety, e.g., "S", and a binding moiety, where the binding moieties bind a binding site of streptavidin, may be introduced to the lymphocyte activating region 185, providing specifically bound second activating molecular ligands 139 in the lymphocyte activating covalently functionalized region 185. The plurality of second activating molecules may include, but are not limited to T cell receptor (TCR) co-activating molecules, cell surface immunoglobulin binding molecules, growth factor molecules, adhesion promoting molecules, amongst others. The second activating molecule may 133 be one kind of second activating molecule or the second activating molecule 133 may be a mixture of more than one different molecules, which may be used in any ratio deemed suitable for the activation of the lymphocyte.

In some variations, the specifically bound second activating molecular ligands 137 may have a density from about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, bout $1\times10^2$ to about $1\times10^5$ molecules per square micron, or about 1×10³ to about 1×10⁵ molecules per square micron in the lymphocyte activating covalently functionalized region.

In some variations, the well plate having a surface including a lymphocyte activating region may have a plurality of lymphocyte activating covalently functionalized regions in each of the one or more wells. An area of each of the plurality of lymphocyte activating covalently functionalized regions may be less than about 5% of an area of the bottom of the one or more wells. In some embodiments, a total area of the plurality of lymphocyte activating covalently functionalized regions is less than about 50%, about 25%, or about 10% of the area of the bottom of the one or more wells.

Molecular Ligands. Any suitable lymphocyte activating ligand may be included in the lymphocyte activating region of the surfaces of the well plates described herein. The activating ligand may be a cell surface clusters of differentiation binding molecule, T-cell receptor molecule activating molecule, TNF receptor superfamily binding molecule, chemokine receptor binding molecule, growth factor molecule, or adhesion promoting molecule. Some non-limiting examples of these molecules include: CD2, CD3, CD19, CD20, CD27, CD28, CD30, CD40, CD48, CD58, CD70, CD83, CD137, CD122, CD155, CD226 binding molecules, and the like. These binding molecules may include recombinant ligands thereof. In particular, CD2, CD28 binding molecules may be useful for activating antigen-specific T cells. CD3, CD137 or CD40 ligands may be useful for activating expansion of T cells. CD19 and CD20 binding molecules may be useful for activating chimeric antigen receptor (CAR) T cells. The activating molecules may be agonist antibodies of these molecules such as anti-CD2, anti-CD3, anti-CD27, anti-CD28, anti-CD30, anti-CD40, anti-CD58, anti-CD48, anti-CD122, anti-CD137, and the like.

Chemokine receptor ligands may be used to activate lymphocytes, such as those belonging to the CCL family such as CCL21 or CCL19. Inducible T-cell costimulator is an immune checkpoint protein, and CD278 or LCOS (Inducible T-cell COStimulator) binding molecule or agonist antibody may be used in the activating presenting regions described herein. Hepatitis A virus cellular receptor 1 (HAVcr-1) also known as T-cell immunoglobulin and mucin domain 1 (TIM-1) is a protein that in humans is encoded by the HAVCR1 gene. Anti-TIM1 or TIM4 ligands may be used to activate T cells.

DR3, also known as TNFRSF25, lymphocyte-associated receptor of death (LARD), belongs to the TNF receptor superfamily (TNFRSF). Binding molecules thereof, or agonist antibodies thereof, may be used to activate T cells and NKT cells.

Signaling lymphocyte activation molecule (SLAM) family member 1 (also known as CD150) is a self-ligand cell surface glycoprotein expressed on T cells, B cells, macrophages, and dendritic cells. CD150 plays an important role in adhesion and signaling between T cells and antigen-presenting cells (APCs). CD150 is the prototypical member of a growing family of glycoprotein receptors on hematopoietic stem cells known as the SLAM family, which includes CD229, CD84, CD244, SF2000/Ly108, SF2001, and 19A (CRACC). Agonist antibodies may be use to activate lymphocytes, particularly T cell and B cells.

GITR (glucocorticoid-induced TNFR family related gene) is a member of the TNFR superfamily (TNFRSF). Anti-GITR or GITR ligand may be used to activate T cells. OX40 (CD134) and its binding partner, OX40L (CD252), are members of the TNFR/TNF superfamily and are expressed on activated CD4 and CD8 T cells as well as a number of other lymphoid and non-lymphoid cells. OX40 and OX40L also regulate cytokine production from T cells, antigen-presenting cells, NK cells, and NKT cells, and modulate cytokine receptor signaling, and antibodies or ligands thereof may be used to activate T cells or NK cells.

CD137 is a member of the tumor necrosis factor (TNF) receptor family Its alternative names are tumor necrosis factor receptor superfamily member 9 (TNFRSF9), 4-1BB and induced by lymphocyte activation (ILA). Anti-41BB or 41BB-L may be used in the activating regions to activate lymphocytes. Herpesvirus entry mediator (HVEM), also known as tumor necrosis factor receptor superfamily member 14 (TNFRSF14), is a human cell surface receptor of the TNF-receptor superfamily.

Cytokines such as IL7 and/or IL15 may be introduced within the lymphocyte activation regions or may be introduced within the modified surface surrounding the lymphocyte activation regions.

To expand NK cells or NK CAR cells, natural killer receptor binding molecules such as NKG2D ligand may be introduced within the lymphocyte activation regions.

Immunoglobulin binding molecules may be used, such as MHC molecules, as mentioned above. The MHC may be a Class I MHC. In some other embodiments, the MHC may be a Class II MHC, in order to activate different subtypes of T cells.

Also as mentioned above, the growth factor ligands or adhesion promoting ligands may be used.

Well plate having an antigen-presenting covalently functionalized region. In some variations, the well plate having a lymphocyte activating covalently functionalized region may be an antigen-presenting covalently functionalized region of the well plate for activating a T cell (T cell), and may have any of the features of the well plate having a lymphocyte activating covalently functionalized region, or regions, as described above. That is, each of one or more wells of the well plate may have a surface having an antigen-presenting covalently functionalized region. The antigen-presenting covalently functionalized region of each of the one or more wells may be located on a bottom surface of the corresponding well. Further, the antigen-presenting covalently functionalized region of each of the one or more wells may be disposed only on the bottom surface of the one or more wells. In some embodiments, the antigen-presenting covalently functionalized region may not be disposed on a side wall of the one or more wells. In some embodiments, each of the one or more wells of the well plate may have a plurality of antigen-presenting covalently functionalized regions disposed only on the bottom surface of the one or more wells.

The antigen-presenting covalently functionalized region may include specifically bound primary activating molecular ligands 137 ("first activating molecular ligands) and specifically bound co-activating molecular ligands 139 ("second activating molecular ligands), where each of the primary activating molecules 131 has a primary activating moiety ("P") and a binding moiety (e.g., biotin) that can bind to a binding site of streptavidin of a streptavidin-presenting functionalized region 125, 140, 150, 155, 170, and the like. The primary activating molecular ligands 137 and co-activating molecular ligands 139 may be disposed within the antigen-presenting covalently functionalized region in any of the ratios described herein, such as about 1:1 to about 2:1; about 1:1; or about 3:1 to about 1:3.

In some variations, the specifically bound primary activating molecular ligands 137 each comprises a major histocompatibility complex (MHC) molecule (e.g., Class I or Class II) configured to bind to a T cell receptor of the T cell. The MHC molecule may include an MHC Class I protein sequence, a beta microglobulin protein sequence, and an antigenic peptide. In some variations, the protein sequence of the MHC molecule may be connected to the antigen-presenting synthetic surface via a C-terminal connection of the protein sequence, e.g., by a C-terminal BirA tag for site-specific biotinylation.

The specifically bound primary activating molecular ligands 137 may have a density of at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, or from about $1\times10^2$ to about $1\times10^5$ molecules per square micron in the antigen-presenting covalently functionalized region like 185.

The primary activating molecules including an MHC molecule may further include a tumor associated antigenic peptide, which may be any suitable tumor associated antigenic peptide, as may be determined by one of skill. The tumor associated antigenic peptide may be noncovalently associated with the primary activating molecular ligand (e.g., MHC molecule). The tumor associated antigenic peptide may be presented by the primary activating molecular ligand (e.g., MHC molecule) in an orientation which can initiate activation of a T lymphocyte. The tumor associated antigen may be a peptide.

Some non-limiting examples of tumor associated antigens include MART1 (peptide sequence ELAGIGILTV), for melanoma, NYES01 (peptide sequence SLL WITQV), involved in melanoma and some carcinomas, SLC45A2, TCL1, and VCX3A, but the disclosure is not so limited. Additional examples of tumor antigens include peptides comprising a segment of amino acid sequence from a protein expressed on the surface of a tumor ceil such as CD19, CD20, CLL-1, TRP-2, LAGE-1, HER2, EphA2, FOLR1, MAGE-A1, mesothelin, SOX2, PSM, CA125, T antigen, etc. The peptide can be from an extracellular domain of the tumor associated antigen. An antigen is considered tumor associated if it is expressed at a higher level on a tumor ceil than on a healthy cell of the type from which the tumor ceil was derived. The T cell which recognizes this tumor associated antigen is an antigen specific T ceil, Any tumor associated antigen may be utilized in the antigen presenting surface described herein. In some embodiments, the tumor associated antigen is a neoantigenic peptide, e.g., encoded by a mutant gene in a tumor cell. For detailed discussion of neoantigenic peptides, see, e.g., US2011/0293637. In some embodiments, the tumor associated antigen may be SLC45A2, TCL1, VCX3A, MART1 or NYESO1.

In other variations, the antigenic peptide may be a viral antigen, a bacterial antigen, a fungal antigen or a protozoan antigen.

The specifically bound co-activating molecular ligands 133 (e.g., second activating molecular ligands) may each include a T cell receptor (TCR) co-activating moiety ("S"); or an adjunct TCR activating moiety ("S"). The ratio of the TCR co-activating molecules to the adjunct TCR activating molecules of the plurality of co-activating molecular ligands may be about 100:1 to about 1:100. In some embodiments, a ratio of the TCR co-activating molecules to the adjunct TCR activating molecules of the plurality of co-activating molecular ligands may be 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about". In some embodiments, a ratio of the TCR co-activating molecules to the adjunct TCR activating molecules of the plurality of co-activating molecular ligands may be from about 20:1 to about 1:20 or about 3:1 to about 1:3.

In some embodiments, the TCR co-activating molecules may include a CD28 binding protein or a fragment thereof, which retains binding ability to CD28. The CD28 binding protein or the fragment thereof may further include a site-specific C-terminal biotin moiety. In some embodiments, the T cell receptor (TCR) co-activating molecules may include a CD80 molecule or a fragment thereof, where the fragment retains binding activity to CD28. In some other embodiments, the T cell receptor (TCR) co-activating molecule may include an anti-CD28 antibody or a fragment thereof.

In some variations, the adjunct TCR activating molecule may include a CD2 binding protein, or a fragment thereof, where the fragment retains binding activity to CD2. The CD2 binding protein or the fragment thereof may further include a site-specific C-terminal biotin moiety. In other variations, the adjunct TCR activating molecule may include a CD58 molecule or fragment thereof, wherein the fragment retains binding activity with CD2. In some embodiments, the adjunct TCR activating molecule may include an anti-CD2 antibody or a fragment thereof. The specifically bound co-activating molecular ligands may have a density from at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, or about $1\times10^3$ to about $1\times10^5$ molecules per square micron on the antigen-presenting synthetic surface in the antigen-presenting covalently functionalized region.

Cleavable linker. In some embodiments, a cleavable linker may be included in the linkers connecting activating ligands, covalently linked streptavidin, biotin, or azido moieties. The cleavable linker may include a disulfide moiety or may include a photocleavable moiety such as a substituted nitrobenzyl linker, which may be cleaved with UV light irradiation at about 365 nm. These can be used to remove surface bound ligands after a desired period of use or may be used in methods requiring a mask or photomask for site selective introduction of a desired molecular ligand only in the region not so masked/photomasked. After site selective introduction of the molecular ligand, the masking ligands may be released from the surface under alkaline conditions in the presence of thiols (disulfides) or by photocleavage.

Surface-blocking reagents and ligands formed therefrom. Surface blocking reagents used for the surfaces described herein may be of two types. A first type includes a surface blocking reagent such as surface blocking reagent 117 of FIG. 1A, which may have a reactive moiety configured to react with remaining reactive moieties of the cleaned/prepared surface 110, such as oxide functionalities existing natively or introduced by cleaning or other oxidative step. The surface blocking reagent 117 includes one reactive functionality such as a trialkoxysiloxane, configured to react with the surface exposed moieties, e.g., oxides, and contains no other functionality that will react, e.g., interfere, with any of the biotin-containing reagent, streptavidin, or streptavidin containing reagents.

A second class of surface blocking reagents may be like surface blocking DBCO reagent 121, which is configured to reactive with reactive functionalities such as azides or alkynes, of an initially functionalized surface 115. Therefore, the second class of surface blocking reagents has one reactive moiety such as an alkyne (including cyclic strained alkynes such as DBCO) configured to react with ligand 105 as shown in FIGS. 1A and 1B.

No matter which class of surface blocking reagent, the reactive moiety of the surface blocking reagent has a linking portion, which may be an alkyleneoxide, alkyl or substituted alkenyloxide or alkyl linear moiety attached to the reactive moiety. Optionally, the linking portion has a linear structure.

The terminal moiety of the surface-blocking reagent, which will remain unbound after reacting with the surface, may be a hydrophilic moiety, an amphiphilic moiety, a zwitterionic moiety, or a negatively charged moiety. In some embodiments, the terminal blocking group comprises a terminal hydroxyl group. In some embodiments, the terminal blocking group comprises a terminal carboxyl group, in some embodiments, the terminal blocking group comprises a terminal zwitterionic group. The plurality of surface-blocking ligands may have all the same terminal surface-blocking group or may have a mixture of terminal surface-blocking groups. Without being bound by theory, the terminal surface-blocking group as well as a hydrophilic linker of the surface-blocking ligand may interact with water molecules In the aqueous media surrounding the modified surface to create a more hydrophilic surface overall. This enhanced hydrophilic nature may render the contact between the modified surface and a biological micro-object more compatible and more similar to natural intercellular interactions and/or cell-extracellular fluidic environment in-vivo.

The linking portion of the surface blocking reagent/ligand can comprise, for example, a polymer. The polymer may include a polymer including alkylene ether moieties. A wide variety of alkylene ether containing polymers may be suitable for use on the surfaces described herein. One class of alkylene ether containing polymers is polyethylene glycol (PEG $M_W$<100,000 Da), which are known in the art to be biocompatible. In some embodiments, a PEG may have an Mw of about 88 Da, 100 Da, 132 Da, 176 Da, 200 Da, 220 Da, 264 Da, 308 Da, 3520a, 396 Da, 440 Da, 500 Da, 600 Da, 700 Da, 800 Da, 900 Da, 10000a, 1500 Da, 2000 Da, 5000 Da, 10,000 Da or20,000 Da, or may have a Mw that falls within a range defined by any two of the foregoing values. In some embodiments, the PEG polymer has a polyethylene moiety repeat of about 3, 4, 5, 10, 15, 25 units, or any value therebetween. In some embodiments, the PEG may be a carboxyl substituted PEG moiety. In some embodiments, the PEG is a hydroxyl substituted PEG moiety, in some embodiments, each of the plurality of surface-blocking ligands may have a linking portion having the same length as the linking portions of the other ligands of the plurality. In other embodiments, the linking portions of the plurality of surface-blocking ligands may have varied lengths. In some embodiments, the surface-blocking group and the length of the linking portion may be same for each of the plurality of surface-blocking ligands.

Alternatively, the surface blocking group and the length of the linking portion may vary within the plurality of the surface-blocking ligands and may include 2, 3, or 4 different surface-blocking groups and/or 2, 3, 4, or more different lengths, chosen in any combination, in general, the surface-blocking ligands have a length and/or structure that is sufficiently short so as not to sterically hinder the binding and/or function of the activating ligands. For example, in some embodiments, the length of the surface-blocking ligands is equal to or less than the length of the other linkers bound to the surface (e.g., linkers that connect coupling groups or activating ligands). In some embodiments, the length of the surface-blocking ligands is about 1 or more angstroms (e.g., about 2, 3, 4, 5, 10, 15, 20, 25, 30, 35, 40, 45, 50, 75, 100, or more angstroms) less than the length of the other linkers bound to the surface (e.g., linkers that connect activating ligands/molecules. In some embodiments, the length of the surface-blocking ligands is about 1 to about 100 angstroms (e.g., about 2 to about 75, about 3 to about 50, about 4 to about 40, or about 5 to about 30 angstroms) less than the length of the other linking portions bound to the surface. When the surface-blocking ligands have a linking portion length that is the same or somewhat less than the length of the other linking portions bound to the surface, the resulting surface can provide a more biocompatible surface within the well of the well plate, or may prevent undesired attachment by biological micro-objects thereby preventing undesired attachment or biofouling, while providing full access for activating molecules to bind to the surface.

In some variations, the surface blocking reagent 117 or 121 may have an alkyleneoxide, alkyl or substituted alkyleneoxide or alkyl moiety attached to the trialkoxysiloxane. The alkyleneoxide, alkyl or substituted alkyleneoxide or alkyl moiety may be a linear moiety and may have a linear backbone length of at least 4 atoms, at least 8 atoms, at least 12 atoms, at least 16 atoms, at least 20 atoms, at least 50 atoms or at least 100 atoms, or more, which may be carbon, oxygen, nitrogen or sulfur.

Methods of Preparation

Reactive moiety-presenting region of a surface of a well plate. Preparing a well plate including a surface having an reactive moiety (e.g., azido-presenting, or an alkynyl-presenting) covalently functionalized region, includes contacting surface exposed moieties (e.g., oxide moieties) of a portion of the surface of the well plate with an azido-containing coupling reagent; and forming the reactive moiety-presenting covalently functionalized region of the well plate. The surface of the well plate comprises, consists of, or consists essentially of glass, polystyrene, polypropylene, polycarbonate, polyethylene, cycloolefin copolymer or melamine Plasma cleaning the surface of the well plate may be performed before contacting the surface exposed moieties of the portion of the surface with the azido containing coupling reagent. The reactive moiety containing coupling reagent may contact the surface exposed moieties in a gaseous phase or in a liquid phase during the coupling reaction. The reactive moiety containing coupling reagent may include a linker having a carbon backbone of 5 to 9 carbons. In some embodiments, the linker may have a carbon backbone of 7 carbons.

The reactive moiety-presenting (e.g., azido-presenting) covalently functionalized region may have a density of azido groups of at least 50/um2 (e.g., from about 50 azido groups/$um^2$ to about $2\times10^7$/um2, about $1\times10^2$/um2 to about $1\times10^7$/um2; about 50/um2 to about $5\times10^6$/um2; about $1\times10^2$/um2 to about $1\times10^6$/um2; about $1\times10^2$/um2 to about $5\times10^5$/um2; about $1\times10^2$/um2 to about $1\times10^5$/um2; about $1\times10^2$/um2 to about $5\times10^4$/um2; about 50/um2 to about $5\times10^4$/um2; about $1\times10^2$/um2 to about $5\times10^3$/um2; about 50/um2 to about $5\times10^2$/um2; or any value therebetween for the number of azido groups/um2).

Contacting the surface may include contacting a surface of each of one or more wells of the well plate with the reactive moiety-containing (e.g., azido-containing) coupling reagent, forming a surface having an reactive moiety-presenting covalently functionalized region in each of the one or more wells. Contacting may include contacting a bottom surface of the corresponding well with the reactive moiety-containing coupling reagent thereby forming an reactive moiety-presenting covalently functionalized region on the bottom surface of each of the one or more wells. In other embodiments, all of the surfaces of the well plate may be contacted, and a reactive-moiety presenting region may extend to all of the surfaces of the well plate.

In some embodiments, contacting the bottom surface of each of the one or more wells may include contacting only the bottom surface, thereby forming a reactive moiety (e.g., azido)—presenting covalently functionalized region on only the bottom surface of each of the one or more wells.

Preparing a biotin-presenting covalently functionalized region of a surface of a well plate. Preparing a well plate comprising a surface having a biotin-presenting covalently functionalized region, includes contacting a portion of the surface of the well plate with a reagent including a biotin moiety linked to a reactive group, wherein the reactive group is configured to react with reactive (e.g., azido or alkynyl) moieties of the surface, thereby forming a biotin-presenting functionalized region of the well plate. The method may further include contacting the surface of the well plate with a reagent including surface blocking ligands linked to a reactive group, wherein the reactive group is configured to react with reactive (e.g., azido- or alkynyl) moieties of the surface, thereby providing a blocking ligand-modified region of the surface. The blocking ligand-modified region and the biotin-presenting region may cover the entire surface. In some variations, the blocking ligand-modified region and the biotin-presenting region may be non-overlapping regions of the surface.

Contacting the portion of the surface of the well plate with the reagent having the biotin moiety linked to the reactive group may include contacting a surface within each of one or more wells of the well plate. Contacting each of the one or more wells may further include contacting each of the one or more wells at a bottom surface of the corresponding well with the reagent including the biotin moiety linked to the reactive group, thereby producing the biotin-presenting covalently functionalized region on the bottom surface of the corresponding well. In some embodiments, the reactive moieties (e.g., azido moieties) are disposed within one or more wells of the well plate, and optionally, may be disposed only within the one or more wells.

In some embodiments, the biotin-presenting covalently functionalized region may be formed only on the bottom surface of the corresponding well. The biotin-presenting covalently functionalized region may have a density of biotin functionalities of at least 50/um2 (e.g., from about 50 biotin groups/um$^2$ to about $5 \times 10^6$/um2, about $1 \times 10^2$/um2 to about $1 \times 10^6$/um2; about $1 \times 10^2$/um2 to about $5 \times 10^5$/um2; about $1 \times 10^2$/um2 to about $1 \times 10^5$/um2; about $1 \times 10^2$/um2 to about $5 \times 10^4$/um2; about $1 \times 10^2$/um2 to about $1 \times 10^4$/um2; about $1 \times 10^2$/um2 to about $5 \times 10^3$/um2; about $1 \times 10^2$/um2 to about $1 \times 10^3$/um2; about 50/um2 to about $5 \times 10^2$/um2; about 50/um2 to about $1 \times 10^2$/um2; or any value therebetween for the number of biotin groups/um2).

The biotin-presenting covalently functionalized region may have an area of less than about 50% of an area of the bottom of the at least one well. In some embodiments, an area of the biotin-presenting covalently functionalized region may be less than about 25%, less than about 15%, less than about 10%, less than about 5%, less than about 2%, or less than about 1% of the area of the bottom of the at least one well. An area of the biotin-presenting covalently functionalized region has an area of less than about 35 mm$^2$, about 20 mm$^2$, about 12 mm$^2$, about 5 mm$^2$, less than about 2 mm$^2$, or less than about 1 mm$^2$. In some embodiments, the biotin-presenting covalently functionalized region may have a dimension of about 0.5 mm to about 4.0 mm (e.g., about 1.0 mm to about 35 mm, or about 1.5 mm to about 3.0 mm). The biotin-presenting covalently functionalized region may be substantially circular and may have a diameter of about about 0.5 mm to about 4.0 mm (e.g., about 1.0 mm to about 35 mm, or about 1.5 mm to about 3.0 mm).

The method may further include contacting a plurality of regions of the bottom of each of the one or more wells with the biotin-containing reagent to produce a plurality of biotin-presenting regions in each of the one or more wells.

Figure 6A:
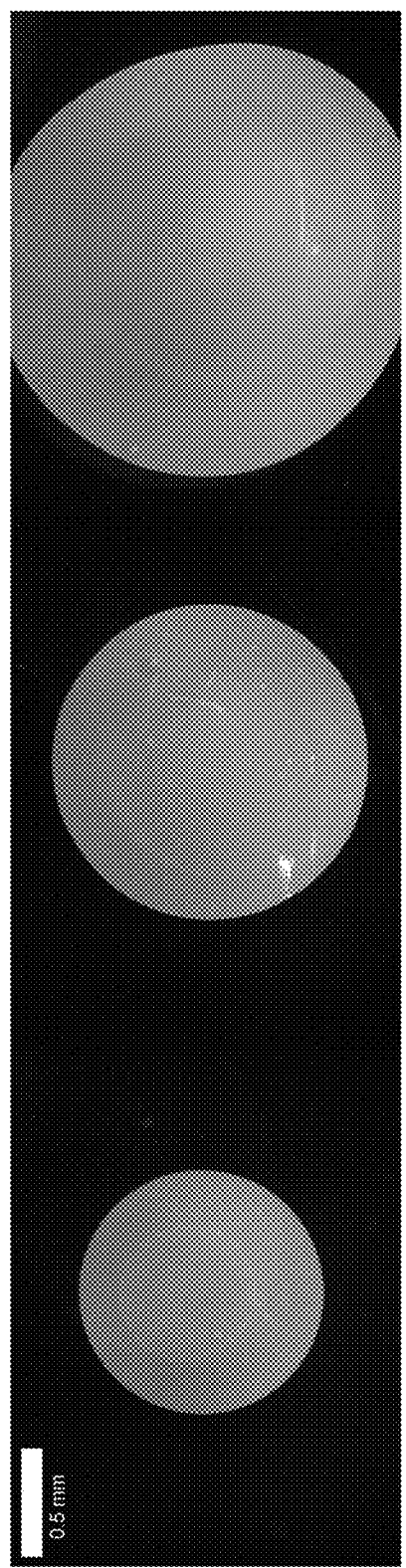
FIG. 6A is a photographic representation of differently sized streptavidin-presenting regions of a surface of a well plate, according to some of embodiments of the disclosure. Fluorescently labelled regions 193, 195, 197 illustrate the precision control for size and boundaries.

In some embodiments, the reagent including the biotin moiety linked to the reactive group may be a copper-dependent Click coupling reagent. Following the reaction of the biotin-containing copper-dependent Click coupling reagent with the reactive moieties (e.g., azido moieties), the surface of the well plate may be contacted with a thiol-containing reagent or a copper-chelating reagent, to stop any further reaction of the copper dependent reagent. After the copper-dependent Click coupling reagent has been disabled, then the surface may be treated with the reagent comprising surface blocking ligands to permit clearly distinct regions, as shown in FIG. 6A, where covalently functionalized region 193, covalently functionalized region 195 and covalently functionalized region 197, labeled with fluorescently labeled binding pair, show the precise control of reagent deposition at will, having diameters of about 1.0 mm up to about 3-4 mm (See FIG. 6B).

Each of the surface blocking ligands may be any surface blocking ligand as described herein, and any suitable mixture of surface blocking ligands may be used. In some embodiments, the surface blocking ligands may include a hydrophilic or negatively charged moiety. In some variations, the surface blocking ligands may include polyethylene glycol (PEG) moieties.

In some embodiments, the method may further include contacting one or more surfaces of each of the one or more wells with a reagent comprising a ligand configured to provide adherence stimulation. This may typically be performed after introduction of the biotin-presenting region(s). In various embodiments, ligands providing adherence stimulation are introduced to the portion of the surface(s) outside of the biotin-presenting region Preparing a streptavidin-presenting covalently functionalized region of a surface of a well plate. A method of preparing a well plate comprising a surface having a streptavidin-presenting covalently functionalized region, includes contacting a portion of the surface of the well plate with a reagent including a streptavidin functionality linked to a reactive group or a reagent including a biotin moiety linked to a reactive group, wherein the reactive group is configured to react with reactive moieties (e.g., azido or alkynyl moieties) of the surface, and, when the reagent including the biotin moiety linked to the reactive group, subsequently contacting the portion of the surface with streptavidin, thereby forming a streptavidin-presenting functionalized region of the well plate. The method may further include contacting the surface of the well plate with a reagent including surface blocking ligands linked to a reactive group, wherein the reactive group is configured to react with reactive moieties (e.g., azido or alkynyl) of the surface, to form a blocking ligand-modified region of the surface. When a reagent including a biotin moiety linked to the reactive group is used, introduction of streptavidin follows introduction of the biotin-presenting surface, where streptavidin binds to the biotin moiety.

In some embodiments, the blocking ligand-modified region and the streptavidin-presenting region may cover the entire surface. In various embodiments, the blocking ligand-modified region and the streptavidin-presenting region may be non-overlapping regions of the surface. Contacting the portion of the surface of the well plate with the reagent may further include contacting a surface within each of one or more wells of the well plate.

In some other embodiments, contacting may include contacting each of the one or more wells at a bottom surface of the corresponding well with the reagent including the streptavidin moiety linked to the reactive group or with the reagent including the biotin moiety linked to the reactive group. In some embodiments, the streptavidin-presenting covalently functionalized region may be formed only on the bottom surface of the corresponding well.

The streptavidin-presenting covalently functionalized region may have a density of streptavidin functionalities of at least 50/um2, e.g., from about 50 streptavidin groups/um$^2$ to about $8 \times 10^5$/um2, about $1 \times 10^2$/um2 to about $8 \times 10^5$/um2; about 50/um2 to about $5 \times 10^5$/um2; about $1 \times 10^2$/um2 to about $1 \times 10^5$/um2; about 50/um2 to about $5 \times 10^4$/um2; about $1 \times 10^2$/um2 to about $1 \times 10^4$/um2; about $1 \times 10^2$/um2 to about $5 \times 10^3$/um2; about $1 \times 10^2$/um2 to about $1 \times 10^3$/um2; about 50/um2 to about $5 \times 10^2$/um2; about 50/um2 to about $1 \times 10^2$/um2; or any value therebetween for the number of streptavidin groups/um2.

In some embodiments, the streptavidin—presenting covalently functionalized region may have an area of less than about 50% of an area of the bottom of the at least one well. In some embodiments, an area of the streptavidin-presenting covalently functionalized region may be less than about 25%, less than about 15%, less than about 10%, less than about 5%, less than about 2%, or less than about 1% of the area of the bottom of the at least one well. An area of the streptavidin-presenting covalently functionalized region has an area of less than about 35 mm$^2$, about 20 mm$^2$, about 12 mm$^2$, about 5 mm$^2$, less than about 2 mm$^2$, or less than about 1 mm$^2$. In some embodiments, the streptavidin-presenting covalently functionalized region may have a dimension of about 0.5 mm to about 4.0 mm (e.g., about 1.0 mm to about 35 mm, or about 1.5 mm to about 3.0 mm). In some embodiments, the streptavidin-presenting covalently functionalized region may be substantially circular and has a diameter of about 0.5 mm to about 4.0 mm (e.g., about 1.0 mm to about 35 mm, or about 1.5 mm to about 3.0 mm).

In some embodiments, contacting may include contacting a plurality of regions of the bottom of each of the one or more wells with the reagent comprising the streptavidin moiety linked to the reactive group or with the reagent comprising the biotin moiety linked to the reactive group (followed by reaction with streptavidin, to bind with the just-introduced biotin moieties), to produce a plurality of streptavidin-presenting regions in each of the one or more wells.

In some embodiments, the reagent comprising the streptavidin moiety linked to the reactive group or the reagent comprising the biotin moiety linked to the reactive group may be a copper-dependent Click coupling reagent, and the reaction may be followed by contacting the surface of the well plate with a thiol-containing reagent or a copper-chelating reagent to inactivate any copper dependent Click coupling reagent. This may include treating each of the one or more wells where a copper dependent Click coupling reaction has been performed. Subsequently, the reaction to introduce the surface blocking ligands, which includes contacting the surface with the reagent comprising surface blocking ligands may be performed.

Each of the surface blocking ligands may be any surface blocking ligand as described herein, and any suitable mixture of surface blocking ligands may be used. In some embodiments, the surface blocking ligands may include a hydrophilic or negatively charged moiety. In some variations, the surface blocking ligands may include polyethylene glycol (PEG) moieties.

In some embodiments, the method may further include contacting one or more surfaces of each of the one or more wells with a reagent comprising a ligand configured to provide adherence stimulation. This is typically performed after introduction of the streptavidin-presenting region(s). In various embodiments, ligands providing adherence stimulation are introduced to the portion of the surface(s) outside of the streptavidin-presenting region.

Preparing a streptavidin-presenting covalently functionalized region of a surface of a well plate. Another method of preparing a well plate comprising a surface having a streptavidin-presenting covalently functionalized region includes forming an reactive moiety-presenting (e.g., azido or alkynyl) covalently functionalized surface on the surface, wherein the reactive moiety-presenting covalently modified ligands of the surface further comprises a UV labile linking moiety, but otherwise is carried out as described above. The surface is then contacted with a reagent including a streptavidin moiety linked to a reactive group or a reagent comprising a biotin moiety linked to a reactive group, wherein the reactive group is configured to react with the reactive moieties of the reactive moiety-presenting surface, thereby forming a streptavidin-presenting functionalized region or a biotin-presenting functionalized surface, and further wherein when the reagent comprises the biotin moiety linked to the reactive group, subsequently contacting the portion of the well plate with streptavidin. The surface is then exposed to UV illumination through a mask configured to expose all surfaces outside of a portion of the surface. This cleaves the UV labile linkers of streptavidin or biotin modified surface ligands, anywhere the UV labile linkers of streptavidin or biotin modified surface ligands are exposed to the UV illumination, thereby forming a streptavidin-presenting covalently functionalized region of the well plate.

In some embodiments, forming the reactive moiety-presenting covalently modified surface includes reacting a reactive moiety-containing (e.g., azido or alkynyl) coupling reagent with surface exposed (e.g., oxide) moieties of the surface of the wellplate, wherein the reactive moiety containing-coupling reagent additionally includes the UV labile linking moiety. The surface of the well plate may be plasma cleaned before contacting the oxide moieties of the surface with the reactive moiety-containing coupling reagent.

Contacting the surface of the well plate with the reagent including the streptavidin moiety linked to the reactive group or the reagent including the biotin moiety may include contacting a surface within each of one or more wells of the well plate.

Each of the one or more wells may be contacted at a bottom surface of the corresponding well with the reagent including the streptavidin moiety linked to the reactive group or with the reagent including g the biotin moiety linked to the reactive group, thereby producing the streptavidin-presenting covalently functionalized region on the bottom surface of the corresponding well. In some embodiments, the streptavidin-presenting covalently functionalized region may be formed only on the bottom surface of the corresponding well. The streptavidin-presenting covalently functionalized region has a density of streptavidin functionalities of at least 50/um2, e.g., from about 50 streptavidin groups/um$^2$ to about 8×10$^5$/um2, about 1×10$^2$/um2 to about 8×10$^5$/um2; about 50/um2 to about 5×10$^5$/um2; about 1×10$^2$/um2 to about 1×10$^5$/um2; about 50/um2 to about 5×10$^4$/um2; about 1×10$^2$/um2 to about 1×10$^4$/um2; about 1×10$^2$/um2 to about 5×10$^3$/um2; about 1×10$^2$/um2 to about 1×10$^3$/um2; about 50/um2 to about 5×10$^2$/um2; about 50/um2 to about 1×10$^2$/um2; or any value therebetween for the number of streptavidin groups/um2.

Preparing a well plate comprising a surface having a lymphocyte activating covalently functionalized region. The method of preparing a lymphocyte activating covalently functionalized region of a surface of a well plate includes contacting a streptavidin-presenting covalently functionalized region of the well plate with a plurality of primary activating molecules each including a binding moiety, wherein the binding moieties of the primary activating molecules are configured to bind a binding site of streptavidin, thereby providing the lymphocyte activating covalently functionalized region. The method may further include contacting the surface of the well plate with a reagent including surface blocking ligands linked to a reactive group, wherein the reactive group is configured to react with reactive moieties of the surface, producing a blocking ligand-modified region of the surface. The blocking ligand-modified region and the lymphocyte activating covalently functionalized region may cover the entire surface. In some embodiments, the blocking ligand-modified region and the lymphocyte activating covalently functionalized region may be non-overlapping regions of the surface.

A streptavidin-presenting covalently functionalized region surface within each of one or more wells of the well plate may be contacted with the plurality of primary activating molecules. In some embodiments, contacting each of the one or more wells may further include contacting each of the one or more wells at a bottom surface of the corresponding well with the plurality of primary activating molecules, producing the lymphocyte activating covalently functionalized region on the bottom surface of the corresponding well.

In some embodiments, the lymphocyte activating covalently functionalized region may be formed only on the bottom surface of the corresponding well. Optionally, the lymphocyte activating covalently functionalized region may not be formed on a side wall of the one or more wells The lymphocyte activating covalently functionalized region so introduced may have an area of less than about 50% of an area of the bottom of the one or more wells. In some embodiments, an area of the lymphocyte activating covalently functionalized region may be less than about 25%, less than about 15%, less than about 10%, less than about 5%, less than about 2%, or less than about 1% of the area of the bottom of the one or more wells.

In some embodiment, an area of the lymphocyte activating covalently functionalized region has an area of less than about 35 mm$^2$, about 20 mm$^2$, about 12 mm$^2$, about 5 mm$^2$, less than about 2 mm$^2$, or less than about 1 mm$^2$. The lymphocyte activating covalently functionalized region may have a dimension of about 0.5 mm to about 4.0 mm (e.g., about 1.0 mm to about 35 mm, or about 1.5 mm to about 3.0 mm). In various embodiments, the lymphocyte activating covalently functionalized region may be substantially circular and has a diameter of about 0.5 mm to about 4.0 mm (e.g., about 1.0 mm to about 35 mm, or about 1.5 mm to about 3.0 mm).

In some embodiments, a plurality of lymphocyte activating covalently functionalized regions in each of the one or more wells may be introduced by contacting the streptavidin-presenting covalently functionalized region of the well plate at more than one locations within each well with the primary activating molecules. An area of each of the plurality of lymphocyte activating covalently functionalized regions may be less than about 5% of an area of the bottom of the one or more wells. In some embodiments, a total area of the plurality of lymphocyte activating covalently functionalized regions may be less than about 50%, about 25%, or about 10% of the area of the bottom of the one or more wells.

In some embodiments, the lymphocyte to be activated may be a T cell, a Natural Killer T (NKT) cell, or a B cell. In various embodiments, the first activating molecules may be any suitable activating molecule as described herein. In some embodiments, the first activating molecule may be a cell surface clusters of differentiation binding molecule, cell surface immunoglobulin binding molecule, T-cell receptor molecule activating molecule, TNF receptor superfamily binding molecule, chemokine receptor binding molecule, growth factor molecule, or an adhesion promoting molecule. In some embodiments, the plurality of first activating molecules comprise an MHC molecule, a protein or fragment thereof retaining cell surface clusters of differentiation binding activity, a protein or fragment thereof retaining T cell receptor binding activity, a protein or fragment thereof retaining TNF receptor superfamily binding activity, a protein or fragment thereof retaining chemokine receptor binding activity, a protein or fragment thereof retaining growth stimulatory activity or a protein or fragment thereof retaining adhesion promoting activity. In various embodiments, the plurality of first activating molecules comprise a protein or fragment thereof retaining cell surface clusters of differentiation binding activity, a protein or fragment thereof retaining growth stimulatory activity or a protein or fragment thereof retaining adhesion promoting activity.

The plurality of specifically bound first activating molecular ligands may have a density of at least about 1×10$^2$ molecules per square micron, about 5×10$^2$ molecules per square micron, about 1×10$^3$ molecules per square micron, about 5×10$^3$ molecules per square micron, about 1×10$^4$ molecules per square micron, about 5×10$^4$ molecules per square micron, about 1×10$^5$ molecules per square micron, or from about 1×10$^2$ to about 1×10$^5$ molecules per square micron n in the lymphocyte activating covalently functionalized region.

The method may further include contacting the streptavidin-presenting covalently functionalized region of the well plate with a plurality of second activating molecules each including a binding moiety, wherein the binding moieties of the second activating molecules are configured to bind a binding site of streptavidin, thereby providing a plurality of specifically bound second activating molecular ligands in the lymphocyte activating covalently functionalized region.

The second activating molecules may be T cell receptor (TCR) co-activating molecules, cell surface immunoglobulin binding molecules, TNF receptor superfamily binding molecule, chemokine receptor binding molecule, growth factor molecules, or adhesion promoting molecules. The plurality of specifically bound co-activating molecular ligands may have a density from may have a density of at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron or about $1\times10^3$ to about $1\times10^5$ molecules per square micron in the lymphocyte activating covalently functionalized region.

The method may further include contacting the surface of the well plate with a reagent including surface blocking ligands linked to a reactive group, wherein the reactive group is configured to react with reactive moieties of the surface, thereby providing a blocking ligand-modified region of the surface. In some embodiments, the blocking ligand-modified region and the antigen-presenting covalently functionalized region may cover the entire surface. In some embodiments, the blocking ligand-modified region and the lymphocyte activating covalently functionalized region may be non-overlapping regions of the surface.

Each of the surface blocking ligands may be any suitable surface blocking ligand as described herein. In some embodiments the surface blocking ligand may include comprises a hydrophilic or negatively charged moiety. In some embodiments, the surface blocking ligands may include polyethylene glycol (PEG) moieties.

Preparing a well plate comprising a surface having a lymphocyte activating covalently functionalized region. A method of preparing a wellplate comprising a surface having an antigen-presenting covalently functionalized region of the well plate for activating a T cell, includes contacting a streptavidin-presenting covalently functionalized region of the well plate with a plurality of primary activating molecules, each including a major histocompatibility complex (MHC) molecule configured to bind to a T cell receptor of the T cell and a binding moiety, wherein the binding moieties of the plurality of primary activating molecules, are configured to bind a binding site of streptavidin; and contacting a plurality of co-activating molecules, each including: a T cell receptor (TCR) co-activating molecule; or an adjunct TCR activating molecule, wherein the co-activating molecules each further include a binding moiety configured to bind a binding site of streptavidin, with a second plurality of binding moieties of the streptavidin-presenting covalently functionalized region of the well plate, thereby providing a plurality of specifically bound primary activating molecular ligands and a plurality of specifically bound co-activating molecular ligands of an antigen-presenting covalently functionalized region of the well plate.

The method may further include contacting the surface of the well plate with a reagent including surface blocking ligands linked to a reactive group, wherein the reactive group is configured to react with reactive moieties of the surface, thereby providing a blocking ligand-modified region of the surface. The blocking ligand-modified region and the antigen-presenting covalently functionalized region may cover the entire surface. In some embodiments, the blocking ligand-modified region and the antigen-presenting covalently functionalized region may be non-overlapping regions of the surface.

Contacting the streptavidin-presenting covalently functionalized region of the well plate with the plurality of primary activating molecules and the plurality of co-activating molecules may include contacting a surface within each of one or more wells of the well plate. In some embodiments, contacting each of the one or more wells may further include contacting each of the one or more wells at a bottom surface of the corresponding well with the plurality of primary activating molecules and the plurality of co-activating molecules, thereby producing the antigen-presenting covalently functionalized region on the bottom surface of the corresponding well. In some embodiments, the antigen-presenting covalently functionalized region may be formed only on the bottom surface of the corresponding well.

In some embodiments, the antigen-presenting covalently functionalized region may have an area of less than about 50% of an area of the bottom of the one or more wells. In some embodiments, an area of the antigen-presenting covalently functionalized region is less than about 25%, less than about 15%, less than about 10%, less than about 5%, less than about 2%, or less than about 1% of the area of the bottom of the one or more wells.

In some embodiments, an area of the antigen-presenting covalently functionalized region may have an area of less than about 35 mm$^2$, about 20 mm$^2$, about 12 mm$^2$, about 5 mm$^2$, less than about 2 mm$^2$, or less than about 1 mm$^2$. In some embodiments, the antigen-presenting covalently functionalized region may have a dimension of about 0.5 mm to about 4.0 mm (e.g., about 1.0 mm to about 35 mm, or about 1.5 mm to about 3.0 mm). In some embodiments, the antigen-presenting covalently functionalized region may be substantially circular and has a diameter of about 0.5 mm to about 4.0 mm (e.g., about 1.0 mm to about 35 mm, or about 1.5 mm to about 3.0 mm).

Contacting the streptavidin-presenting covalently functionalized region of the well plate with the plurality of primary activating molecules and the plurality of co-activating molecules may further include contacting a plurality of streptavidin-presenting covalently functionalized regions within each of one or more wells of the well plate, thereby producing a plurality of antigen-presenting covalently functionalized regions in each of the one or more wells. In some embodiments, an area of each of the plurality of antigen-presenting covalently functionalized regions may be less than about 5% of an area of the bottom of the one or more wells, and further wherein a total area of the plurality of antigen-presenting covalently functionalized regions is less than about 50%, about 25%, or about 10% of the area of the bottom of the one or more wells.

In some embodiments, the MHC molecule includes an MHC Class I protein sequence and a beta microglobulin protein sequence. In some embodiments, each of the plurality of primary activating molecules including an MHC molecule may further include an antigenic peptide. The antigenic peptide may be a tumor associated antigen, a viral antigen, a bacterial antigen, a fungal antigen, a protozoan antigen, or the like. In some embodiments, the tumor associated antigen may be SLC45A2, TCL1, VCX3A, MART1 or NYESO1.

In some embodiments, the protein sequence of the MHC molecule may be connected to the surface via a C-terminal connection of the protein sequence. For example, the MHC protein sequence may include a C-terminal BirA tag. The BirA tag permits site specific biotinylation. In some embodiments, the MHC molecule may include a biotin moiety and is attached to the surface via a noncovalent interaction with streptavidin. In various embodiments, the streptavidin is itself covalently bonded to the surface. In some embodiments, the streptavidin may be bonded to the surface through a series of about 5, 7, 9, 10, 11, 13, 15, 20, 25, 30, 35, 40, 45, 50, 55, 60, 65, 70, 75, 80, 90, 100, 200 bond lengths, or any number of bond lengths therebetween.

In various embodiments, the streptavidin may be noncovalently associated with the surface. The streptavidin may be noncovalently associated with a biotin moiety, and the biotin moiety may be covalently bonded to the surface. In various embodiments, the biotin moiety may be linked by a linker to the surface through about 5, 7, 9, 10, 11, 13, 15, 20, 25, 30, 35, 40, 45, 50, 55, 60, 65, 70, 75, 80, 85, 95, 100, 200 bond lengths, or any number of bond lengths therebetween.

The ratio of the primary activating molecules to the co-activating molecules may be about 1:1 to about 2:1; about 1:1; or about 3:1 to about 1:3.

In some embodiments, a ratio of the TCR co-activating molecules to the adjunct TCR activating molecules of the plurality of co-activating molecular ligands may be about 100:1 to about 1:100. In some embodiments, a ratio of the TCR co-activating molecules to the adjunct TCR activating molecules of the plurality of co-activating molecular ligands may be 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about". In some embodiments, the ratio of the TCR co-activating molecules to the adjunct TCR activating molecules of the plurality of co-activating molecular ligands may be from about 20:1 to about 1:20 or about 3:1 to about 1:3.

The plurality of specifically bound primary activating molecular ligands may have a density of at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, or from about $1\times10^2$ to about $1\times10^5$ molecules per square micron in the antigen-presenting covalently functionalized region.

The plurality of specifically bound co-activating molecular ligands may have a density from at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, or about $1\times10^3$ to about $1\times10^5$ molecules per square micron on the antigen-presenting synthetic surface in the antigen-presenting covalently functionalized region In some embodiments, the T cell receptor (TCR) co-activating molecule may include a CD28 binding protein or a fragment thereof, which retains binding ability to CD28. The CD28 binding protein or the fragment thereof further may include a site-specific C-terminal biotin moiety. In some embodiments, the T cell receptor (TCR) co-activating molecule may include a CD80 molecule or a fragment thereof, wherein the fragment retains binding activity to CD28. In some embodiments, the T cell receptor (TCR) co-activating molecule may include an anti-CD28 antibody or a fragment thereof.

In some embodiments, the adjunct TCR activating molecule may include a CD2 binding protein. The CD2 binding protein or the fragment thereof may further include a site-specific C-terminal biotin moiety. In some embodiments, the adjunct TCR activating molecule may include a CD58 molecule or fragment thereof, wherein the fragment retains binding activity with CD2. In some embodiments, the adjunct TCR activating molecule may include an anti-CD2 antibody or a fragment thereof.

Each of the surface blocking ligands may be any suitable surface blocking ligand as described herein. In some embodiments the surface blocking ligand may include comprises a hydrophilic or negatively charged moiety. In some embodiments, the surface blocking ligands may include polyethylene glycol (PEG) moieties.

Method of preparing a culture plate/culture flask with the covalently functionalized regions described above. As another embodiment of a well plate, culture plates (e.g., round culture plates) and/or culture flasks may also have any of the covalently functionalized surfaces introduced therein, such as the reactive-moiety presenting (e.g., azido-presenting or alkynyl-presenting), biotin-presenting, streptavidin-presenting, antigen-presenting, and/or lymphocyte-activating covalently functionalized region. An azido-presenting covalently functionalized region may be introduced to the entire culture plate/flask similarly as described above. The culture plate/flask may or may not be plasma cleaned. All or parts of the culture plate/flask may be exposed to the reactive moiety functionalization reagent and functionalized. Any sort of suitable spotting tool may be used to introduce the subsequent biotin- and/or streptavidin-presenting regions within a culture plate in an array of first regions. A micromanipulator may be inserted within a culture flask to introduce the subsequent biotin- and/or streptavidin-presenting covalently functionalized regions in an array. Both the culture plate and culture flasks may have an array of covalently functionalized regions, with each region having a size (e.g., an area) suitable for activating lymphocytes as described herein, and the surrounding region and other surfaces (e.g., remaining sides of a culture flask or side walls of a culture plate) may be passivated by introducing surface blocking ligands, as described herein. Activating and co-activating molecular ligands may be introduced similarly as for the well plates described above, and the antigen-presenting or lymphocyte-activating culture plate/culture flask may be used to activate lymphocytes as described in the methods herein.

Click Chemistry and Reagents. Covalent bonds may be formed by reacting an alkyne, such as an acyclic alkyne, with an azide. For example, a "Click" cyclization reaction may be performed, which is catalyzed by a copper (I) salt. When a copper (I) salt is used to catalyze the reaction, the reaction mixture may optionally include other reagents which can enhance the rate or extent of reaction. When an alkyne, e.g., of a surface modifying reagent or a functionalized surface is a cyclooctyne, the "Click" cyclization reaction with an azide of the corresponding functionalized surface or the surface modifying reagent may be copper-free. A "Click" cyclization reaction can thereby be used to couple a surface modifying ligand to a functionalized surface to form a covalently modified surface.

Copper catalysts. Any suitable copper (I) catalyst may be used. In some embodiments, copper (I) iodide, copper (I) chloride, copper (I) bromide or another copper (I) salt is used as the copper (I) catalyst. In other embodiments, a copper (II) salt may be used in combination with a reducing agent, such as ascorbate, to generate a copper (I) species in situ. Copper sulfate or copper acetate are non-limiting examples of a suitable copper (II) salt. In other embodiments, a reducing agent such as ascorbate may be present in combination with a copper (I) salt to ensure sufficient copper (I) species during the course of the reaction. Copper metal may be used to provide Cu(I) species in a redox reaction also producing Cu(II) species. Coordination complexes of copper such as [CuBr(PPh$_3$)$_3$], silicotungstate complexes of copper, [Cu(CH$_3$CN)$_4$]PF6, or (EtO)$_3$P CuI may be used. In yet other embodiments, silica supported copper catalyst, copper nanoclusters or copper/cuprous oxide nanoparticles may be employed as the catalyst.

Other reaction enhancers. As described above, reducing agents such as sodium ascorbate may be used to permit copper (I) species to be maintained throughout the reaction, even if oxygen is not rigorously excluded from the reaction. Other auxiliary ligands may be included In the reaction mixture, to stabilize the copper (I) species. Triazolyl containing ligands can be used, including but not limited to tris(benzyl~1H-1,2,3-triazol-4-yl) methylamine (TBTA) or 3 [tris(3-hydroxypropyltriazolylmethyl)amine (THPTA). Another class of auxiliary ligand that can be used to facilitate reaction is a sulfonated bathophenanthroline, which is water soluble, as well, and can be used when oxygen can be excluded.

Methods of Use

Activating T lymphocytes using an antigen-presenting covalently functionalized region of a surface of a well plate. A method of activating T lymphocytes (T cells) includes contacting a plurality of T cells with an antigen-presenting covalently functionalized region of a surface of one or more wells of a well plate. The antigen-presenting covalently functionalized region can include: a plurality of primary activating molecular ligands, each including a major histocompatibility (MHC) molecule (e.g., Class I or Class II) configured to bind to a T cell receptor of the T cell, wherein each of the plurality of primary activating molecular ligands is linked to the surface of the one or more wells; and a plurality of co-activating molecular ligands, each including a T cell receptor (TCR) co-activating molecule or an adjunct TCR activating molecule, wherein each of the co-activating molecular ligands is linked to the surface of the one or more wells. The method of activating can further include culturing the plurality of T cells in contact with the antigen-presenting covalently functionalized region of the surface, thereby converting at least a portion of the plurality of T cells to activated T cells. In some embodiments, the T cells placed in contact with the antigen-presenting covalently functionalized surface include CD8+ T cells.

In some embodiments, the antigen-presenting covalently functionalized region of the surface of one or more wells of the well plate is any antigen-presenting covalently functionalized region as described herein, with any combination of features.

In some embodiments, the plurality of co-activating molecular ligands may include TCR co-activating molecules and adjunct TCR activating molecules. A ratio of the TCR co-activating molecules to the adjunct TCR activating molecules of the plurality of co-activating molecular ligands may be about 100:1 to about 1:100. The ratio of the TCR co activating molecules to the adjunct TCR activating molecules of the plurality of co-activating molecular ligands may be 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about". In various embodiments, the ratio of the TCR co-activating molecules to the adjunct TCR activating molecules of the plurality of co-activating molecular ligands may be from about 20:1 to about 1:20, or about 3:1 to about 1:3.

In some embodiments, the plurality of MHC molecules each may include an MHC Class I protein sequence and a beta microglobulin protein sequence. In some embodiments, the protein sequence of the MHC molecule may be connected to the antigen-presenting covalently functionalized region of the surface via a C-terminal connection of the protein sequence. In some embodiments, the MHC molecule may further include an antigenic peptide. In some embodiments, the antigenic peptide is a tumor associated antigen, a viral antigen, a bacterial antigen, a fungal antigen, a protozoan antigen, or the like. In some embodiments, the tumor associated antigen is SLC45A2, TCL1, VCX3A, MART1 or NYESO1. In various embodiments, the MHC molecule may include a biotin moiety and is attached to the antigen-presenting covalently functionalized region of the surface via a noncovalent interaction with streptavidin.

In some embodiments, the streptavidin may be itself covalently bonded to the antigen-presenting covalently functionalized region of the surface. The streptavidin may be bonded to the surface through a series of about 5, 7, 9, 10, 15, 20, 25, 30, 35, 40, 45, 50, 55, 60, 65, 70, 75, 80, 85, 95, 100, 200 bond lengths, or any number of bond lengths therebetween. In other embodiments, the streptavidin may be noncovalently associated with the antigen-presenting covalently functionalized region of the surface. In some embodiments, the streptavidin may be noncovalently associated with a biotin moiety, and the biotin is covalently bonded to the antigen-presenting covalently functionalized region of the surface. The biotin moiety may be linked by a linker to the surface through a series of 2 about 5 7, 9, 10 15, 20, 25, 30, 35, 40, 45, 50, 55, 60, 65, 70, 75, 80, 85, 95, 100, 200 bond lengths, or any number of bond lengths therebetween.

In some embodiments, each of the plurality of co-activating molecule ligands may be linked to the antigen-presenting covalently functionalized region of the surface.

In some embodiments, the T cell receptor (TCR) co-activating molecule may include a CD28 binding protein or a fragment thereof, which retains binding ability to CD28. The CD28 binding protein or the fragment thereof may further include a site-specific C-terminal biotin moiety. In some other embodiments, the T cell receptor (TCR) co-activating molecule may include a CD80 molecule or a fragment thereof, wherein the fragment retains binding activity to CD28. The T cell receptor (TCR) co-activating molecule may include an anti-CD28 antibody or a fragment thereof.

In various embodiments, the adjunct TCR activating molecule may include a CD2 binding protein. The CD2 binding protein or the fragment thereof further may include a site-specific C-terminal biotin moiety. In various embodiments, the adjunct TCR activating molecule may include a CD58 molecule or fragment thereof, wherein the fragment retains binding activity with CD2. The adjunct TCR activating molecule may include an anti-CD2 antibody or a fragment thereof.

The specifically bound primary activating molecular ligands may have a density of at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, or from about $1\times10^2$ to about $1\times10^5$ molecules per square micron in the antigen-presenting covalently functionalized region of the surface. The specifically bound co-activating molecular ligands may have a density from at least about $1\times10^2$ molecules per square micron, about $5\times10^2$ molecules per square micron, about $1\times10^3$ molecules per square micron, about $5\times10^3$ molecules per square micron, about $1\times10^4$ molecules per square micron, about $5\times10^4$ molecules per square micron, about $1\times10^5$ molecules per square micron, or about $1\times10^3$ to about $1\times10^5$ molecules per square micron in the antigen-presenting covalently functionalized region of the surface. In some embodiments, a ratio of the primary activating molecular ligands to the co-activating molecular ligands on the covalently modified surface may be about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1. In some embodiments, a ratio of the TCR co-activating molecules to the adjunct TCR activating molecules of the plurality of co-activating molecular ligands may be about 3:1 to about 1:3. In some embodiments, a ratio of the TCR co-activating molecules to the adjunct TCR activating molecules of the plurality of co-activating molecular ligands may be about 2:1 to about 1:2. In other embodiments, a ratio of the TCR co-activating molecules to the adjunct TCR activating molecules of the plurality of co-activating molecular ligands may be about 1:1.

The method may further include contacting the plurality of T cells with a plurality of adhesion-stimulating molecular ligands including an ICAM molecule, wherein each of the plurality of adhesion-stimulating molecular ligands is attached to a region outside of the antigen-presenting covalently functionalized region of the surface of the well plate. In some embodiments, the plurality of adhesion-stimulating molecular ligands may be covalently attached to the region outside of the antigen-presenting covalently functionalized region of the surface of the well plate.

In some embodiments, the method may further include contacting the plurality of T cells with a plurality of growth stimulatory molecular ligands. Each of the growth stimulatory molecular ligands may include a growth factor receptor ligand. In some embodiments, the growth factor receptor ligand may include IL-21 or a fragment thereof.

In some embodiments, contacting the plurality of T cells with the plurality of growth stimulatory molecular ligands may be performed after a first period of culturing of at least one day. Culturing the T cells in contact with the antigen-presenting synthetic surface may be performed for a period from about four days to about seven days.

In some embodiments, the method further includes completing a first period of activation in contact with the antigen-presenting covalently functionalized region of the surface; and, culturing the plurality of activated T cells in contact with the antigen-presenting covalently functionalized region of the surface for a second period of culturing, thereby providing an expanded plurality of activated T cells. A second plurality of growth stimulatory molecular ligands may be added during the second culturing period. A plurality of IL-2 molecules and a plurality of IL-7 molecules may be added to contact the activated T cells for a remainder of the second culturing period. In some embodiments, culturing in contact with the antigen-presenting covalently functionalized region of the surface for the second culturing may be performed for a period from about four days to about seven days.

The method may further include completing the second period of activation in contact with the antigen-presenting covalently functionalized region of the surface; and, culturing the expanded plurality of activated T cells in contact with the antigen-presenting covalently functionalized region of the surface for a third period of culturing, thereby providing a plurality of highly activated T cells. A third plurality of growth stimulatory molecular ligands may be added during the third culturing period. In some embodiments, a plurality of IL-2 molecules and a plurality of IL-7 molecules may be added to contact the activated T cells for a remainder of the third culturing period. Culturing in contact with the antigen-presenting covalently functionalized region of the surface may be performed for a third period from about four days to about seven days.

Phenotype and products. In some embodiments, the T lymphocytes being activated include CD8+ T lymphocytes, such as naive CD8+ T lymphocytes. In some embodiments, the T lymphocytes being activated may be enriched for CD8+ T lymphocytes, such as naive CD8+ T lymphocytes, Alternatively, in some embodiments, the T lymphocytes being activated may include CD4+ T lymphocytes, such as naive CD4+ T lymphocytes. In some embodiments, the T lymphocytes being activated are enriched for CD4+ T lymphocytes, such as naïve CD4+ T lymphocytes, CD4+ T lymphocytes can be used, e.g., if T cells specific for a Class II-restricted antigen are desired.

In some embodiments, the method produces activated T lymphocytes that are CD45RO+. In some embodiments, the method produces activated T lymphocytes that are CD28 positive. In some embodiments, the method produces activated T lymphocytes that are CD28+ CD45RO+. In some embodiments, the method produces activated T lymphocytes that are CD197+. In some embodiments, the method produces activated T lymphocytes that are CD127+. In some embodiments, the method produces activated T lymphocytes that are positive for CD28, CD45RO, CD 127 and CD 197, or at least any combination of three of the foregoing markers, or at least any combination of two of the foregoing markers. The activated T lymphocytes with any of the foregoing phenotypes can further be CD8+. In some embodiments, any of the foregoing phenotypes that is CD28+ comprises a CD28high phenotype.

In some embodiments, the method produces a population of T cells comprising antigen-specific T cells, wherein at least 65%, 70%, 75%, 80%, 85%, 86%, 87%, 88%, 89%, 90%, 91%, 92%, 93%, 94%, 95%, 96%, 97%, or 98% of the antigen-specific T cells are CD45RO+/CD28 High cells, wherein each of the foregoing values can be modified by "about."

Alternatively or in addition, in some embodiments, the method produces a population of T cells wherein at least 1%, 1.5%, 2%, 3,%, 4%, 5%, 6%, 7%, 8%, 9%, or 10% of the T cells are antigen-specific T cells; or wherein 1%-2%, 2%-3%, 3%-4%, 4%-5%, 5%-6%, 6%-7%, 7%-8%, 8%-9%, 9%-10%, 10%-11%, or 11%-12% of the T cells are antigen-specific T cells, wherein each of the foregoing values can be modified by "about." The content of the population of T cells can be determined on the "crude" product of the method following contact with the antigen-presenting surface and optionally further expansion steps, i.e., before/without enriching or separating product T cells having a particular phenotype. The determination of antigen-specificity and/or T cell marker phenotype can exclude dead cells. In some embodiments, the method provides a population of T cells in which the fraction of T cells that are antigen-specific is increased relative to the starting population.

Treating a subject using cells activated using the method described herein. A method of treating a subject in need of treating a cancer includes obtaining a plurality of T lymphocytes (T cells) from the subject; contacting the plurality of T cells with a surface of a well plate including an antigen-presenting covalently functionalized region, wherein the antigen-presenting covalently functionalized region includes a plurality of major histocompatibility complex (MHC) molecules (e.g., Class I or Class II) configured to bind to a T cell receptor of each of the plurality of T cells, wherein the MHC molecules include an antigen specific for the cancer of the subject; producing a plurality of activated T cells, where the activation is configured to be specific against the cancer of the subject; separating the plurality of specific activated T cells from unactivated cells; and, introducing the plurality of antigen-specific activated T cells into the subject.

The well plate having a surface including the antigen-presenting covalently functionalized region may be a well plate including any antigen-presenting covalently functionalized region as described herein, and may have any combination of features. The well plate having a surface including the antigen-presenting covalently functionalized region may be produced by any method described herein and in any combination of steps.

A method of treating a subject in need of treating a cancer includes obtaining a plurality of T lymphocytes (T cells) from the subject; producing a plurality of activated T cells by the method like any method described herein, wherein the activation is configured to be specific against the cancer of the subject; separating the plurality of specific activated T cells from unactivated cells; and, introducing the plurality of antigen-specific activated T cells into the subject.

Also provided is a use of a plurality of specific activated T lymphocytes for the manufacture of a medicament for treating a subject in need of treating a cancer, wherein the plurality of specific activated T lymphocytes were produced by a method described herein. Also provided is a use of a plurality of specific activated lymphocytes for the manufacture of a medicament for treating a subject in need of treating a cancer, wherein the plurality of specific activated lymphocytes were produced by a method described herein. Also provided is a use of a plurality of specific activated lymphocytes for the manufacture of a medicament for treating a subject in need of treating a protein deficiency disorder or immunological disorders, wherein the plurality of specific activated lymphocytes were produced by a method described herein.

In some embodiments, separating the plurality of specific activated lymphocytes may further include detecting surface biomarkers of the specifically activated lymphocytes.

In some embodiments, the specifically activated lymphocytes are autologous (i.e., derived from the subject to which they are to be administered), and may be rapidly expanded using the surfaces and methods of activation described herein.

In various embodiments, the methods or the preparation of the plurality or population of specific activated T lymphocytes may further include rapidly expanding the activated T lymphocytes to provide an expanded population of activated T lymphocytes. In some embodiments, the rapid expansion may be performed after separating the specifically activated T lymphocytes from the non-activated T lymphocytes. The generation of sufficient levels of T lymphocytes may be achieved using rapid expansion methods described herein or known in the art. See, e.g., the Examples below; Riddell, U.S. Pat. No. 5,827,642; Riddell et al., U.S. Pat. No. 6,040,177, and Yee and LI, PCT Patent App. Pub. No. WO2009/045308 A2.

Uses of T cells in treatment of human subjects (e.g., for adoptive cell therapy) are known in the art. T cells prepared according to the methods described herein can be used in such methods. For example, adoptive cell therapy using tumor-infiltrating lymphocytes including MART-1 antigen specific T cells have been tested in the clinic (Powell et al., Blood 105:241-250, 2005). Also, administration of T cells coactivated with anti-CD3 monoclonal antibody and IL-2 was described in Chang et al., J. Clinical Oncology 21:884-890, 2003. Additional examples and/or discussion of T cell administration for the treatment of cancer are provided in Dudley et al. Science 298:850-854, 2002; Roszkowski et al., Cancer Res 65(4): 1570-76, 2005; Cooper et al. Blood 101: 1637-44, 2003; Yee, US Patent App, Pub. No. 2006/0269973; Yee and Li, PCI Patent App. Pub. No, WO2009/045308 A2; Gruenberg et al., US Patent App. Pub, No. 2003/0170238: Rosenberg, U.S. Pat. No. 4,690,915: and Alajez et al., Blood 105:4583-89, 2005.

Interest in therapeutic use of NK cells or NK CAR cells has increased, and these cell types are being investigated for a wide range of haematological and solid tumors, as described in EBioMedicine 39:1-2, 2019.

B lymphocytes have recently been reported for use as engineered B cells, for delivery of therapeutic proteins for a wide range of applications including protein deficiency disorders, such as hemophilia, and other immunotherapies.

In some embodiments, the cells are formulated by first harvesting them from their culture medium as used in the methods of activation described herein, and then washing and concentrating the cells in a medium and container system suitable tor administration (a "pharmaceutically acceptable" earner) in a treatment-effective amount. Suitable infusion medium can be any Isotonic medium formulation, typically normal saline, Normosoi R (Abbott) or Plasma-Lyte A (Baxter), but also 5% dextrose in water or Ringer's lactate can be utilized. The infusion medium can be supplemented with human serum albumin.

In some embodiments, the number of cells in the composition is at least $10^9$ or at least $10^{10}$ cells, in some embodiments, a single dose can comprise at least 10 million, 100 million, 1 billion, or 10 billion cells. The number of cells administered is indication specific, patient specific (e.g., size of patient), and will also vary with the purity and phenotype of the administered cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mLs or less, even 250 mLs or 100 mLs or less. Hence the density of the desired cells may be greater than $10^6$ cells/mi, greater than $10^7$ cells/mi, or $10^8$ cells/ml or greater. The clinically relevant number of Immune cells can be apportioned into multiple infusions that cumulatively equal or exceed $10^9$, $10^{10}$ or $10^{11}$ cells.

In some embodiments, T lymphocytes described herein or prepared according to a method described herein may be used to confer immunity to individuals against a tumor or cancer cells. By 'immunity" is meant a lessening of one or more physical symptoms associated with cancer cells or a tumor against an antigen of which the lymphocytes have been activated. The cells may be administered by infusion, with each Infusion in a range of at least $10^6$ to $10^{10}$ cells/m2, e.g., in the range of at least $10^7$ to $10^9$ cells/m2. The cells may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by examination.

Following the transfer of cells back into patients, methods may be employed to maintain their viability by treating patients with cytokines that could include IL-21 and IL-2 (Bear et al., Cancer Immunol. Immunother. 50\2.69-74, 2001; and Schultze et al., Br. J. Haematol. 113:455-60, 2001). In another embodiment, cells are cultured in the presence of IL-21 before administration to the patient. See, e.g., Yee, US Patent App. Pub. No. 2006/0269973, IL-21 can increase T cell frequency in a population comprising activated T cells to levels that are high enough for expansion and adoptive transfer without further antigen-specific T cell enrichment. Accordingly, such a step can further decrease the time to therapy and/or obviate a need for further selection and/or cloning.

Kits

Kit for preparing a well plate having a surface including an antigen-presenting covalently functionalized region. A kit for preparing a well plate comprising a surface having an antigen-presenting covalently functionalized region includes a well plate having a surface including a biotin-presenting covalently functionalized region; and a surface functionalization reagent comprising streptavidin. In some embodiments, the well plate having the surface including the biotin-presenting covalently functionalized region may be any well plate having the surface including the biotin-presenting covalently functionalized region as described herein, and have any combination of features.

In some embodiments, the kit may further include a first activating reagent including a plurality of major histocompatibility complex (MHC) molecules (e.g., Class I or Class II) configured to bind with a T cell receptor of the T cell, and further wherein the MHC molecules are configured to bind to a binding site of streptavidin. In some embodiments, each of the plurality of MHC molecules may further include at least one biotin functionality.

In some embodiments, the kit may further include a reagent including co-activating molecules, each configured to bind a binding site of streptavidin, and wherein each of the co-activating molecules may be a T cell receptor (TCR) co-activating molecule or an adjunct TCR activating molecule. In some embodiments, the plurality of co-activating molecules may include T cell receptor (TCR) co-activating molecules and adjunct TCR activating molecules. In some embodiments, a container containing the reagent including the co-activating molecules may contain a ratio of the TCR co-activating molecules to the adjunct TCR activating molecules from about 20:1 to about 1:20. In some embodiments, the TCR co-activating molecules may be agonists of a CD28 receptor. In some embodiments, the adjunct TCR activating molecules are agonists of a CD2 receptor.

In some embodiments, the kit may further include a surface blocking reagent comprising a surface blocking moiety linked to a reactive group configured to react with the azido moieties. In some embodiments, the surface blocking moiety may include a hydrophilic or negatively charged moiety. In some embodiments, the surface blocking reagent may include polyethylene glycol (PEG) moieties.

In some embodiments, the kit may further include a reagent including growth stimulatory molecules, wherein each growth stimulatory molecule includes a growth factor receptor ligand. In some embodiments, the growth factor receptor ligand may include IL-21 or a fragment thereof. In some embodiments, the kit may further include a second growth stimulatory molecule comprising IL-7 or IL-2.

Kit for preparing a well plate. In other variations, a kit for preparing a well plate including a surface having an antigen-presenting covalently functionalized region, includes a well plate comprising a surface comprising an azido-presenting covalently functionalized region; and a first surface functionalization reagent. In some embodiments, the well plate comprising the surface having the azido-presenting covalently functionalized region may be any well plate including a surface having an azido-presenting covalently functionalized region like any described herein.

In some embodiments, the first surface functionalization reagent may include a reagent comprising a biotin moiety linked to a reactive group, wherein the reactive group is configured to react with the azido moieties of the surface. In some embodiments, the kit may further include a second surface functionalization reagent comprising streptavidin, which is configured to bind with a biotin moiety.

In some embodiments, the first functionalization reagent comprises a streptavidin moiety linked to a reactive group, wherein the reactive group is configured to react with azido moieties.

In some embodiments, the kit may further include a surface blocking reagent comprising a surface blocking moiety linked to a reactive group configured to react with the azido moieties. In some embodiments, the surface blocking moiety may include a hydrophilic or negatively charged moiety. In some embodiments, the surface blocking reagent may include polyethylene glycol (PEG) moieties.

In some embodiments, the kit may further include a first activating reagent including a plurality of major histocompatibility complex (MHC) molecules (e.g., Class I or Class II) configured to bind with a T cell receptor of the T cell, and further wherein the MHC molecules are configured to bind to a binding site of streptavidin. In some embodiments, each of the plurality of MHC molecules may further include at least one biotin functionality.

In some embodiments, the kit may further include a reagent including co-activating molecules, each configured to bind a binding site of streptavidin, and wherein each of the co-activating molecules may be a T cell receptor (TCR) co-activating molecule or an adjunct TCR activating molecule. In some embodiments, the plurality of co-activating molecules may include T cell receptor (TCR) co-activating molecules and adjunct TCR activating molecules. In some embodiments, a container containing the reagent including the co-activating molecules may contain a ratio of the TCR co-activating molecules to the adjunct TCR activating molecules from about 20:1 to about 1:20. In some embodiments, the TCR co-activating molecules may be agonists of a CD28 receptor. In some embodiments, the adjunct TCR activating molecules are agonists of a CD2 receptor.

In some embodiments, the kit may further include a reagent including growth stimulatory molecules, wherein each growth stimulatory molecule includes a growth factor receptor ligand. In some embodiments, the growth factor receptor ligand may include IL-21 or a fragment thereof. In some embodiments, the kit may further include a second growth stimulatory molecule comprising IL-7 or IL-2.

Kit for preparing a well plate A kit for preparing a well plate comprising a surface having an antigen-presenting covalently functionalized region for antigen-specific activation of a T lymphocyte (T cell) includes a well plate including a surface having a streptavidin-presenting covalently functionalized region; and a first activating reagent comprising a plurality of major histocompatibility complex (MHC) molecules (e.g., Class I or Class II) configured to bind with a T cell receptor of the T cell, and further wherein the MHC molecules are configured to bind to a binding site of streptavidin. In some embodiments, the well plate including a surface having a streptavidin-presenting covalently functionalized region may be like any well plate including a surface having a streptavidin-presenting covalently functionalized region as described herein, and may have any combination of features.

In some embodiments, each of the plurality of MHC molecules may further include at least one biotin functionality.

In some embodiments, the kit may further include a reagent including a plurality of co-activating molecules, each having a binding moiety configured to bind a binding site of streptavidin, and wherein each of the co-activating molecules includes a T cell receptor (TCR) co-activating molecule or an adjunct TCR activating molecule.

In some embodiments, the kit may further include a reagent including co-activating molecules, each configured to bind a binding site of streptavidin, and wherein each of the co-activating molecules may be a T cell receptor (TCR) co-activating molecule or an adjunct TCR activating molecule. In some embodiments, the plurality of co-activating molecules may include T cell receptor (TCR) co-activating molecules and adjunct TCR activating molecules. In some embodiments, a container containing the reagent including the co-activating molecules may contain a ratio of the TCR co-activating molecules to the adjunct TCR activating molecules from about 20:1 to about 1:20. In some embodiments, the TCR co-activating molecules may be agonists of a CD28 receptor. In some embodiments, the adjunct TCR activating molecules are agonists of a CD2 receptor.

In some embodiments, the kit may further include a surface blocking reagent comprising a surface blocking moiety linked to a reactive group configured to react with the azido moieties. In some embodiments, the surface blocking moiety may include a hydrophilic or negatively charged moiety. In some embodiments, the surface blocking reagent may include polyethylene glycol (PEG) moieties.

In some embodiments, the kit may further include a reagent including growth stimulatory molecules, wherein each growth stimulatory molecule includes a growth factor receptor ligand. In some embodiments, the growth factor receptor ligand may include IL-21 or a fragment thereof. In some embodiments, the kit may further include a second growth stimulatory molecule comprising IL-7 or IL-2.

EXAMPLES

Experiment 1. Preparation of well plates. Polystyrene well plates (Falcon 96 Well Round Bottom, Falcon 96 Well Flat Bottom, Falcon 6 Well Flat Bottom, Costar 96 Well V Bottom) were placed in an oxygen plasma cleaner (Nordson March AP-300) which was evacuated to 50 mTorr and purged with oxygen at 440 sccm to a pressure of 190 mTorr. The plates were treated with 100 W plasma for 60 seconds.

Experiment 2. Chemical vapor deposition (CVD) of plates. 7-azidoheptyl-trimethoxysilane was synthesized in house. Three 20 mL aluminum pans were filled with 300 mg of the silane and three were filled with 333 mg $MgSO_4$ $(H_2O)_7$. One pan of each reagent was placed on each of the three shelves in a vacuum oven. Well plates and witness samples were placed on each shelf. The oven was sealed and evacuated to 250 mTorr. The temperature was raised to 75° C. and CVD proceeded overnight (~18 hours). Following the CVD process the oven was purged and the well plates and witness samples were removed.

Experiment 3. Treatment of azido-modified well plates with dibenzylcyclooctynyl (DBCO)-polyethyleneglycol$_{13}$ (PEG13)-streptavidin (SAV) provided functionalized well plate with a restricted region of functionalization. A 5 μM solution of DBCO-PEG13-SAV was synthesized as described in PCT/US2018/043146, filed on Jul. 20, 2018, which disclosure is herein incorporated by reference in its entirety. DBCO-PEG13-SAV is a copper-less Click reagent having a dibenzocyclooctynyl coupling moiety linked via a polyethylene glycol linker (thirteen PEG units) covalently attached to streptavidin, and was prepared in PBS/0.02% sodium azide, to provide SAV covalently bound to well plates, as shown schematically in FIG. 1B. The DBCO-PEG13-SAV solution was added to wells in volumes ranging from 250 nL to 50 uL and allowed to contact only the bottom of the well, without contacting the side walls of each well. After 30 minutes incubation, the wells were washed twice with 200 uL PBS/azide then aspirated. Subsequently, a solution of 1.5 mM DBCO-PEG 5K (Creative PEGWorks, Catalog No. PLS-9979) in PBS/azide was added to the wells to fill them completely. The DBCO-PEG-5k surface blocking reagent, a copper-less Click reagent containing a polyethylene glycol surface blocking ligand with a molecular weight of 5000 Da, reacted with remaining azide functionalities that were present outside of (and surrounding) the streptavidin modified region at the bottom of the well.

Experiment 4. Preparation of activated T-cells using a lymphocyte-activating covalently functionalized well plate.

Preparation of well plate: A covalently functionalized well plate was prepared for activation of T cells, with the wells of the well plate having varying ratios of primary and co-activating ligands. A streptavidin-functionalized well plate was prepared similarly as described in Experiment 5, differing in that biotin-streptavidin functionalization was applied to the bottom of each well without restricting the region extensively (e.g., the area of functionalization extended to substantially all of the area of the bottom surface of the well).

Figures 3A, 3B:
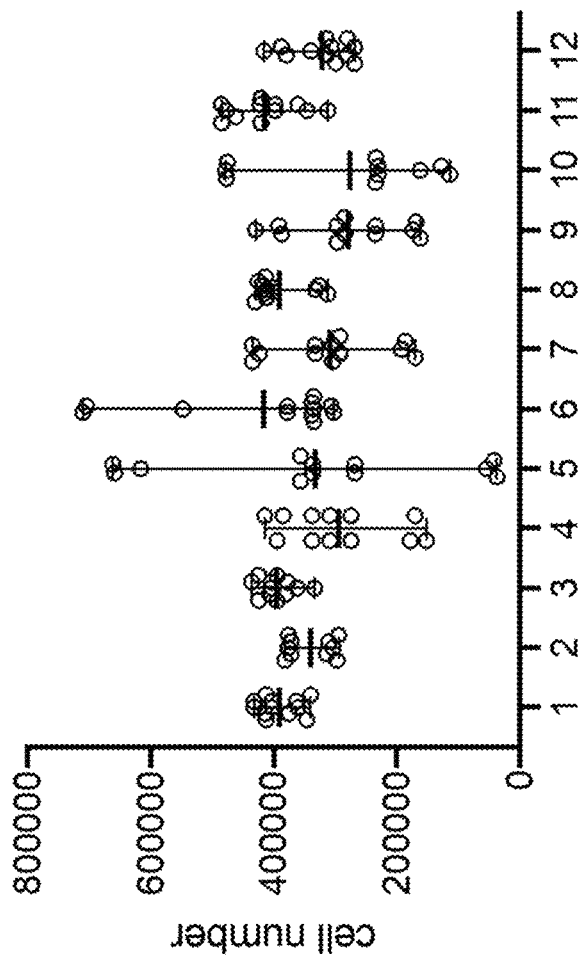
FIGS. 3A-3D are graphical representations of cell population characteristics of T cells activated according to some embodiments of the disclosure.

Activating ligand functionalization: stock solutions of biotin-conjugated anti-CD3 (primary stimulation), anti-CD28 and anti-CD2 (costimulation) antibodies were prepared at 100 ug/mL and mixed at various ratios in PBS (FIG. 3A). The final total antibody concentration was 50 ug/mL. 50 ul of each activation ligand solution was added to individual wells and allowed to bind for 30 minutes at room temperature. The microplate wells were next washed once with PBS, then held at 4° C. until used to stimulate T cells.

Figure 3D:
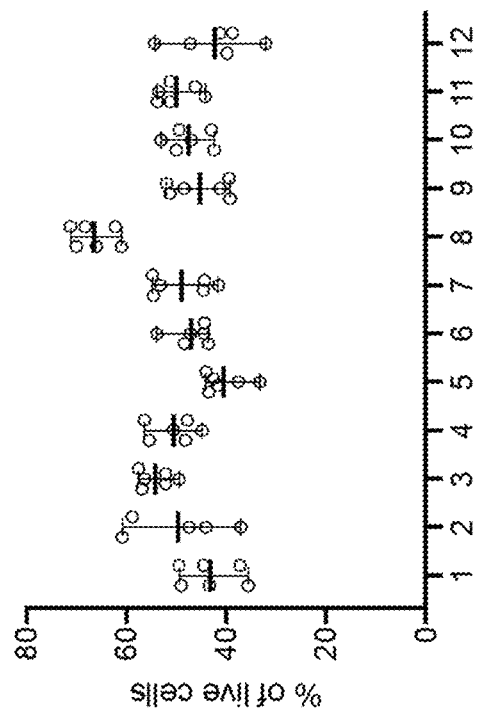
Figure 3C:
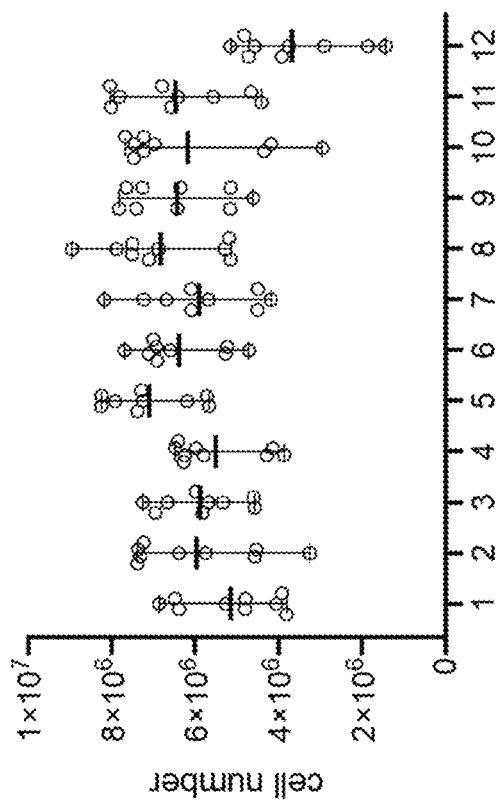

Preparation of T cells for stimulation: CD3+ T cells were enriched from PBMCs using a commercial Human T cell enrichment kit (EasySep™, StemCell Technologies, Catalog No. 19051). To each well of the activating plate, 200,000 CD3+ T cells were plated in 200 ul of T cell media (Advanced RPMI 1640 (Gibco™, Thermo Fisher, Catalog No. 12-633-012) supplemented with 10% Human AB Serum (Corning™, Fisher Catalog No. MT35060CI), 2 mM GlutaMAX™ (Thermo Fisher, Catalog No. 35050061), 50 uM 2-MercaptoEthanol (Thermo Fisher, Catalog No. 31350010), 25 ng/mL IL-7, and 10 ng/mL IL-15 (R&D Systems, Catalog No. 207-IL/CF; 247-ILB-005). A control condition (Condition 12) was included in which T cells were activated with a 1:1 ratio of anti-CD3 and anti-CD28-coated beads (Thermo Fisher, Catalog No. 11161D). Cells were cultured for 4 days, at which point 50 ul of cells from each well was transferred into a new, untreated round-bottom 96-well microplate (Corning, Catalog No. 3879) and 150 ul of fresh T cell media was added. At day 4, 50 ul samples from each well were also collected to determine the number of T cells in each well. At day 7, 100 ul of cells was removed from each well and replaced with 100 uL of T cell media. At day 10, 100 ul of media, leaving cells intact, was removed from each well and replaced with 100 ul of T cell media. At day 11, 200 ul samples were collected from each well to determine the number of T cells in each well, and the surface expression of CD28 and CD27 on the T cells was assessed. As shown in FIGS. 3B, 3C, and 3D (mean and range provided), the ratios of primary stimulating ligand (CD3) to costimulatory ligands can be altered to provide effective T cell expansion at day 4 (FIG. 3B) and day 11 (FIG. 3C), and co-expression of CD27 and CD28 (FIG. 3D). This experiment demonstrates that lymphocyte activation may be generally achieved, depending on the activating ligands attached to the wells of the functionalized well plate, and can achieve similar levels of activation and expansion compared to that observed using CD3/CD28 labeled beads (Condition 12 of FIG. 3A).

Experiment 5. Preparation of streptavidin-presenting covalently functionalized wells of a well plate. Treatment of azido-modified well plates (as prepared in Experiments 1 and 2) with DBCO-PEG$_4$-Biotin/DBCO-PEG$_5$-Acid, as shown in FIG. 1B, was performed. A 10% DBCO-PEG$_4$-Biotin (Broadpharm, Catalog #BP-22295) solution, a copper-less Click dibenzocyclooctynyl coupling moiety linked via a polyethylene glycol linker (four PEG units) covalently attached to biotin, for example, was prepared as a 0.2 mM biotin containing Click reagent solution which also included 1.8 mM DBCO-PEG$_5$-Acid (Broadpharm, Catalog #BP-24056), a copper-less Click dibenzocyclooctynyl coupling moiety linked via a polyethylene glycol linker (five PEG units) covalently attached to a carboxylic acid moiety, prepared in PBS/0.02% sodium azide. The PEG$_5$-Acid Click reagent functioned as a surface blocking ligand. Other ratios may be used to vary the density of biotin moieties introduced to the bottom of the well. This solution was added to wells in volumes ranging from 250 nL to 50 μL, which provided covalently linked biotin moieties in respectively greater regions of the bottom of the well. After 30 minutes of incubation, the wells were washed twice with 200 uL PBS/azide then aspirated. A 2 micromolar solution of streptavidin was prepared and added to the wells. The streptavidin was non-covalently attached to biotin, which was itself covalently attached to the surface of the well, as in FIG. 1A. Using varying volumes of Click reagent containing biotin, different size regions containing streptavidin were obtained. After 15 minutes incubation, a solution of 1.5 mM DBCO-PEG 5K (Broadpharm Catalog #BP-22461), in PBS/azide was added to the wells, filling the wells up and reacting with the remaining azido reactive moieties still present within each well (i.e., outside of the region modified by the combination of streptavidin and PEG$_5$-carboxylic acid moieties).

Experiment 6. Preparation of a region-restricted antigen-presenting T lymphocyte activating well plate. A standard Polystyrene tissue culture microplate (Corning) was plasma treated and functionalized to present azide using Chemical Vapor Deposition, as described in Experiments 1 and 2. A 1 uL drop of 2 micromolar DBCO-conjugated Streptavidin in PBS (SAV covalently attached to the surface, as in FIG. 1B) was placed in the center of the functionalized 96-well round-bottom microplate wells using an automated liquid handling robot (OpenTrons), providing an approximately 1 mm diameter region of streptavidin functionalization on the bottom of the well. No streptavidin was introduced to the walls of the well. The spotted drops were dried onto the microplate surface in a Biosafety Cabinet. To passivate remaining azide groups, wells were filled with a 1.5 mM solution of DBCO-PEG3000, thereby introducing PEG3000 surface blocking ligands in the remainder of the surface within the well (i.e., outside of the streptavidin modified region on the bottom of the well). This solution was applied to the wells for 15 minutes at room temperature. The wells were then rinsed once with PBS to remove unreacted DBCO-PEG3,000.

Figure 4A:
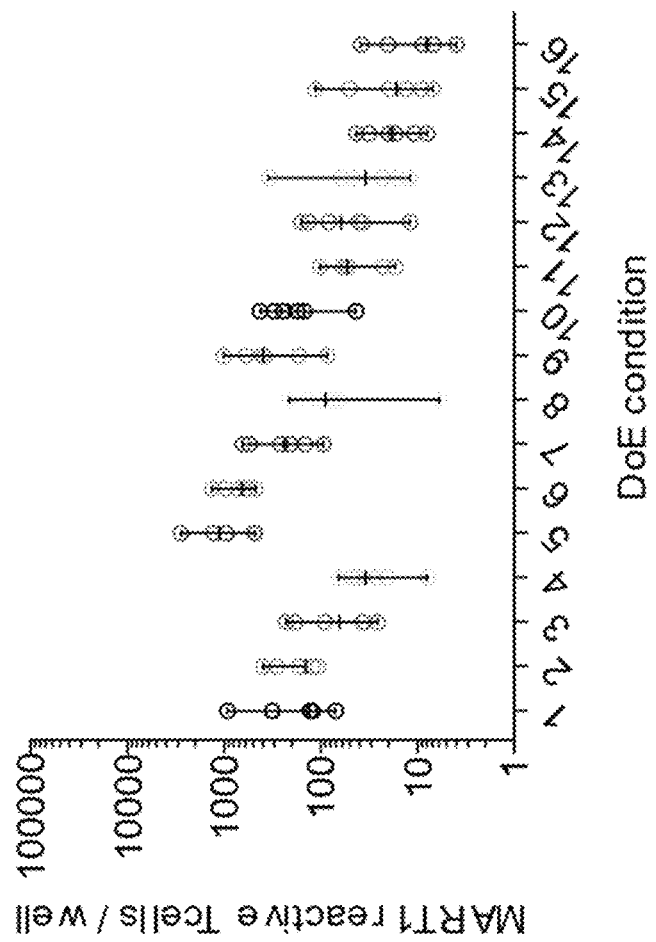
FIG. 4A is a table representing the experimental conditions used for a multivariate T cell activation experiment.

To bind T cell activating ligands to the surface, mixtures of Biotin-conjugated peptide-HLA (primary stimulation), anti-CD28 antibody and anti-CD2 antibody (costimulation) were mixed at various concentrations in Buffer (PBS with 2 mM EDTA and 0.5% Bovine Serum Albumin). For peptide-HLA, four three-fold serial dilutions were prepared when added to the microplate. For the anti-CD28 and anti-CD2 antibodies, four nine-fold serial dilutions were prepared. (See FIG. 4A) For this experiment, the ratio of anti-CD28: anti-CD2 was 1:1, but other ratios may successfully be used to stimulate T cells. The serial dilutions of peptide-HLA and antibody were further diluted into 16 tubes of Buffer such that final concentrations of peptide-HLA ranged from 7.5 ug/mL to 0.28 ug/mL, and final concentrations of costimulation antibodies varied from 15 ug/mL to 0.02 ug/mL (total antibody concentration), as shown in FIG. 4A. 40 uL of each activating ligand solution was added to 6 wells and allowed to bind for 30 minutes at room temperature. The microplate wells were then washed once with PBS, and then held at 4° C. until used to stimulate T cells.

Figure 4C:
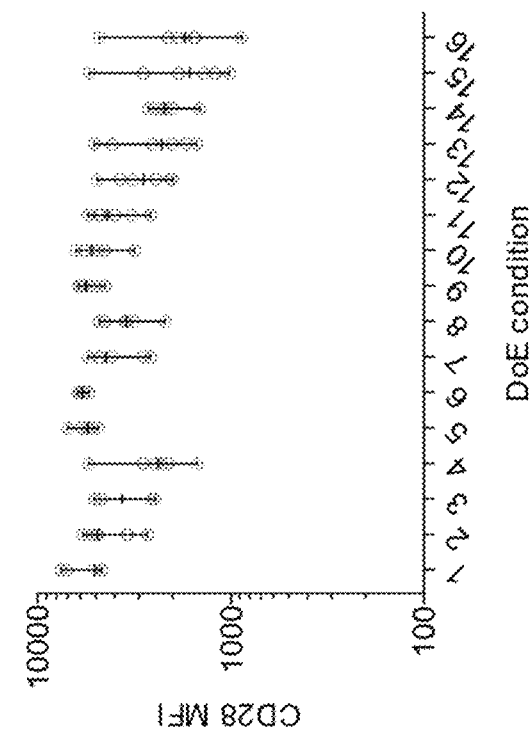
FIGS. 4B to 4C are schematic representations of the observed cell surface markers resulting from the multivariate T cell activation experiment designed as in FIG. 4A.
Figure 4B:
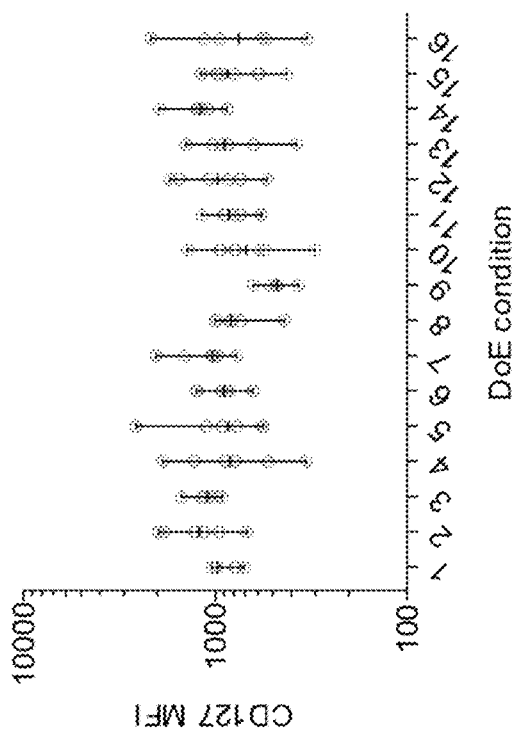

To activate T cells with the microplate, CD8$^+$ T cells were enriched from PBMCs using a commercial CD8+ T cell isolation kit (StemCell Technologies). To each well of the activating plate, 200,000 cells enriched for CD8$^+$ T cells were plated in 200 uL of T cell media (Advanced RPMI (Thermo Fisher) supplemented with 10% Human AB Serum (Corning), 2 mM GlutaMAX (ThermoFisher), 50 uM 2-MercaptoEthanol (Thermo Fisher)) with 30 ng/mL IL-21 (R&D Systems). Cells were cultured in an incubator for 48 hours, then 50 uL of T cell media with 150 ng/mL of IL-21 was added to each well, and culturing continued. After 5 days, 50 uL of media was removed from each well, and the cells were transferred to a new activating well plate prepared as described above. 50 uL of T cell media with 150 ng/mL IL-21 was added to each well and culturing continued. The next day, 50 uL of media was removed from each well and 50 uL of T cell media with 10 ng/mL IL-7 and 50 IU/mL IL-2 was added to each well. The next day, 50 uL of media was again removed from each well and 50 uL of T cell media with 150 ng/mL of IL-21 was added to each well. Culturing was continued for 5 days, at which point, samples were collected from each well to determine the number of antigen-specific T cells in each well, and the surface expression of CD28 and CD127 on the antigen-specific T cells was assessed. As shown in FIGS. 4A, 4B, and 4C, the ratios of primary stimulating ligand (MHC) to costimulatory ligands can be altered to provide effective antigen-specific activation (FIG. 4A), CD127 expression (FIG. 4B) and CD28 expression (FIG. 4C).

Experiment 7. Antigen Specific Activation of T lymphocytes within wells having an antigen-presenting covalently functionalized surface upon the bottom surface of the well. 96-well, round-bottom, tissue culture-treated microplates (Corning) were functionalized as in Experiments 1 and 2 to introduce an azido-presenting covalently functionalized surface upon the bottom surface of each well. A biotin-presenting covalently functionalized surface was introduced into the bottom of each well by addition of 0.05 mL of 0.5 mM Copper Sulfate, 0.1 mM Sodium Ascorbate and 5 mM Alkyne-PEG4-Biotin to the bottoms of the wells, which functionalized the entire bottom surface of each well.

To passivate the remaining azide and restrict the Biotin-functionalized region of the wells to the initially spotted restricted region of deposited functionalization mixture, 0.2 mL of passivation solution (5 mM DBCO-PEG4-Carboxylic Acid in PBS) was added to each well. This passivation reaction proceeded for 30 minutes at room temperature. The passivation solution was removed, and the wells washed once with 0.2 mL of PBS before proceeding. A streptavidin-presenting covalently functionalized region was then introduced by adding 0.05 mL of 0.25 mg/mL Streptavidin in PBS to each well having a biotin-presenting covalently functionalized region. After 30 minutes at room temperature, the streptavidin solution was removed by aspiration, and wells were rinsed twice with 0.2 mL of PBS.

Introduction of the antigen-presenting covalently functionalized activating region upon the bottom surface of the well: 0.05 mL of a 0.83 microgram/mL MART1 pHLA (antigen peptide loaded site-specific biotinylated monomeric MHC molecule having a C-terminal BirA tag for site specific biotinylation, where the MHC molecule included a MART1 antigenic peptide preloaded into the MHC) solution in PBS-BSA was added to each well having a streptavidin-presenting covalently functionalized region. After 30 minutes, the pHLA mixture was removed by aspiration, and 0.05 mL of a costimulation functionalization mixture was added to each well. The costimulation functionalization mixture consisted of Biotinylated anti-CD28 at 2.5 micrograms/mL and Biotinylated anti-CD2 at 2.5 micrograms/mL. After 30 minutes at room temperature, the costimulation functionalization mixture was removed by aspiration, and the wells having an antigen-presenting covalently functionalized region were rinsed twice with 0.2 mL of PBS-BSA. This provided a T cell activating region at the bottom of each treated well, where antigen-presenting ligands and co-stimulatory ligands (anti-CD28, anti-CD2) were presented for T cell activation.

Expansion of antigen-specific T Cells within the well containing a surface having an antigen—presenting region for activation was then compared to expansion with synthetic Antigen Presenting Beads (prepared as described in PCT/US2018/043146, filed on Jul. 20, 2018, the entire disclosure herein incorporated by reference in its entirety). CD8+ T cells were isolated from Peripheral Blood Mononuclear Cells using an EasySep™ Human CD8+ T Cell Isolation Kit (StemCell Technologies) according to the manufacturer's recommended procedure. The enriched CD8+ T cells were resuspended at 1e6/mL in growth media with IL-21 at 30 nanograms/mL (R&D Systems). The growth media consisted Advanced RPMI 1640 Medium (Thermo Fisher) supplemented with 10% Human AB Serum (Corning CeliGro) plus GlutaMax (Thermo Fisher) and 50 micromolar Beta-MercaptoEthanol (Thermo Fisher).

The CD8+ T cells were then split into two samples for stimulation within the wells having a an antigen-presenting region or synthetic antigen-presenting beads. For bead stimulation, MART1-specific synthetic antigen-presenting beads were added to the cells at a 1:1 ratio. To each well of a standard 96-well round-bottom tissue culture microplate, 200,000 cells were plated. For antigen-presenting covalently functionalized region stimulation, 200,000 cells were plated per well of a MART1-specific antigen-presenting covalently functionalized wells of a microplate prepared as described above. The plates were then incubated in a standard 5% $CO_2$, 37° C. incubator for two days. After two days in culture, IL-21 was diluted to 150 nanograms/mL in growth media. 50 microliters of IL-21 diluted in media was added to each well, and the plate was returned to the incubator additional culture.

After a total of seven days of culture, the cells were re-stimulated with MART1-specific synthetic antigen-presenting activating beads or antigen-presenting covalently functionalized regions of a well. For bead-based re-stimulation, from each well of the plate, 0.05 of media were removed. IL-21 was diluted to 150 ng/mL in fresh media, and synthetic antigen-presenting activating beads were added to the IL-21/media mixture at a final density of 4e6 beads/mL. 50 microliters of this IL-21/beads/media mixture were added to each well, resulting in an additional 2e5 beads being added to each well.

For re-stimulation in wells having a surface containing an antigen-presenting covalently functionalized region, 50 microliters of media were removed from each well of the plate. The cells in the wells were resuspended by repetitive pipetting and the remaining volume was transferred to a fresh well plate having wells including antigen-presenting covalently functionalized region therewithin, prepared as described above. IL-21 was diluted to 150 ng/mL in fresh growth media, and 50 microliters of this IL-21/growth media mixture were added to each well of the fresh well plate having a surface containing an antigen-presenting covalently functionalized region.

The next day, both sets of well plates were removed from the incubator, and 50 microliters of media again removed from each well. IL-2 (R&D Systems) was diluted into fresh media to 50 Units/mL. To this media containing IL-2, IL-7 (R&D Systems) was added at a final concentration of 12.5 ng/mL. 50 microliters of this IL-2/IL-7/media mixture was added to each well, and both sets of well plates were returned to the incubator.

The next day, both sets of well plates were removed from the incubator, and 50 microliters of media again removed from each well. IL-21 was diluted into fresh media to 150 nanograms/mL. 50 microliters of this IL-21/media mixture was added to each well, and the well returned to the incubator.

After culturing the cells for an additional 5 days, the cells were analyzed for antigen-specific T Cell expansion and expression of memory precursor surface markers (CD28 and CD127).

Figure 5A:
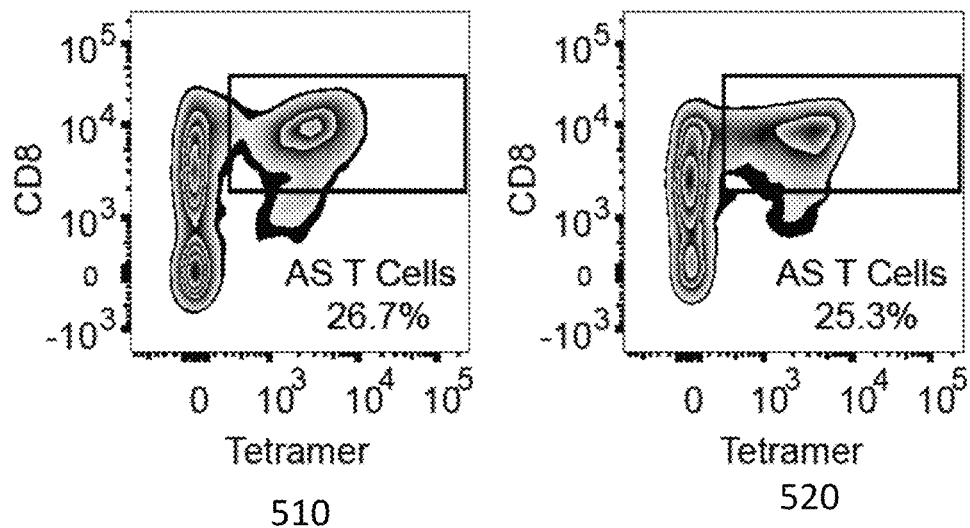
FIGS. 5A-5D are graphical representations of cell population characteristic of T cells activated according to some embodiments of the disclosure.
Figure 5B:
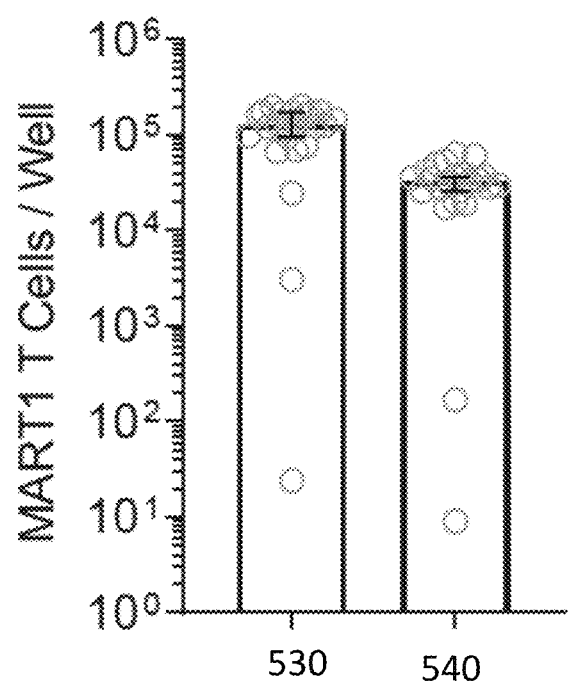
Figure 5C:
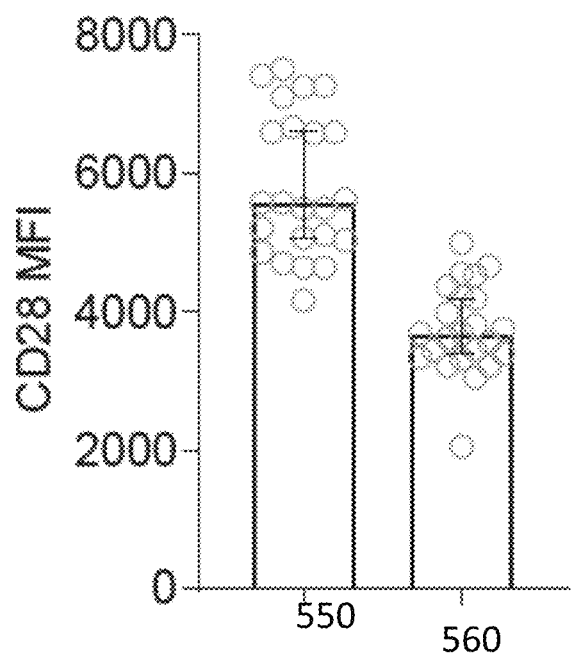
Figure 5D:
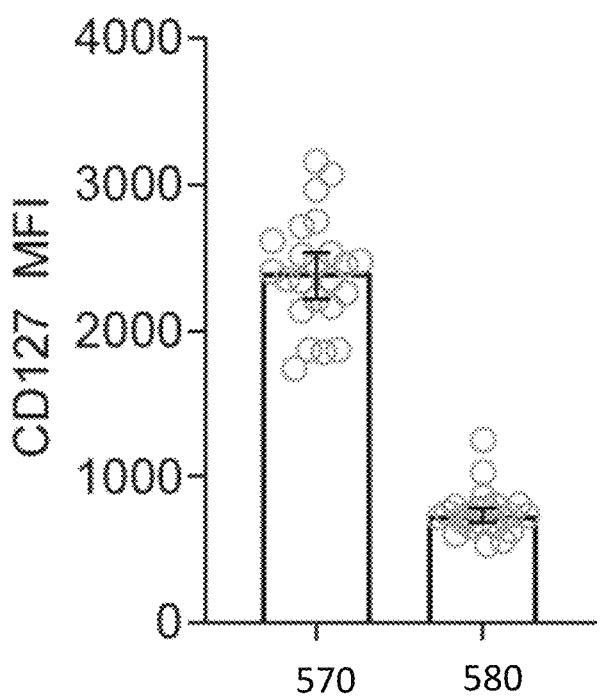

Results: Like wells loaded with synthetic antigen-presenting beads, the wells having a surface including an antigen-presenting covalently functionalized activating region were generally able to expand MART1-specific T Cells (FIG. 5A), as shown by the FACs results for bead-based activating 510 compared to that of antigen-presenting region activation 520. Nearly all wells including the antigen-presenting covalently functionalized region yielded high numbers of antigen-specific T Cells, with total numbers of antigen-specific T Cells being about two-fold lower for the cells 540 produced by the antigen-presenting region compared to the cell product 530 provided from synthetic antigen-presenting beads (FIG. 5B). However, when the expression of the memory precursor phenotype markers CD28 and CD127 was examined, a decrease in the expression of these markers (560 of FIG. 5C (CD28 expression) and 580 of FIG. 5D (expression of CD127) respectively) on the antigen-specific T Cells generated using the wells having an antigen-presenting activating region was observed in comparison to the levels of expression seen for antigen-specific T cells produced by use of synthetic antigen-presenting beads (550 of FIG. 5C (CD28 expression), and 570 of FIG. 5D (CD127 expression), respectively). This suggested that while the wells having an antigen-presenting activating region could support expansion of antigen-specific T Cells, the cells were more differentiated than the cells expanded using the synthetic antigen-presenting beads. These results further suggested that limiting the area of stimulation in wells having synthetic antigen-presenting activating region may be advantageous for some cell activations, such as antigen-specific T cell stimulation.

Experiment 8. Covalently functionalized region size control. To prepare well plates having wells with lymphocyte activating regions (in this case antigen-presenting covalently functionalized regions for activating T cells antigen specifically of varying area on the bottom surface of standard tissue culture microplates, standard 96-well round-bottom tissue culture microplates (Corning) were first functionalized with 7-Azidoheptyiltrimethylsilane as described in Experiments 1 and 2. A microplate functionalization mixture consisting of 0.5 mM Copper Sulfate, 0.1 mM Sodium Ascorbate and 5 mM Alkyne-PEG4-Biotin was then prepared in water. Using an automated liquid handling robot (OpenTrons), 0.25, 0.5, 1, 2, 4, and 8 microliter drops of functionalization mixture were delivered to the center of the wells of the coated microplate. The microplate was held at room temperature for 45 minutes to allow reaction of the Alkyne Biotin with the microplate. To passivate the remaining azide and restrict the Biotin-functionalized region of the wells to the initially spotted restricted region of deposited functionalization mixture, 0.2 mL of passivation solution (5 mM DBCO-PEG4-Carboxylic Acid in PBS) was added to each well. This passivation reaction proceeded for 30 minutes at room temperature. The passivation solution was removed, and the wells washed once with 0.2 mL of PBS before proceeding.

To measure each area of the biotin-presenting covalently functionalized regions that were formed at the bottom of the wells, the wells were then stained with 0.05 mL of 0.01 mg/mL Streptavidin conjugated to Alexa Fluor 488 (ThermoFisher Cat. No. S11223) in PBS for 30 minutes at room temperature. The Streptavidin staining solution was washed away, and the spots were imaged with an inverted fluorescence microscope (EVOS, ThermoFisher) that had been calibrated with a calibration slide. The areas of the resulting circular spots were then measured by creating lines in ImageJ across the images of the patches along several directions and averaging the lengths. The areas of the spots were then calculated using the formula relating the radius of a circle to its area.

Figure 6B:
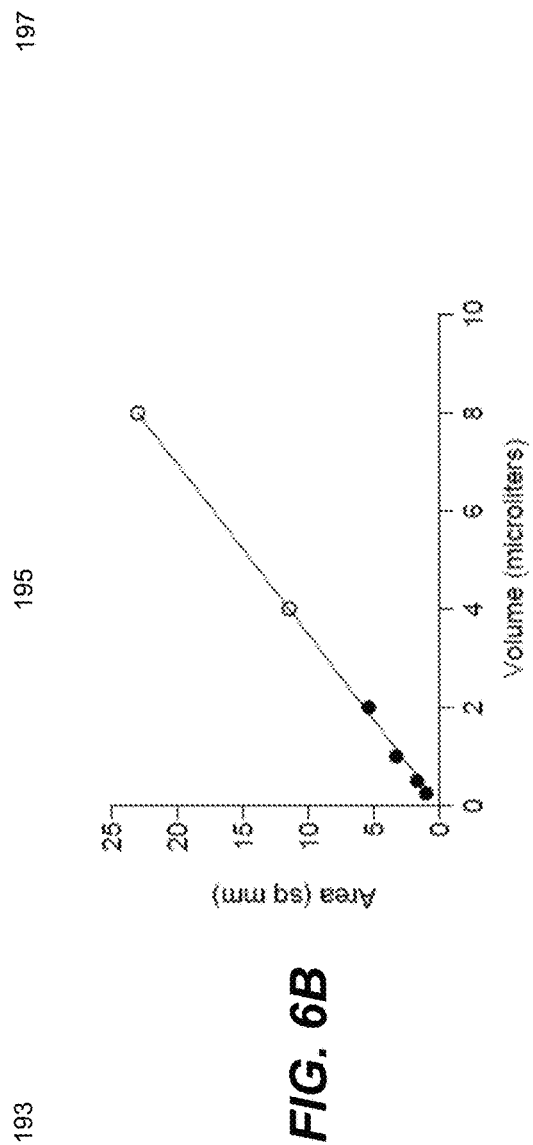
FIG. 6B is a graphical representation of measured and calculated areas of streptavidin-presenting covalently functionalized regions introduced according to some embodiments of the disclosure.

Results. Increasing the volume of the functionalization mixture resulted in a general increase in the size of the resultant functionalized region (FIG. 6A). To quantify the relationship between functionalization drop volume and functionalized area, the fluorescent spot areas for drops of 0.25, 0.5, 1 or 2 microliters were measured. A linear fit of the spot area vs drop volume was then calculated (FIG. 6B). This fit was then used to estimate the areas for functionalized regions prepared using 4 microliter and 8 microliter drops. These directly measured areas and indirectly measured areas for each covalently functionalized region were used in the following experiments.

Experiment 9. Preparation of streptavidin functionalized well plates having a restricted region for activation, limited to the central region of the bottom surface of wells. A standard, 96-well round-bottom tissue culture microplate (Corning) was first coated with 7-Azidoheptyiltrimethylsilane by CVD as described above in Experiment 1 and 2. A microplate functionalization mixture consisting of 0.5 mM Copper Sulfate, 0.1 mM Sodium Ascorbate and 5 mM Alkyne-PEG4-Biotin (Click Chemistry Tools, Catalog #TAT105-100) was then prepared in water. Using an automated liquid handling robot (OpenTrons), a 1.00 microliter drop of the microplate functionalization mixture was delivered to the center of the wells of the coated microplate. This resulted in an approximately 2 mm diameter spot at the bottom of each well, based on the results of Experiment 8, FIG. 6B. The microplate was held at room temperature for 45 minutes to allow reaction of the alkyne functionality of the Alkyne-PEG4-Biotin reagent with the microplate. To passivate the remaining azide and restrict the Biotin-functionalized region of the wells to the initial ~2 mm diameter spot, 0.2 mL of passivation solution (5 mM DBCO-PEG4-Carboxylic Acid (Sigma Aldrich, Catalog #759902-5 mg) in PBS) was added to each well. This passivation reaction proceeded for 30 minutes at room temperature. The passivation solution was removed, and the wells washed twice with 0.2 mL of PBS before proceeding.

To prepare the wells for binding of Biotin-conjugated peptide-HLA (pHLA, primary stimulation) and costimulation antibodies, 0.05 mL of 0.25 mg/mL Streptavidin was added to each well and incubated for 30 minutes at room temperature. Excess Streptavidin was removed by washing each well twice with 0.2 mL of PBS.

Experiment 10. Functionalization of region—restricted streptavidin-presenting well plate with T-cell activating species. To load pHLA (antigen peptide loaded site-specific biotinylated monomeric MHC molecule having a C-terminal BirA tag for site specific biotinylation, having a MART1 antigenic peptide preloaded into the MHC) onto the streptavidin-presenting functionalized spots in each well, 0.05 mL of a 0.83 microgram/mL solution of biotinylated pHLA in PBS with 0.1% BSA was added to each streptavidin functionalized well. After 30 minutes at room temperature, the pHLA solution was removed, and a 5 microgram/mL (total antibody) solution of biotinylated anti-CD28 antibody (Biolegend, Catalog #302904 at 2.5 micrograms/mL) and biotinylated anti-CD2 antibody (Biolegend, Catalog #23002040 at 2.5 micrograms/mL) in PBS with 0.1% BSA was added to each well. After 30 minutes, the functionalization reagents were removed by washing each well twice with 0.2 mL PBS-BSA. Each treated well included an antigen-presenting covalently functionalized activating region, constrained to the initially spotted area. Functionalized microplates were prepared on the same day that T Cells were stimulated and were stored at 4° C. until cells were plated.

Experiment 11. T Cell Antigen-specific Stimulation and Expansion in wells of functionalized well plates having a restricted activating region compared to stimulation and expansion in the presence of synthetic antigen-presenting activating beads within a standard well plate. CD8+ T cells were isolated from Peripheral Blood Mononuclear Cells using an EasySep™ Human CD8+ T Cell Isolation Kit (StemCell Technologies) according to the manufacturer's recommended procedure. The enriched CD8+ T cells were resuspended at 1e6/mL in growth media with IL-21 at 30 nanograms/mL (R&D Systems). The growth media consisted Advanced RPMI 1640 Medium (Thermo Fisher) supplemented with 10% Human AB Serum (Corning Cell-Gro) plus GlutaMax (Thermo Fisher) and 50 micromolar Beta-MercaptoEthanol (Thermo Fisher).

The CD8+ T cells were then split into two samples for stimulation with antigen-presenting activating beads within a standard well plate or within the region-restricted antigen-presenting activating well plate of Experiment 10. For antigen-presenting activating bead stimulation, MART1-antigen-presenting activating beads (prepared as described in PCT/US2018/043146, filed on Jul. 20, 2018, the entire disclosure herein incorporated by reference in its entirety) were added to the cells at a 1:1 ratio. To each well of a standard 96-well round-bottom tissue culture microplate, 200,000 cells were plated. For region-restricted antigen-presenting activating well plate stimulation, 200,000 cells were plated per well of an region-restricted antigen-presenting activating well plate prepared as described in Experiment 10. The plates were then incubated in a standard 5% $CO_2$, 37° C. incubator for two days. After two days in culture, IL-21 was diluted to 150 nanograms/mL in growth media. Fifty microliters of IL-21 diluted in media was added to each well, and the plate was returned to the incubator for additional culture.

After a total of seven days of culture, the cells were re-stimulated. For antigen-presenting activating bead re-stimulation, 50 microliters of media were removed from each well of the plate. IL-21 was diluted to 150 ng/mL in fresh media, and antigen-presenting activating beads are added to the IL-21/media mixture at a final density of 4e6 beads/mL. 50 microliters of this IL-21/bead/media mixture were added to each well, resulting in an additional 2e5 antigen-presenting activating beads being added to each well.

For region-restricted antigen-presenting activating well plate re-stimulation, 50 microliters of media were removed from each well of the plate. The cells in the wells were resuspended by repetitive pipetting and the remaining volume (~0.2 mL per well) was transferred to a freshly prepared region-restricted antigen-presenting activating well plate, which was prepared as described in Experiment 9. IL-21 was diluted to 150 ng/mL in fresh growth media, and 50 microliters of this IL-21/growth media mixture were added to each well of the freshly prepared region-restricted antigen-presenting activating well plate.

The next day, the plates were removed from the incubator, and 50 microliters of media again removed from each well. IL-2 (R&D Systems) was diluted into fresh media to 50 Units/mL. To this media containing IL-2, IL-7 (R&D Systems) was added at a final concentration of 12.5 ng/mL. 50 microliters of this IL-2/IL-7/media mixture was added to each well of both sets of well plates, and the well plates were returned to the incubator.

The next day, the plates were removed from the incubator, and 50 microliters of media again removed from each well. IL-21 was diluted into fresh media to 150 nanograms/mL. 50 microliters of this IL-21/media mixture was added to each well of both well plates, and the well plates were returned to the incubator.

After culturing the cells for an additional 5 days, the cells from each set of region-restricted antigen-presenting activating well plates and antigen-presenting activating bead well plates were analyzed for antigen-specific T cell expansion and expression of memory precursor surface markers (CD28 and CD127).

Characterization. After the two rounds of stimulation, a 50 microliter sample was collected from each well of the antigen-presenting activating bead and region-restricted antigen-presenting activating well plates. Cells were washed once with wash buffer (PBS+2% Fetal Bovine Serum+5 mM EDTA). Cells were then stained with a mixture of antibodies against CD4 (Brilliant Violet™ 510, BioLegend Cat. No. 300545), CD8 (PerCP-Cy5.5, BioLegend Cat No. 344709), CD28 (FITC, BioLeend Cat. No. 302906), CD45RO (APC, BioLegend Cat. No. 304210), CD127 (BV420, BioLegend Cat. No. 351309), as well as a tetramer reagent (pMHC tetramer, PE) which marks antigen-specific T cells. Cells were stained for 30 minutes at room temperature in the dark and then washed once with wash buffer. Cells were resuspended in 0.15 mL of wash buffer with 0.01 mL of Count-Bright™ Beads (ThermoFisher Catalog #C36950) per well.

Cell populations were then analyzed on a FACSCelesta flow cytometer (Becton Dickinson and Co.) with High Throughput Sample (BD Biosciences). Total cell counts in the sample were calculated from the number of cells and Count-Bright beads collected in the sample according to the manufacturers recommended protocol. Flow cytometry samples were analyzed in FlowJo (FlowJo) to determine the antigen specific T cell frequency and expression of memory precursor markers (CD27, CD28, CD62L and CD127).

Figure 7D:
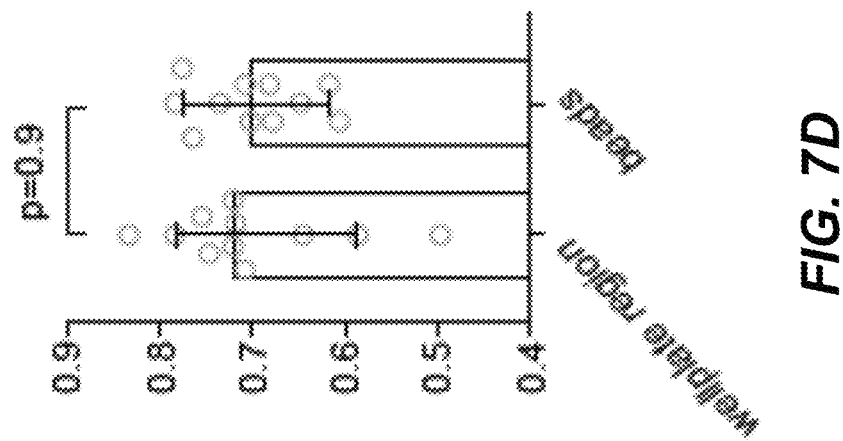
Figure 7C:
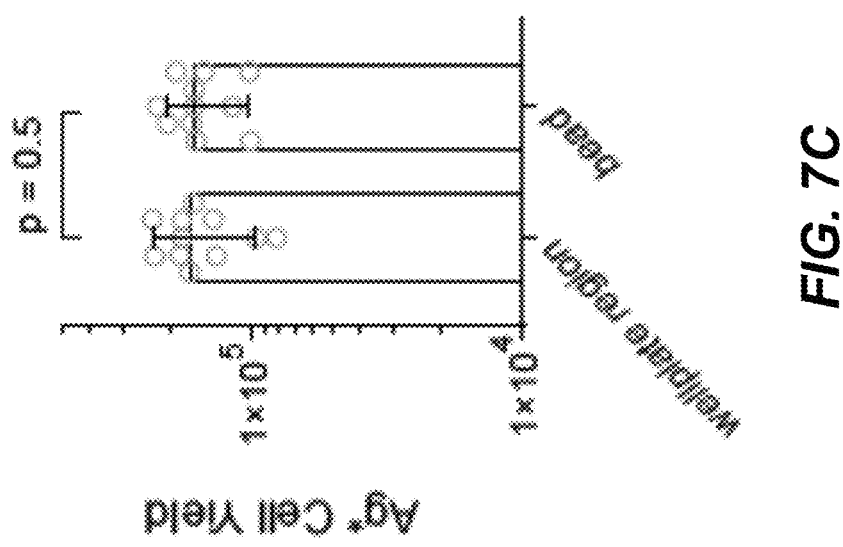

Flow cytometry samples were analyzed in FlowJo (FlowJo) flow cytometry analysis software program for antigen specific T cell frequency. This analysis indicated that the region-restricted antigen-presenting activating well plates consistently yielded high numbers of antigen specific T cells (FIG. 6B). Flow cytometric analysis indicated that region-restricted antigen-presenting activating well plates yielded equivalent numbers of antigen specific T cells relative to activation using antigen-presenting activating beads (FIG. 7A). FIG. 7C shows graphic comparison of numbers of antigen positive T cells produced per well in the region-restricted activating well compared to the numbers of antigen positive T cells produced per well using antigen-presenting activating beads. In addition, when the antigen specific T cells were analyzed for expression of CD127 and high levels of CD28, we observed that the region-restricted antigen-presenting activating well plate yielded equal or higher fractions of antigen specific T cells that expressed these markers of memory precursor T cells (FIG. 7D). Therefore, stimulation in the region-restricted antigen-presenting activating well plate is highly productive and yields activated T cells having a good central memory phenotype (e.g., indicative of Memory Precursor T Cells), and is equivalent to activation using synthetic antigen presenting activating beads.

Figure 8A:
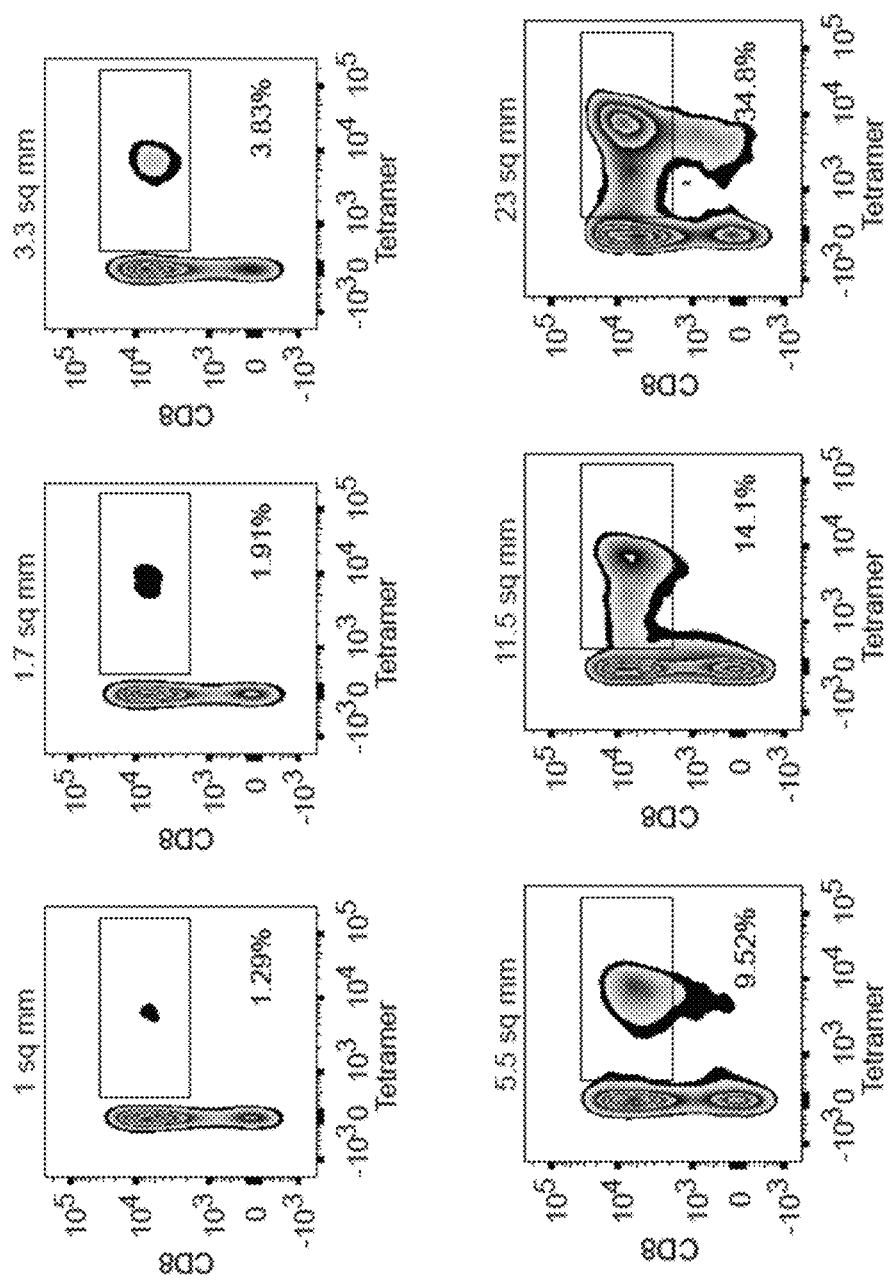
FIGS. 8A-8D are graphical representations of cell population characteristic of T cells activated according to some embodiments of the disclosure.

Experiment 12. Comparison of antigen-presenting functionalized region area to cell product yield and phenotype. Well plates having wells containing an antigen-presenting covalently functionalized region for activation of T cells were produced with areas ranging from about 1 sq mm to about 23 sq mm As shown in FIG. 8A, six different sized regions were produced: 1 $mm^2$; 1.7 $mm^2$; 3.3 $mm^2$; 5.5 $mm^2$; 11.5 $mm^2$; and 23 $mm^2$ (labels above each graphical figure of FIG. 8A identify the size of the region). The size of the covalently functionalized regions were controlled by depositing different volumes of 0.5 mM Copper Sulfate, 0.1 mM Sodium Ascorbate and 5 mM Alkyne-PEG4-Biotin, in a similar fashion to the process described in Experiment 8, to wells of a round-bottom 96-well microplate having an azido-presenting covalently functionalized surface prepared as in Experiments 1 and 2. After passivation of remaining azido moieties as described above (Experiments 8 and 9), Streptavidin was bound to the biotin-presenting covalently functionalized regions as described above in Experiments 8 and 9. Primary activating molecule pHLA (antigen peptide loaded site-specific biotinylated monomeric MHC molecule having a C-terminal BirA tag for site specific biotinylation, having a MART1 antigenic peptide preloaded into the MHC) and coactivating molecules (costimulation antibodies biotinylated anti-CD28 and biotinylated anti-CD2) were bound to the resultant streptavidin-presenting covalently functionalized regions on the bottom surface of each of the wells, to generate antigen-presenting covalently functionalized regions on the bottom surface of each of the wells, as described in Experiment 10.

T Cell Activation and Expansion within wells having antigen-presenting covalently functionalized activating regions of varying size. Antigen-specific T Cells were activated and expanded as described above in Experiment 11. When a second, fresh antigen-presenting covalently functionalized region of a surface of a well plate was required in a second round of stimulation, the same size of activating region was matched for each well of the well plate. After completion of both rounds of stimulation, a 0.05 mL sample of cells was collected from each well, and the frequency of antigen-specific T Cells was determined, as well as the expression of CD28 and CD127 in the antigen-specific T Cells.

Figure 8B:
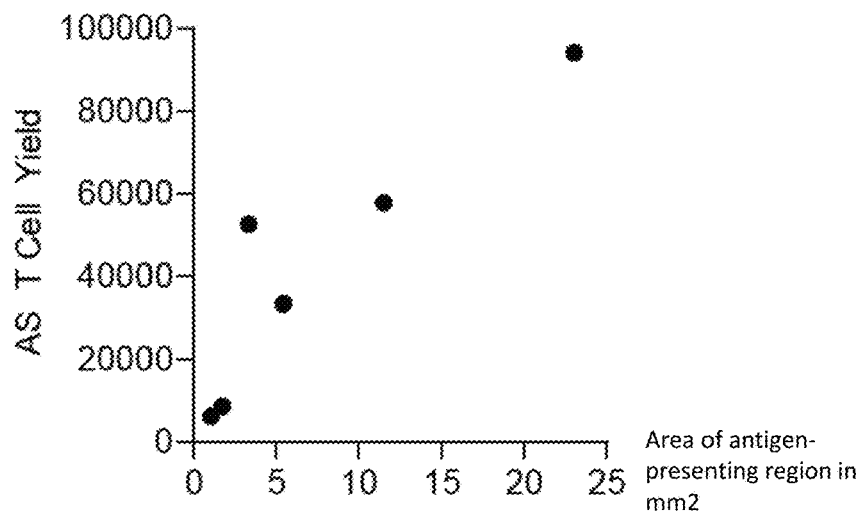
Figure 8C:
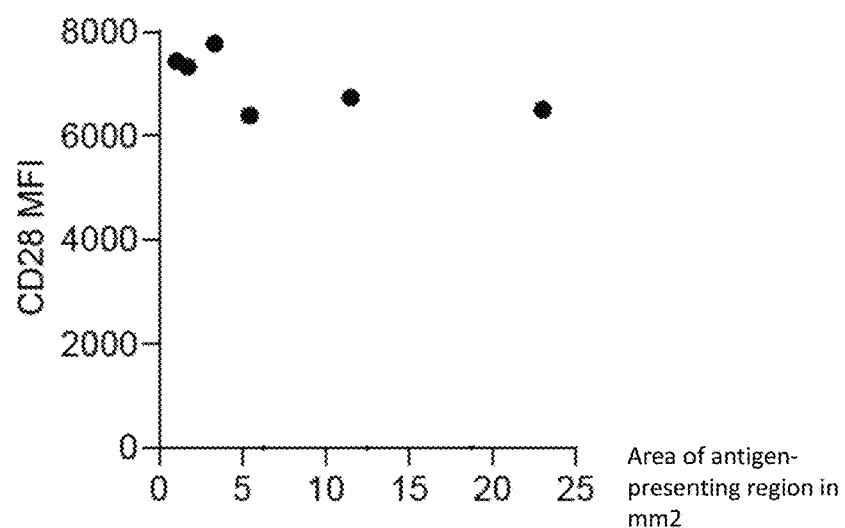
Figure 8D:
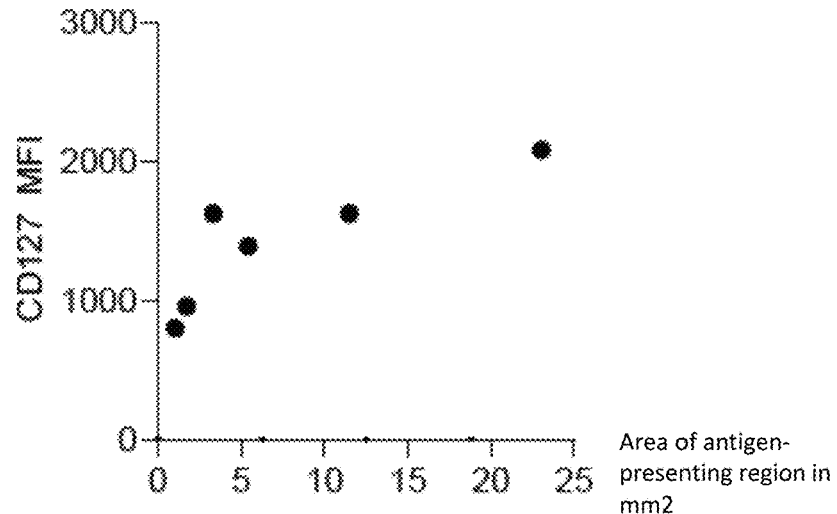

Results. Stimulation and expansion was seen for the antigen-presenting activating regions of the wells having an area of about or just over 1 mm$^2$, as shown in FIGS. 8A-8D. However, the yield of antigen-specific T Cells generally increased as the area of the antigen-presenting region increased from about 1 mm$^2$ (1.29% of the cell product were antigen-specific) to 23 mm$^2$ (34.8% of cell product was antigen specific and CD8 high). Note that the population below the flow cytometry gate cutoff are antigen specific, but have downregulated CD8 relative to the gate threshold chosen, with the amount of Antigen specific T Cells produced being generally linear relative to the area of activation (antigen-presenting region) as shown in FIG. 8B. Expression of CD28 in the antigen-specific T Cells was consistently high independent of the area of the antigen-presenting region (FIG. 8C). However, as the area of the antigen-presenting region increased, the expression of CD127 by the antigen-specific T Cells increased, indicating that antigen-presenting regions having larger areas better supported expansion of CD127+ T Cells (FIG. 8D), at least up to a point. In FIG. 8D, the increased expression of CD127 by the antigen-specific T Cells tends to plateau when the area of the antigen-presenting activating region exceeds about 25 mm$^2$ to about 30 mm$^2$. This indicates that antigen-presenting covalently functionalized region having areas of about 1 mm$^2$ to about 50 mm$^2$, or about 3 mm$^2$ to about 30 mm$^2$ provide optimized expansion of antigen-specific T Cells retaining high levels of expression of the memory precursor marker CD127. This result is in stark contrast to the phenotype of T cells produced without restriction of the area of antigen-presenting activation/stimulation, as described in Experiment 7 and shown in FIGS. 5A-5D. Accordingly, an antigen-presenting activating region having an area of less than 100 mm$^2$, less than 75 mm$^2$, or less than 50 mm$^2$ can be advantageous in terms of generating T Cells retaining high levels of expression of CD127.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

LIST OF SOME EMBODIMENTS OF THE DISCLOSURE

1. A well plate including a surface having a first region which is a reactive moiety-presenting covalently functionalized region or an activating moiety-presenting covalently functionalized region, where the reactive moiety is an azido moiety, a biotin moiety or a streptavidin moiety and the activating moiety is a lymphocyte-activating moiety.

2. The well plate of embodiment 1, where the first region has an area of at least 0.5 mm$^2$. In certain specific embodiments, the first region has an area of at least 0.6 mm$^2$, at least 0.7 mm$^2$, at least 0.8 mm$^2$, at least 0.9 mm$^2$, at least 1.0 mm$^2$, at least 1.1 mm$^2$, at least 1.2 mm$^2$, at least 1.3 mm$^2$, at least 1.4 mm$^2$, at least 1.5 mm$^2$, at least 1.6 mm$^2$, at least 1.7 mm$^2$, at least 1.8 mm$^2$, at least 1.9 mm$^2$, at least 2.0 mm$^2$, at least 2.5 mm$^2$, at least 3.0 mm$^2$, at least 35 mm$^2$, at least 4.0 mm$^2$, at least 4.5 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, or any range formed by two of the foregoing endpoints. In other specific embodiments, the first region has an area of about 0.5 mm$^2$ to about 50 mm$^2$, about 1.0 mm$^2$ to about 40 mm$^2$, about 2 mm$^2$ to about 35 mm$^2$, about 3 mm$^2$ to about 30 mm$^2$, or about 4 mm$^2$ to about 25 mm$^2$.

3. The well plate of embodiment 1 or 2, where the first region has a dimension of about 0.5 to about 4.0 mm (e.g., about 1.0 mm to about 35 mm, or about 1.5 mm to about 3.0 mm).

4. The well plate of any one of embodiments 1 to 3, where the first region is substantially circular and has a diameter of about 0.5 mm to 4.0 mm (e.g., about 1.0 mm to about 35 mm, or about 1.5 mm to about 3.0 mm).

5. The well plate of any one of embodiments 1 to 4, where the surface of the well plate further includes a second region which is a covalently modified region including surface blocking ligands, and optionally, where the second region surrounds the first region.

6. The well plate of any one of embodiments 1 to 5, where the surface of the well plate includes glass or polystyrene.

7. The well plate of any one of embodiments 1 to 5, where the surface of the well plate includes polypropylene, polycarbonate, polyethylene, cycloolefin copolymer, or melamine.

8. The well plate of any one of embodiments 1 to 7, where the first region ion has a density of respective reactive moieties or activating moieties of at least 50/um$^2$.

9. The well plate of any one of embodiments 1 to 8, where the first region includes respective reactive moieties or activating moieties linked covalently to the surface via a linker having from 5 to about 20 backbone atoms, about 10 to about 40 backbone atoms, or about 15 to about 50 backbone atoms selected from carbon, silicon, nitrogen and oxygen. Alternatively, the reactive moieties or activing moieties may be linked covalently to the surface through a series of about 5, 7, 9, 10, 11, 13, 15, 20, 25, 30, 35, 40, 45, 50, 55, 60, 65, 70, 75, 80, 90, 100, 200 bond lengths of a linker or any number of bond lengths therebetween.

10. The well plate of any one of embodiments 1 to 9, where the reactive moiety is streptavidin, and the streptavidin functionality is covalently attached to the first region of the surface of the well plate.

11. The well plate of any one of embodiments 1 to 9, where the reactive moiety is streptavidin, and the streptavidin functionality is non-covalently attached to a biotin moiety which is itself covalently attached to the first region of the surface of the well plate.

12. The well plate of any one of embodiments 1 to 11, where the first region is an activating moiety-presenting covalently functionalized region including a plurality of specifically bound primary activating molecular ligands and a plurality of specifically bound co-activating molecular ligands.

13. The well plate of embodiment 12, where a ratio of the primary activating molecular ligands to the co-activating molecular ligands on the first region of the surface is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

14. The well plate of embodiment 12 or 13, where each ligand of the plurality of specifically bound primary activating molecular ligands includes a major histocompatibility complex (MHC) molecule (e.g., Class I or Class II) configured to bind to a T cell receptor (TCR) of a T cell.

15. The well plate of embodiment 14, where the MHC molecule includes a MHC Class I protein sequence and a beta microglobulin protein sequence.

16. The well plate of embodiment 14 or 15, where each ligand of the plurality of specifically bound primary activating molecular ligands includes an MHC molecule further including an antigenic peptide.

17. The well plate of embodiment 16, where the antigenic peptide is a tumor-associated antigen, a viral antigen, a bacterial antigen, a fungal antigen, or a protozoan antigen.

18. The well plate of embodiment 17, where the antigenic peptide is a tumor-associated antigen, and optionally, where the tumor-associated antigen is SLC45A2, TCL1, VCX3A, MART1 or NYESO1.

19. The well plate of any one of embodiments 14 to 18, where the MHC molecule is connected to the activating moiety-presenting covalently functionalized region via a C-terminal linkage.

20. The well plate of any one of embodiments 12 to 19, where each ligand of the plurality of specifically bound co-activating molecular ligands includes a T cell receptor (TCR) co-activating molecule or an adjunct TCR activating molecule.

21. The well plate of embodiment 20, where a ratio of the TCR co-activating molecules to the adjunct TCR activating molecules of the plurality of co-activating molecular ligands is about 100:1 to about 1:100.

22. The well plate of embodiment 20 or 21, where a ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, where each of the foregoing values is modified by "about".

23. The well plate of any one of embodiments 20 to 22, where a ratio of the TCR co-activating molecules to the adjunct TCR activating molecules of the plurality of specifically bound co-activating molecular ligands is from about 20:1 to about 1:20 or about 3:1 to about 1:3.

24. The well plate of any one of embodiments 20 to 23, where the TCR co-activating molecules include a CD28 binding protein, or a fragment thereof which retains binding ability to CD28, and, optionally, where the CD28 binding protein or the fragment thereof further includes a site-specific C-terminal biotin moiety.

25. The well plate of any one of embodiment 20 to 24, where the TCR co-activating molecules include a CD80 molecule or a fragment thereof, where the fragment retains binding activity to CD28.

26. The well plate of any one of embodiments 20 to 25, where the TCR co-activating molecules includes an anti-CD28 antibody or a fragment thereof, where the fragment retains binding activity to CD28.

27. The well plate of any one of embodiments 20 to 26, where the adjunct TCR activating molecule includes a CD2 binding protein, or a fragment thereof which retains binding activity to CD2, and optionally, where the CD2 binding protein or the fragment thereof further includes a site-specific C-terminal biotin moiety.

28. The well plate of any one of embodiments 20 to 27, where the adjunct TCR activating molecule includes a CD58 molecule or fragment thereof, where the fragment retains binding activity with CD2.

29. The well plate of any one of embodiments 20 to 28, where the adjunct TCR activating molecule includes an anti-CD2 antibody or a fragment thereof, where the fragment retains binding activity with CD2.

30. The well plate of any one of embodiments 12 to 29, where the plurality of specifically bound primary activating molecular ligands and the plurality of specifically bound co-activating molecular ligands are specifically bound to streptavidin functionalities of a streptavidin-presenting first region of the well plate.

31. The well plate of any one of embodiments 12 to 30, where the plurality of specifically bound primary activating molecular ligands has a density of at least about $1\times10^2$ molecules per square micron in the first region, and optionally, a density of about $1\times10^2$ to about $1\times10^5$ molecules per square micron in the first region.

32. The well plate of any one of embodiments 12 to 31, where the plurality of specifically bound co-activating molecular ligands has a density of at least $1\times10^2$ molecules per square micron or about $1\times10^3$ to about $1\times10^5$ molecules per square micron in the first region.

33. A well plate, where each of one or more wells of the well plate includes the surface and the first region thereof of the well plate of any one of embodiments 1 to 32 (i.e., the surface can be an inner surface of a single well and the well plate can have one or more such surfaces).

34. The well plate of embodiment 33, where the first region of each of the one or more wells is located on a bottom surface of the corresponding well(s).

35. The well plate of embodiment 32, where an area of each first region is less than about 50%, less than about 25%, less than about 15%, less than about 10%, less than about 5%, or less than about 2% of the area of the bottom surface of the corresponding well(s).

36. The well plate of any one of embodiments 5 to 35, where each of the surface blocking ligands includes a hydrophilic or negatively charged moiety.

37. The well plate of embodiment 36, where the surface blocking ligands include polyethylene glycol (PEG) moieties.

38. A method of activating T lymphocytes (T cells) including contacting a plurality of T cells with an antigen-presenting covalently functionalized region of a surface of a well plate, where the antigen-presenting covalently functionalized region includes: a plurality of primary activating molecular ligands, each including a major histocompatibility complex (MHC) molecule (e.g., Class I or Class II) configured to bind to a T cell receptor (TCR) of a T cell, where each of the plurality of primary activating molecular ligands is linked to the surface; and a plurality of co-activating molecular ligands, each including a T cell receptor (TCR) co-activating molecule or an adjunct TCR activating molecule, where each of the co-activating molecular ligands is linked to the surface; and culturing the plurality of T cells in contact with the antigen-presenting covalently functionalized region of the surface, thereby converting at least a portion of the plurality of T cells to activated T cells.

39. The method of embodiment 38, where the T cells include CD8+ T cells.

40. The method of embodiment 38 or 39, where the antigen-presenting covalently functionalized region is a first region of a surface of a well plate according to any one of embodiments 12 to 33.

41. The method of any one of embodiments 38 to 40, where the plurality of co-activating molecular ligands includes TCR co-activating molecules and adjunct TCR activating molecules.

42. The method of any one of embodiments 38 to 41, where a ratio of the TCR co-activating molecules to the adjunct TCR activating molecules of the plurality of co-activating molecular ligands is about 100:1 to about 1:100.

43. The method of any one of embodiments 38 to 42, where a ratio of the TCR co activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, where each of the foregoing values is modified by "about".

44. The method of any one of embodiments 38 to 43, where the ratio of the TCR co-activating molecules to the adjunct TCR activating molecules of the plurality of co-activating molecular ligands is from about 20:1 to about 1:20 or about 3:1 to about 1:3.

45. The method of any one of embodiments 38 to 44, where each molecule of the plurality of MHC molecules includes an MHC Class I protein sequence, a beta macroglobulin protein sequence, and an antigenic peptide.

46. The method of embodiment 45, where the protein sequence of the MHC molecule is connected to the antigen-presenting covalently functionalized region of the surface via a C-terminal connection of the protein sequence.

47. The method of any one of embodiments 38 to 46, where the MHC molecule includes a biotin moiety and is attached to the antigen-presenting covalently functionalized region of the surface via a noncovalent interaction with streptavidin.

48. The method of embodiment 47, where the streptavidin is itself covalently bonded to the antigen-presenting covalently functionalized region of the surface.

49. The method of embodiment 48, where the streptavidin is bonded to the surface through a series of about 5, 7, 9, 10, 15, 20, 25, 30, 35, 40, 45, 50, 55, 60, 65, 70, 75, 80, 85, 95, 100, 200 bond lengths, or any number of bond lengths therebetween.

50. The method of embodiment 47, where the streptavidin is noncovalently associated with the antigen-presenting covalently functionalized region of the surface.

51. The method of embodiment 47 or 50, where the streptavidin is noncovalently associated with a biotin moiety, and the biotin moiety is covalently bonded to the antigen-presenting covalently functionalized region of the surface.

52. The method of embodiment 51, where the biotin is linked by a linker to the surface through a series of about 5 7, 9, 10 15, 20, 25, 30, 35, 40, 45, 50, 55, 60, 65, 70, 75, 80, 85, 95, 100, 200 bond lengths, or any number of bond lengths therebetween.

53. The method of any one of embodiments 39 to 52, where the antigenic peptide is a tumor-associated antigen, a viral antigen, a bacterial antigen, a fungal antigen, or a protozoan antigen.

54. The method of embodiment 53, where the antigenic peptide is a tumor-associated antigen, and optionally, where the tumor-associated antigen is SLC45A2, TCL1, VCX3A, MART1 or NYESO1.

55. The method of any one of embodiments 38 to 54, where each of the plurality of co-activating molecule ligands is linked to the antigen-presenting covalently functionalized region of the surface.

56. The method of any one of embodiments 38 to 55, where the T cell receptor (TCR) co-activating molecule includes a CD28 binding protein, or a fragment thereof which retains binding ability to CD28.

57. The method of embodiment 56, where the CD28 binding protein or the fragment thereof further includes a site-specific C-terminal biotin moiety.

58. The method of any one of embodiments 38 to 57, where the T cell receptor (TCR) co-activating molecule includes a CD80 molecule or a fragment thereof, where the fragment retains binding activity to CD28.

59. The method of any one of embodiments 38 to 58, where the T cell receptor (TCR) co-activating molecule includes an anti-CD28 antibody or a fragment thereof, where the fragment retain binding activity to CD28.

60. The method of any one of embodiments 38 to 59, where the adjunct TCR activating molecule includes a CD2 binding protein, or a fragment thereof which retains binding ability to CD2.

61. The method of embodiment 60, where the CD2 binding protein or the fragment thereof further includes a site-specific C-terminal biotin moiety.

62. The method of any one of embodiments 38 to 61, where the adjunct TCR activating molecule includes a CD58 molecule or fragment thereof, where the fragment retains binding activity with CD2.

63. The method of any one of embodiments 38 to 62, where the adjunct TCR activating molecule includes an anti-CD2 antibody or a fragment thereof, where the fragment retains binding activity with CD2.

64. The method of any one of embodiments 38 to 63, where the plurality of specifically bound primary activating molecular ligands has a density of at least about $1\times10^2$ molecules per square micron in the antigen-presenting covalently functionalized region of the surface, or, optionally, a density from about $1\times10^2$ to about $1\times10^5$ molecules per square micron in the antigen-presenting covalently functionalized region of the surface.

65. The method of any one of embodiments 38 to 64, where the plurality of specifically bound co-activating molecular ligands has a density of at least $1\times10^2$ to about $1\times10^5$ molecules per square micron in the antigen-presenting covalently functionalized region of the surface, or, optionally, about $1\times10^3$ to about $1\times10^5$ molecules per square micron in the antigen-presenting covalently functionalized region of the surface.

66. The method of any one of embodiments 38 to 65, where a ratio of the primary activating molecular ligands to the co-activating molecular ligands in the antigen-presenting covalently functionalized region of the surface is about 1:10 to about 2:1, about 1:5 to about 2:1, about 1:2 to about 2:1, about 1:10 to about 1:1, about 1:5 to about 1:1, about 1:1 to about 2:1, or optionally, about 1:2 to about 1:1.

67. The method of any one of embodiments 38 to 66, where a ratio of the TCR co-activating molecules to the adjunct TCR activating molecules of the plurality of co-activating molecular ligands is about 3:1 to about 1:3.

68. The method of any one of embodiments 38 to 67, where a ratio of the TCR co-activating molecules to the adjunct TCR activating molecules of the plurality of co-activating molecular ligands is about 2:1 to about 1:2.

69. The method of any one of embodiments 38 to 68, where a ratio of the TCR co-activating molecules to the adjunct TCR activating molecules of the plurality of co-activating molecular ligands is about 1:1.

70. The method of any one of embodiments 39 to 69, further including contacting the plurality of T cells with a plurality of adhesion-stimulating molecular ligands, and optionally, where the plurality of adhesion-stimulating molecular ligands include an ICAM molecule.

71. The method of embodiment 70, where the plurality of adhesion-stimulating molecular ligands is covalently attached to the region outside of the antigen-presenting covalently functionalized region of the surface of the well plate.

72. The method of any one of embodiments 38 to 71, further including contacting the plurality of T cells with a plurality of growth stimulatory molecular ligands.

73. The method of embodiment 72, where each of the growth stimulatory molecular ligands includes a growth factor receptor ligand.

74. The method of embodiment 73, where the growth factor receptor ligand includes IL-21 or a fragment thereof.

75. The method of any one of embodiments 72 to 74, where contacting with the plurality of growth stimulatory molecular ligands is performed after a first period of culturing of at least one day.

76. The method of any one of embodiments 38 to 75, where culturing in contact with the antigen-presenting synthetic surface is performed for a period from about four days to about seven days.

77. The method of any one of embodiments 38 to 76, further including: completing a first period of activation in contact with the antigen-presenting covalently functionalized region of the surface; and, culturing the plurality of activated T cells in contact with the antigen-presenting covalently functionalized region of the surface for a second period of culturing, thereby providing an expanded plurality of activated T cells.

78. The method of embodiment 77, further including adding a second plurality of growth stimulatory molecular ligands during the second culturing period.

79. The method of embodiment 77 or 78, where a plurality of IL-2 molecules and a plurality of IL-7 molecules are added to contact the activated T cells for a remainder of the second culturing period.

80. The method of any one of embodiments 76 to 79, where culturing in contact with the antigen-presenting covalently functionalized region of the surface is performed for a period from about four days to about seven days.

81. The method of any one of embodiments 77 to 80, further including: completing the second period of activation in contact with the antigen-presenting covalently functionalized region of the surface; and, culturing the expanded plurality of activated T cells in contact with the antigen-presenting covalently functionalized region of the surface for a third period of culturing, thereby providing a plurality of highly activated T cells.

82. The method of embodiment 81, further including adding a third plurality of growth stimulatory molecular ligands during the third culturing period.

83. The method of embodiment 81 or 82, where a plurality of IL-2 molecules and a plurality of IL-7 molecules are added to contact the activated T cells for a remainder of the third culturing period.

84. The method of any one of embodiments 81 to 83, where the culturing in contact with the antigen-presenting covalently functionalized region of the surface is performed for a third period from about four days to about seven days.

85. The method of any one of embodiments 38 to 84, where the activated T cell is CD45RO+.

86. The method of any one of embodiments 38 to 85, where the activated T cell is CD28 positive.

87. The method of any one of embodiments 38 to 86, where an area of the antigen-presenting functionalized region is less than about 50%, less than about 25%, less than about 15%, less than about 10%, less than about 5%, or less than about 2% of the area of a bottom surface of a well of the well plate.

88. A method of activating a lymphocyte, including contacting a plurality of lymphocytes with an activating moiety-presenting covalently functionalized region of a surface of a well plate, where the activating moiety-presenting covalently functionalized region includes a plurality of primary activating molecular ligands linked to the surface; and a plurality of co-activating molecular ligands linked to the surface; and culturing the plurality of lymphocytes, thereby converting at least a portion of the plurality of lymphocytes to activated lymphocytes.

89. The method of embodiment 88, where the lymphocytes include B cells, T cells or NK cells.

90. The method of embodiment 88 or 89, where the activating moiety-presenting covalently functionalized region is a first region of a surface of a well plate according to any one of embodiments 1 to 13.

91. The method of any one of embodiments 88 to 90, where the primary activating molecular ligands include a CD3 binding molecule or an MHC molecule (e.g., MHC Class I or MHC Class II).

92. The method of embodiment 91, where the plurality of MHC molecules each include an MHC Class I protein sequence and a beta microglobulin protein sequence.

93. The method of embodiment 91 or 92, where the MHC molecule further includes an antigenic peptide.

94. The method of embodiment 93, where the CD3 binding protein is an antibody or a fragment thereof that retains binding affinity.

95. The method of any one of embodiments 88 to 94, where the plurality of co-activating molecular ligands includes TCR co-activating molecules and adjunct TCR activating molecules.

96. The method of any one of embodiments 88 to 95, where the plurality of co-activating molecular ligands includes a CD2 binding molecule and/or a CD28 binding molecule.

97. The method of embodiments 95 or 96, where more than one type of co-activating molecular ligands are present, the ratio of differing co-activating molecular ligands is about 20:1 to about 1:20 or about 3:1 to about 1:3.

98. The method of any one of embodiments 88 to 97, where the plurality of specifically bound primary activating molecular ligands has a density of at least about $1 \times 10^2$ molecules per square micron, or from about $1 \times 10^2$ to about $1 \times 10^5$ molecules per square micron in the activating moiety-presenting covalently functionalized region of the surface.

99. The method of any one of embodiments 88 to 98, where the plurality of specifically bound co-activating molecular ligands has a density of at least $1 \times 10^2$ molecules per square micron, or from about $1 \times 10^2$ to about $1 \times 10^5$ molecules per square micron, or from about $1 \times 10^3$ to about $1 \times 10^5$ molecules per square micron in the activating moiety-presenting covalently functionalized region of the surface.

100. The method of any one of embodiments 88 to 99, where a ratio of the primary activating molecular ligands to the co-activating molecular ligands in the activating moiety-presenting covalently functionalized region e is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

101. The method of any one of embodiments 88 to 100, further including contacting the plurality of lymphocytes with a plurality of growth stimulatory molecular ligands.

102. The method of embodiment 1012, where each of the growth stimulatory molecular ligands includes a growth factor receptor ligand.

103. The method of embodiment 102, where the growth factor receptor ligand includes IL-21 or a fragment thereof.

104. The method of any one of embodiments 101 to 103, where contacting with the plurality of growth stimulatory molecular ligands is performed after a first period of culturing of at least one day.

105. The method of any one of embodiments 88 to 104, where culturing in contact with the activating moiety-presenting covalently functionalized region is performed for a period from about four days to about seven days.

106. The method of any one of embodiment 89 to 107, where an area of the activating moiety-presenting functionalized region is less than about 25%, less than about 15%, less than about 10%, less than about 5%, or less than about 2% of an area of a bottom surface of a well of the well plate.

107. A kit for preparing a well plate including a surface having an activating moiety-presenting covalently functionalized region, including a well plate including a surface including a reactive moiety-presenting covalently functionalized region, where the reactive moiety is an azido moiety, a biotin moiety or a streptavidin moiety; and an activating reagent; and optionally, a surface functionalization reagent.

108. The kit of embodiment 107, where the kit includes the surface functionalization reagent, and where the surface functionalization reagent is a biotin containing reagent or a streptavidin containing reagent configured to react with the reactive moiety.

109. The kit of embodiment 108, where the kit further includes both a biotin containing reagent and a streptavidin containing reagent.

110. The kit of any one of embodiments 107 to 109, where the well plate including the surface including the reactive moiety-presenting covalently functionalized region is the well plate of any one of embodiments 1 to 11, the well plate of any one of embodiments 31 to 33, or the well plate having the reactive moiety-presenting covalently functionalized region of any one of embodiments 33 to 37.

111. The kit of any one of embodiments 107 to 110, where the activating reagent includes a primary activating reagent including a plurality of major histocompatibility complex (MHC) molecules (e.g., Class I or Class II) configured to bind with a T cell receptor of the T cell, and configured to bind to a binding site of streptavidin or a plurality of CD3 binding molecules.

112. The kit of any one of embodiments 107 to 111, further including a co-activating reagent including a plurality of co-activating molecules, each configured to bind a binding site of streptavidin, and where each of the co-activating molecules includes a T cell receptor (TCR) co-activating molecule or an adjunct TCR activating molecule.

113. The kit of embodiment 112, where the plurality of co-activating molecules includes T cell receptor (TCR) co-activating molecules and adjunct TCR activating molecules.

114. The kit of any one of embodiments 107 to 113, further including a co-activating reagent including a plurality of co-activating molecules, each configured to bind a binding site of streptavidin, and where each of the co-activating molecules includes a CD2 binding molecule or a CD28 binding molecule.

115. The kit of any one of embodiments 107 to 114, further including a reagent including growth stimulatory molecules, where each growth stimulatory molecule includes a growth factor receptor ligand.

116. The kit of embodiment 115, where the growth factor receptor ligand includes IL-21 or a fragment thereof.

117. The kit of embodiment 115 or 116, further including a second growth stimulatory molecule including IL-7 or IL-2.

118. A well plate including a surface having an azido-presenting covalently functionalized region.

119. The well plate of embodiment 118, where each of one or more wells of the well plate includes a surface (i.e., an inner surface) having an azido-presenting covalently functionalized region.

120. The well plate of embodiment 119, where the azido-presenting covalently functionalized region of each of the one or more wells is located on a bottom surface of the corresponding well.

121. The well plate of any one of embodiments 118 to 120, where the surface of the well plate or the surface of the one or more wells of the well plate includes glass or polystyrene.

122. The well plate of any one of embodiments 118 to 121, where the surface of the well plate or one or more wells includes polypropylene, polycarbonate, polyethylene, cycloolefin copolymer, or melamine.

123. The well plate of any one of embodiments 118 to 122, where the azido-presenting covalently functionalized region has an area of at least 0.5 mm$^2$. In certain specific embodiments, the azido-presenting covalently functionalize region has an area of at least 1.0 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, at least 50 mm$^2$, at least 75 mm$^2$, at least 100 mm$^2$, at least 150 mm$^2$, at least 200 mm$^2$, at least 250 mm$^2$, at least 300 mm$^2$, at least 400 mm$^2$, at least 500 mm$^2$, at least 600 mm$^2$, at least 700 mm$^2$, at least 800 mm$^2$, at least 900 mm$^2$, at least 1,000 mm$^2$, at least 2,000 mm$^2$, at least 3,000 mm$^2$, at least 4,000 mm$^2$, at least 5,000 mm$^2$, at least 6,000 mm$^2$, at least 7,000 mm$^2$, at least 8,000 mm$^2$, at least 9,000 mm$^2$, at least 10,000 mm$^2$, at least 20,000 mm$^2$, at least 30,000 mm$^2$, at least 40,000 mm$^2$, at least 50,000 mm$^2$, at least 60,000 mm$^2$, at least 70,000 mm$^2$, at least 80,000 mm$^2$, at least 90,000 mm$^2$, at least 100,000 mm$^2$, or more (e.g., substantially all of the inner surface of a well, or each of two or more wells, of the well plate).

124. The well plate of any one of embodiments 118 to 123, where the azido-presenting covalently functionalized region has a density of azido groups of at least 50/um$^2$.

125. The well plate of any one of embodiments 118 to 124, where the azido-presenting covalently functionalized region includes azido functionalities linked covalently to the surface via a linker having five or more backbone atoms selected from carbon, silicon, nitrogen and oxygen. In specific embodiments, the linker can have from 5 to about 20 backbone atoms, or about 10 to about 40 backbone atoms, or a series of about 5, 7, 9, 10, 11, 13, 15, 20, 25, 30, 35, 40, 45, 50, 55, 60, 65, 70, 75, 80, 90, 100, 200 bond lengths, any number of bond lengths therebetween.

126. A well plate including a surface including a biotin-presenting covalently functionalized region. In certain embodiments, the surface includes a plurality of biotin-presenting covalently functionalized regions.

127. The well plate of embodiment 126, where each of one or more wells of the well plate includes a surface (i.e., an inner surface) having one (or more) biotin-presenting covalently functionalized region(s).

128. The well plate of embodiment 127, where the biotin-presenting covalently functionalized region(s) of each of the one or more wells is located on a bottom surface of the corresponding well.

129. The well plate of any one of embodiments 126 to 128, where the surface of the well plate or the surface of the one or more wells includes glass or polystyrene.

130. The well plate of any one of embodiments 126 to 129, where the surface of the well plate or the surface of the one or more wells includes polypropylene, polycarbonate, polyethylene, cycloolefin copolymer, or melamine.

131. The well plate of any one of embodiments 126 to 130, where each biotin-presenting covalently functionalized region has an area of at least 0.5 mm$^2$. In certain specific embodiments, each biotin-presenting covalently functionalize region has an area of at least 1.0 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, or at least 50 mm$^2$. In certain specific embodiments, each biotin-presenting covalently functionalize region has an area of no more than 100 mm$^2$.

132. The well plate of any one of embodiments 126 to 131, where each biotin-presenting covalently functionalized region has a density of biotin functionalities of at least 50/um$^2$.

133. The well plate of any one of embodiments 126 to 132, where each biotin-presenting covalently functionalized region includes biotin functionalities linked covalently to the surface via a linker having from ten or more backbone atoms selected from carbon, silicon, nitrogen and oxygen. In specific embodiments, the linker can have from about 10 to about 40 backbone atoms, or a series of about 5, 7, 9, 10, 11, 13, 15, 20, 25, 30, 35, 40, 45, 50, 55, 60, 65, 70, 75, 80, 90, 100, 200 bond lengths, any number of bond lengths therebetween.

134. The well plate of any one of embodiments 126 to 133, where the area of each biotin-presenting covalently functionalized region is less than about 50%, less than about 25%, less than about 15%, less than about 10%, less than about 5%, or less than about 2% of the area of the bottom surface of each of the one or more wells.

135. The well plate of any one of embodiments 126 to 134, where each biotin-presenting covalently functionalized region has a dimension of 0.5 to 4.0 mm (e.g., about 1.0 mm to about 35 mm, or about 1.5 mm to about 3.0 mm).

136. The well plate of any one of embodiments 126 to 135, where each biotin presenting covalently functionalized region is substantially circular and has a diameter of 0.5 to 4.0 mm (e.g., about 1.0 mm to about 35 mm, or about 1.5 mm to about 3.0 mm).

137. A well plate including a surface including a streptavidin-presenting covalently functionalized region. In certain embodiments, the surface includes a plurality of streptavidin-presenting covalently functionalized regions.

138. The well plate of embodiment 137, where each of one or more wells of the well plate includes a surface (i.e., inner surface) having one (or more) streptavidin-presenting covalently functionalized region(s).

139. The well plate of embodiment 138, where the streptavidin-presenting covalently functionalized region(s) of each of the one or more wells is located on a bottom surface of the corresponding well.

140. The well plate of any one of embodiments 137 to 139, where the surface of the well plate or one or more wells includes glass or polystyrene.

141. The well plate of any one of embodiments 137 to 140, where the surface of the well plate or one or more wells includes polypropylene, polycarbonate, polyethylene, cycloolefin copolymer, or melamine.

142. The well plate of any one of embodiments 137 to 141, where each streptavidin-presenting covalently functionalized region has an area of at least 0.5 mm$^2$. In certain specific embodiments, each streptavidin-presenting covalently functionalize region has an area of at least 1.0 mm$^2$, at least 2.0 mm$^2$, at least 3.0 mm$^2$, at least 4.0 mm$^2$, at least 5.0 mm$^2$, at least 6.0 mm$^2$, at least 7.0 mm$^2$, at least 8.0 mm$^2$, at least 9.0 mm$^2$, at least 10 mm$^2$, at least 15 mm$^2$, at least 20 mm$^2$, at least 25 mm$^2$, at least 30 mm$^2$, at least 35 mm$^2$, at least 40 mm$^2$, at least 45 mm$^2$, or at least 50 mm$^2$. In certain specific embodiments, each streptavidin-presenting covalently functionalize region has an area of no more than 100 mm$^2$.

143. The well plate of any one of embodiments 137 to 142, where each streptavidin-presenting covalently functionalized region has a density of streptavidin functionalities of at least 50/um$^2$.

144. The well plate of any one of embodiments 137 to 143, where each streptavidin functionality is covalently attached to the covalently functionalized region of the surface of the well plate or the one or more wells of the well plate.

145. The well plate of any one of embodiments 137 to 144, where each streptavidin functionality is non-covalently attached to a biotin moiety which is itself covalently attached to the covalently functionalized region of the surface of the well plate or the one or more wells of the well plate.

146. The well plate of any one of embodiments 138 to 145, where each streptavidin-presenting covalently functionalized region has an area of less than about 50% of an area of a bottom surface of each of the one or more wells.

147. The well plate of any one of embodiments 138 to 146, where the area of each streptavidin-presenting covalently functionalized region is less than about 25%, less than about 15%, less than about 10%, less than about 5%, or less than about 2% of the area of the bottom of each of the one or more wells.

148. The well plate of any one of embodiments 137 to 147, where each streptavidin-presenting covalently functionalized region has a dimension of 0.5 to 4.0 mm (e.g., about 1.0 mm to about 35 mm, or about 1.5 mm to about 3.0 mm).

149. The well plate of any one of embodiments 137 to 148, where each streptavidin-presenting covalently functionalized region is substantially circular and has a diameter of 0.5 to 4.0 mm (e.g., about 1.0 mm to about 35 mm, or about 1.5 mm to about 3.0 mm).

150. The well plate of any one of embodiments 126 to 149, where the surface of the well plate includes a plurality of biotin-presenting or streptavidin-presenting covalently functionalized regions.

151. The well plate of embodiment 150, where the plurality of biotin-presenting or streptavidin-presenting covalently functionalized regions are clustered on the bottom of a well of the well plate.

152. The well plate of embodiment 151, where an area of each of the plurality of biotin-presenting or streptavidin-presenting covalently functionalized regions is less than about 5%, less than about 2%, or less than about 1% of an area of the bottom of each of the one or more wells, and further where a total area of the plurality of regions is less than about 50% or less than about 25% of the area of the bottom of each of the one or more wells.

153. The well plate of any one of embodiments 137 to 152, where the streptavidin-presenting covalently functionalized region includes streptavidin functionalities linked covalently to the surface via a linker having ten or more backbone atoms selected from carbon, silicon, nitrogen and oxygen. In specific embodiments, the linker can have from about 10 to about 50 backbone atoms, or a series of about 5, 7, 9, 10, 11, 13, 15, 20, 25, 30, 35, 40, 45, 50, 55, 60, 65, 70, 75, 80, 90, 100, 200 bond lengths, any number of bond lengths therebetween.

154. The well plate of any one of embodiments 126 to 153, where the surface of the well plate or each of the one or more wells further includes a second covalently modified region including surface blocking ligands.

155. The well plate of embodiment 154, where each of the surface blocking ligands includes a hydrophilic or negatively charged moiety.

156. The well plate of embodiment 154 or 155, where the surface blocking ligands include polyethylene glycol (PEG) moieties.

157. The well plate of any one of embodiments 154 to 156, where the second covalently modified region further includes at least one ligand providing a moiety stimulating adherence.

158. The well plate of any one of embodiments 137 to 157, where the streptavidin functionality is covalently or non-covalently attached to the covalently functionalized region of the surface of any one of embodiments 122 to 129.

159. A well plate including a surface including an antigen-presenting covalently functionalized region of the well plate for activating a T cell.

160. The well plate of embodiment 159, where each of one or more wells of the well plate includes a surface having an antigen-presenting covalently functionalized region.

161. The well plate of embodiment 159 or 160, where the antigen-presenting covalently functionalized region of each of the one or more wells is located on a bottom surface of the corresponding well.

162. The well plate of any one of embodiments 159 to 161, where the antigen-presenting covalently functionalized region includes a plurality of specifically bound primary activating molecular ligands and a plurality of specifically bound co-activating molecular ligands.

163. The well plate of embodiment 162, where the plurality of specifically bound primary activating molecular ligands each includes a major histocompatibility complex (MHC) molecule (e.g., Class I or Class II) configured to bind to a T cell receptor of the T cell.

164. The well plate of embodiment 163, where the MHC molecule includes an MHC Class I protein sequence and a beta microglobulin protein sequence.

165. The well plate of embodiment 163 or 164, where each of the plurality of primary activating molecules including an MHC molecule further includes an antigenic peptide, and optionally a tumor associated antigen, a viral antigen, a bacterial antigen, a fungal antigen, or a protozoan antigen.

166. The well plate of embodiment 165, where the antigenic peptide is a tumor associated antigen, and optionally, the tumor associated antigen is SLC45A2, TCL1, VCX3A, MART1 or NYESO1.

167. The well plate of any one of embodiments 163 to 166, where the protein sequence of the MHC molecule is connected to the antigen-presenting synthetic surface via a C-terminal connection of the protein sequence.

168. The well plate of any one of embodiments 162 to 167, where the plurality of specifically bound co-activating molecular ligands each include a T cell receptor (TCR) co-activating molecule or an adjunct TCR activating molecule.

169. The well plate of embodiment 168, where a ratio of the TCR co-activating molecules to the adjunct TCR activating molecules of the plurality of co-activating molecular ligands is about 100:1 to about 1:100.

170. The well plate of any one of embodiments 168 to 169, where a ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, where each of the foregoing values is modified by "about".

171. The well plate of any one of embodiments 168 to 170, where a ratio of the TCR co-activating molecules to the adjunct TCR activating molecules of the plurality of co-activating molecular ligands is from about 20:1 to about 1:20 or about 3:1 to about 1:3.

172. The well plate of any one of embodiments 168 to 171, where the TCR co-activating molecules include a CD28 binding protein or a fragment thereof, which retains binding ability to CD28.

173. The well plate of embodiment 172, where the CD28 binding protein or the fragment thereof further includes a site-specific C-terminal biotin moiety.

174. The well plate of any one of embodiments 168 to 173, where the T cell receptor (TCR) co-activating molecules include a CD80 molecule or a fragment thereof, where the fragment retains binding activity to CD28.

175. The well plate of any one of embodiments 168 to 174, where the T cell receptor (TCR) co-activating molecule includes an anti-CD28 antibody or a fragment thereof.

176. The well plate of any one of embodiments 168 to 175, where the adjunct TCR activating molecule includes a CD2 binding protein.

177. The well plate of embodiment 176, where the CD2 binding protein or the fragment thereof further includes a site-specific C-terminal biotin moiety.

178. The well plate of any one of embodiments 168 to 179, where the adjunct TCR activating molecule includes a CD58 molecule or fragment thereof, where the fragment retains binding activity with CD2.

179. The well plate of any one of embodiments 168 to 178, where the adjunct TCR activating molecule includes an anti-CD2 antibody or a fragment thereof.

180. The well plate of any one of embodiments 166 to 179, where the plurality of specifically bound primary activating molecular ligands and a plurality of specifically bound co-activating molecular ligands are specifically bound to streptavidin functionalities of the streptavidin-presenting covalently functionalized region of the well plate of any one of embodiments 1 to 11, embodiments 31 to 33, or any one of embodiments 137 to 159

181. The well plate of any one of embodiments 166 to 180, where the plurality of specifically bound primary activating molecular ligands has a density of at least about $1 \times 10^2$ molecules per square micron or from about $1 \times 10^2$ to about $1 \times 10^5$ molecules per square micron in the antigen-presenting covalently functionalized region.

182. The well plate of any one of embodiments 166 to 181, where the plurality of specifically bound co-activating molecular ligands has a density from about $1 \times 10^2$ to about $1 \times 10^5$ molecules per square micron or about $1 \times 10^3$ to about $1 \times 10^5$ molecules per square micron in the antigen-presenting covalently functionalized region.

183. A method of preparing a well plate including a surface having an azido-presenting covalently functionalized region, the method including: contacting oxide moieties of a portion of the surface of the well plate with an azido-containing coupling reagent; and forming the azido-presenting covalently functionalized region of the well plate.

184. The method of embodiment 183, where the method further includes plasma cleaning the surface of the well plate before the contacting of the oxide moieties of the portion of the surface with the azido containing coupling reagent.

185. The method of embodiment 183 or 184, where the azido containing coupling reagent is present in a gaseous phase when the contacting occurs.

186. The method of any one of embodiments 183 to 185, where the azido containing coupling reagent includes a linker having a carbon backbone of 5 to 9 carbons.

187. The method of embodiment 186, where the linker has a carbon backbone of 7 carbons.

188. The method of any one of embodiments 183 to 187, where the surface of the well plate includes (or consists of, or consists essentially of) glass, polystyrene, polypropylene, polycarbonate, polyethylene, cycloolefin copolymer or melamine 189. The method of any one of embodiments 183 to 188, where the azido-presenting covalently functionalized region has a density of azido groups of at least $50/um^2$.

190. The method of any one of embodiments 183 to 189, where contacting oxide moieties of the portion of the surface of the well plate with an azido-containing coupling reagent includes contacting a surface of each of one or more wells of the well plate with the azido-containing coupling reagent, thereby forming a surface having an azido-presenting covalently functionalized region in each of the one or more wells.

191. The method of embodiment 190, where the contacting the surface of the one or more wells includes contacting a bottom surface of the corresponding well with the azido-containing coupling reagent thereby forming an azido-presenting covalently functionalized region on the bottom surface of each of the one or more wells.

192. The method of embodiment 191, where the contacting the bottom surface of each of the one or more wells includes contacting only the bottom surface, thereby forming an azido-presenting covalently functionalized region on only the bottom surface of each of the one or more wells.

193. A method of preparing a well plate including a surface having a biotin-presenting covalently functionalized region, the method including: contacting a portion of the surface of the well plate with a reagent including a biotin moiety linked to a reactive group, where the reactive group is configured to react with reactive moieties of the surface, thereby forming a biotin-presenting functionalized region of the well plate; and contacting the surface of the well plate with a reagent including surface blocking ligands linked to a reactive group, where the reactive group is configured to react with reactive moieties of the surface, thereby providing a blocking ligand-modified region of the surface.

194. The method of embodiment 193, where the blocking ligand-modified region and the biotin-presenting region cover the entire surface, and optionally, where the blocking ligand-modified region and the biotin-presenting region are non-overlapping regions of the surface.

195. The method of embodiment 193 or 194, where contacting the portion of the surface of the well plate with the reagent including the biotin moiety linked to the reactive group includes contacting a surface within each of one or more wells of the well plate.

196. The method of embodiment 195, where contacting each of the one or more wells further includes contacting each of the one or more wells at a bottom surface of the corresponding well with the reagent including the biotin moiety linked to the reactive group thereby producing the biotin-presenting covalently functionalized region on the bottom surface of the corresponding well.

197. The method of embodiment 196, where the biotin-presenting covalently functionalized region is formed only on the bottom surface of the corresponding well.

198. The method of any one of embodiments 193 to 197, where the biotin-presenting covalently functionalized region has a density of biotin functionalities of at least $50/um^2$.

199. The method of any one of embodiments 193 to 198, where the biotin-presenting covalently functionalized region has an area of less than about 50% of an area of the bottom of each of the one or more wells.

200. The method of any one of embodiments 193 to 199, where an area of the biotin-presenting covalently functionalized region is less than about 25%, less than about 15%, less than about 10%, less than about 5%, less than about 2%, or less than about 1% of the area of the bottom of each of the one or more wells.

201. The method of any one of embodiments 193 to 200, where an area of the biotin-presenting covalently functionalized region has an area of less than about 35 $mm^2$, about 20 $mm^2$, about 12 $mm^2$, about 5 $mm^2$, less than about 2 $mm^2$, or less than about 1 $mm^2$.

202. The method of any one of embodiments 193 to 201, where the biotin-presenting covalently functionalized region has a dimension of about 0.5 mm to about 4.0 mm (e.g., about 1.0 mm to about 35 mm, or about 1.5 mm to about 3.0 mm).

203. The method of any one of embodiments 193 to 202, where the biotin-presenting covalently functionalized region is substantially circular and has a diameter of about 0.5 mm to about 4.0 mm (e.g., about 1.0 mm to about 35 mm, or about 1.5 mm to about 3.0 mm).

204. The method of any one of embodiments 196 to 203, further including contacting a plurality of regions of the bottom of each of the one or more wells with the reagent including the biotin moiety linked to the reactive group, thereby producing a plurality of biotin-presenting regions in each of the one or more wells.

205. The method of any one of embodiments 193 to 204, where the reagent including the biotin moiety linked to the reactive group is a copper-dependent Click coupling reagent.

206. The method of embodiment 205, further including contacting the surface of the well plate with a thiol-containing reagent or a copper-chelating reagent subsequent to contacting the portion of the surface with the copper-dependent Click coupling reagent and prior to contacting the surface with the reagent including surface blocking ligands.

207. The method of any one of embodiments 193 to 206, where each of the surface blocking ligands includes a hydrophilic or negatively charged moiety.

208. The method of any one of embodiments 193 to 207, where the surface blocking ligands include polyethylene glycol (PEG) moieties.

209. The method of any one of embodiments 196 to 208, further including contacting one or more surfaces of each of the one or more wells with a reagent including a ligand configured to provide adherence stimulation, where the contacting is performed after contacting the surface of each of the one or more wells with the reagent including the biotin moiety linked to the reactive group, thereby disposing ligands configured to provide adherence stimulation outside of the biotin-presenting region of the one or more wells.

210. The method of any one of embodiments 193 to 209, where the reactive moieties are disposed within one or more wells of the well plate.

211. The method of any one of embodiments 1937 to 2104, where the reactive moieties of the surface include azido or alkynyl reactive moieties.

212. The method of any one of embodiments 193 to 211, where the well plate includes glass, polystyrene, polypropylene, polycarbonate, polyethylene, cycloolefin copolymer or melamine 213. A method of preparing a well plate including a surface having a streptavidin-presenting covalently functionalized region, the method including contacting a portion of the surface of the well plate with a reagent including a streptavidin functionality linked to a reactive group or a reagent including a biotin moiety linked to a reactive group, where the reactive group is configured to react with reactive moieties of the surface, and, when the reagent includes the biotin moiety linked to the reactive group, subsequently contacting the portion of the surface with streptavidin, thereby forming a streptavidin-presenting functionalized region of the well plate, and contacting the surface of the well plate with a reagent including surface blocking ligands linked to a reactive group, where the reactive group is configured to react with reactive moieties of the surface, thereby providing a blocking ligand-modified region of the surface.

214. The method of embodiment 213, where the blocking ligand-modified region and the streptavidin-presenting region cover the entire surface, and optionally, where the blocking ligand-modified region and the streptavidin-presenting region are non-overlapping regions of the surface.

215. The method of embodiment 213 or 214, where contacting the portion of the surface of the well plate with the reagent including the streptavidin moiety linked to the reactive group or the reagent including the biotin moiety includes contacting a surface within each of one or more wells of the well plate.

216. The method of embodiment 215, where contacting each of the one or more wells further includes contacting each of the one or more wells at a bottom surface of the corresponding well with the reagent including the streptavidin moiety linked to the reactive group or with the reagent including the biotin moiety linked to the reactive group, thereby producing the streptavidin-presenting covalently functionalized region on the bottom surface of the corresponding well.

217. The method of embodiment 216, where the streptavidin-presenting covalently functionalized region is formed only on the bottom surface of the corresponding well.

218. The method of any one of embodiments 213 to 217, where the streptavidin—presenting covalently functionalized region has a density of streptavidin functionalities of at least $50/um^2$.

219. The method of any one of embodiments 213 to 218, where the streptavidin—presenting covalently functionalized region has an area of less than about 50% of an area of the bottom of each of the one or more wells.

220. The method of any one of embodiments 213 to 219, where an area of the streptavidin-presenting covalently functionalized region is less than about 25%, less than about 15%, less than about 10%, less than about 5%, less than about 2%, or less than about 1% of the area of the bottom of each of the one or more wells.

221. The method of any one of embodiments 213 to 220, where an area of the streptavidin-presenting covalently functionalized region has an area of less than about 35 $mm^2$, about 20 $mm^2$, about 12 $mm^2$, about 5 $mm^2$, less than about 2 $mm^2$, or less than about 1 $mm^2$.

222. The method of any one of embodiments 213 to 221, where the streptavidin-presenting covalently functionalized region has a dimension of about 0.5 mm to about 4.0 mm (e.g., about 1.0 mm to about 35 mm, or about 1.5 mm to about 3.0 mm).

223. The method of any one of embodiments 213 to 222, where the streptavidin-presenting covalently functionalized region is substantially circular and has a diameter of about 0.5 mm to about 4.0 mm (e.g., about 1.0 mm to about 35 mm, or about 1.5 mm to about 3.0 mm).

224. The method of any one of embodiments 213 to 223, further including contacting a plurality of regions of the bottom of each of the one or more wells with the reagent including the streptavidin moiety linked to the reactive group or with the reagent including the biotin moiety linked to the reactive group, thereby producing a plurality of streptavidin-presenting regions in each of the one or more wells.

225. The method of any one of embodiments 213 to 224, where the reagent including the streptavidin moiety linked to the reactive group or the reagent including the biotin moiety linked to the reactive group is a copper-dependent Click coupling reagent.

226. The method of embodiment 225, further including contacting the surface of the well plate with a thiol-containing reagent or a copper-chelating reagent subsequent to contacting the portion of the surface with the copper-dependent Click coupling reagent and prior to contacting the surface with the reagent including surface blocking ligands.

227. The method of any one of embodiments 213 to 226, where each of the surface blocking ligands includes a hydrophilic or negatively charged moiety.

228. The method of any one of embodiments 213 to 227, where the surface blocking ligands include polyethylene glycol (PEG) moieties.

229. The method of any one of embodiments 215 to 228, further including contacting one or more surfaces of each of the one or more wells with a reagent including a ligand configured to provide adherence stimulation, where the contacting is performed after contacting the surface of each of the one or more wells with the reagent including the streptavidin moiety linked to the reactive group or with the reagent including the biotin moiety, thereby disposing ligands configured to provide adherence stimulation outside of the streptavidin-presenting region of the one or more wells.

230. The method of any one of embodiments 213 to 229, where the reactive moieties are disposed within one or more wells of the well plate.

231. The method of any one of embodiments 213 to 230, where the reactive moieties of the surface include azido or alkynyl reactive moieties.

232. The method of any one of embodiments 213 to 231, where the well plate includes glass, polystyrene, polypropylene, polycarbonate, polyethylene, cycloolefin copolymer or melamine 233. A method of preparing a well plate including a surface having a streptavidin-presenting covalently functionalized region, including forming an reactive moiety-presenting covalently functionalized surface on the surface; contacting the surface with a reagent including a streptavidin moiety linked to a reactive group or a reagent including a biotin moiety linked to a reactive group, where the reactive group is configured to react with the reactive moieties of the reactive moiety-presenting surface, thereby forming a streptavidin-presenting functionalized region or a biotin-presenting functionalized surface, where when the reagent includes the biotin moiety linked to the reactive group, subsequently contacting the portion of the well plate with streptavidin, and further where the reactive moiety-presenting covalently functionalized ligands of the surface or the biotin-presenting functionalized surface includes a UV labile linking moiety; exposing the surface to UV illumination through a mask configured to expose all surfaces outside of a portion of the surface; and cleaving the UV labile linkers of exposed streptavidin or biotin modified surface ligands, thereby forming a streptavidin-presenting covalently functionalized region of the well plate.

234. The method of embodiment 233, where forming the reactive moiety-presenting covalently functionalized surface includes reacting a reactive moiety-containing coupling reagent with oxide moieties of the surface of the well plate, where the reactive moiety containing-coupling reagent further includes the UV labile linking moiety.

235. The method of embodiment 233 or 234, where the method further includes plasma cleaning the surface of the well plate before contacting the oxide moieties of the surface with the reactive moiety-containing coupling reagent.

236. The method of any one of embodiments 233 to 235, where contacting the surface of the well plate with the reagent including the streptavidin moiety linked to the reactive group or the reagent including the biotin moiety includes contacting a surface within each of one or more wells of the well plate.

237. The method of embodiment 236, where contacting each of the one or more wells further includes contacting each of the one or more wells at a bottom surface of the corresponding well with the reagent including the streptavidin moiety linked to the reactive group or with the reagent including the biotin moiety linked to the reactive group, thereby producing the streptavidin-presenting covalently functionalized region on the bottom surface of the corresponding well.

238. The method of embodiment 237, where the streptavidin-presenting covalently functionalized region is formed only on the bottom surface of the corresponding well.

239. The method of any one of embodiments 233 to 238, where the streptavidin—presenting covalently functionalized region has a density of streptavidin functionalities of at least 50/um$^2$.

240. The method of any one of embodiments 233 to 239, where the reactive moieties of the surface include azido moieties or alkynyl moieties.

241. The method of any one of embodiments 236 to 240, where forming the streptavidin-presenting covalently functionalized region includes forming the streptavidin-presenting covalently functionalized region only on the bottom of the one or more wells of the well plate.

242. A method of preparing a well plate including a surface having an antigen-presenting covalently functionalized region for activating a T cell, including contacting a streptavidin-presenting covalently functionalized region of the well plate with a plurality of primary activating molecules, each including a major histocompatibility complex (MHC) Class I molecule configured to bind to a T cell receptor of the T cell and a binding moiety, where the binding moieties of the plurality of primary activating molecules, are configured to bind a binding site of streptavidin; and contacting a plurality of co-activating molecules, each including a T cell receptor (TCR) co-activating molecule; or an adjunct TCR activating molecule, where the co-activating molecules each further include a binding moiety configured to bind a binding site of streptavidin, with a second plurality of binding moieties of the streptavidin-presenting covalently functionalized the region of the well plate, thereby providing a plurality of specifically bound primary activating molecular ligands and a plurality of specifically bound co-activating molecular ligands of an antigen-presenting covalently functionalized region of the well plate.

243. The method of embodiment 242, further including contacting the surface of the well plate with a reagent including surface blocking ligands linked to a reactive group, where the reactive group is configured to react with reactive moieties of the surface, thereby providing a blocking ligand-modified region of the surface.

244. The method of embodiment 243, where the blocking ligand-modified region and the antigen-presenting covalently functionalized region cover the entire surface, and optionally, where the blocking ligand-modified region and the antigen-presenting covalently functionalized region are non-overlapping regions of the surface.

245. The method of any one of embodiments 242 to 244, where contacting the streptavidin-presenting covalently functionalized region of the well plate with the plurality of primary activating molecules and the plurality of co-activating molecules includes contacting a surface within each of one or more wells of the well plate.

246. The method of embodiment 245, where contacting each of the one or more wells further includes contacting each of the one or more wells at a bottom surface of the corresponding well with the plurality of primary activating molecules and the plurality of co-activating molecules, thereby producing the antigen-presenting covalently functionalized region on the bottom surface of the corresponding well.

247. The method of embodiment 246, where the antigen-presenting covalently functionalized region is formed only on the bottom surface of the corresponding well.

248. The method of any one of embodiments 242 to 247, where the streptavidin—presenting covalently functionalized region has a density of streptavidin functionalities of at least 50/um2.

249. The method of any one of embodiments 245 to 248, where the antigen-presenting covalently functionalized region has an area of less than about 50% of an area of the bottom of the one or more wells.

250. The method of any one of embodiments 245 to 248, where an area of the antigen-presenting covalently functionalized region is less than about 25%, less than about 15%, less than about 10%, less than about 5%, less than about 2%, or less than about 1% of the area of the bottom of the one or more wells.

251. The method of any one of embodiments 242 to 250, where an area of the antigen-presenting covalently functionalized region has an area of less than about 35 mm$^2$, less than about 20 mm$^2$, less than about 12 mm$^2$, less than about 5 mm$^2$, less than about 2 mm$^2$, or less than about 1 mm$^2$.

252. The method of any one of embodiments 242 to 251, where the antigen-presenting covalently functionalized region has a dimension of about 0.5 mm to about 4.0 mm (e.g., about 1.0 mm to about 35 mm, or about 1.5 mm to about 3.0 mm).

253. The method of any one of embodiments 242 to 252, where the antigen-presenting covalently functionalized region is substantially circular and has a diameter of about 0.5 mm to about 4.0 mm (e.g., about 1.0 mm to about 35 mm, or about 1.5 mm to about 3.0 mm).

254. The method of any one of embodiments 245 to 253, where contacting the streptavidin-presenting covalently functionalized region of the well plate with the plurality of primary activating molecules and the plurality of co-activating molecules further includes contacting a plurality of streptavidin-presenting covalently functionalized regions within each of one or more wells of the well plate, thereby producing a plurality of antigen-presenting covalently functionalized regions in each of the one or more wells.

255. The well plate of embodiment 254, where an area of each of the plurality of antigen-presenting covalently functionalized regions is less than about 5% of an area of the bottom of the one or more wells, and further where a total area of the plurality of antigen-presenting covalently functionalized regions is less than about 50%, about 25%, or about 10% of the area of the bottom of the one or more wells.

256. The method of any one of embodiments 242 to 255, where the reactive moieties of the surface are azido or alkynyl reactive moieties.

257. The method of any one of embodiments 242 to 254, where the well plate includes glass, polystyrene, polypropylene, polycarbonate, polyethylene, cycloolefin copolymer or melamine 258. The method of any one of embodiments 242 to 257, where the MHC molecule includes an MHC Class I protein sequence and a beta microglobulin protein sequence.

259. The method of any one of embodiments 242 to 258, where each of the plurality of primary activating molecules including an MHC molecule further includes a tumor associated antigen.

260. The method of embodiment 259, where the tumor associated antigen is SLC45A2, TCL1, VCX3A, MART1 or NYESO1.

261. The method of any one of embodiments 242 to 260, where the protein sequence of the MHC molecule is connected to the surface via a C-terminal connection of the protein sequence.

262. The method of any one of embodiments 242 to 261, where the MHC molecule includes a biotin moiety and is attached to the surface via a noncovalent interaction with streptavidin.

263. The method of any one of embodiments 242 to 262, where the streptavidin is itself covalently bonded to the surface.

264. The method of any one of embodiments 242 to 263, where the streptavidin is bonded to the surface through a series of about 5, 7, 9, 10, 11, 13, 15, 20, 25, 30, 35, 40, 45, 50, 55, 60, 65, 70, 75, 80, 90, 100, 200 bond lengths, or any number of bond lengths therebetween.

265. The method of any one of embodiments 242 to 264, where the streptavidin is noncovalently associated with the surface.

266. The method of embodiment 265, where the streptavidin is noncovalently associated with a biotin moiety, and the biotin moiety is covalently bonded to the surface.

267. The method of embodiment 262, where the biotin is linked by a linker to the surface through about 5, 7, 9, 10, 11, 13, 15, 20, 25, 30, 35, 40, 45, 50, 55, 60, 65, 70, 75, 80, 85, 95, 100, 200 bond lengths, or any number of bond lengths therebetween.

268. The method of any one of embodiments 242 to 267, where a ratio of the primary activating molecular ligands to the co-activating molecular ligands in the antigen-presenting covalently functionalized region is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

269. The method of any one of embodiments 242 to 268, where a ratio of the TCR co-activating molecules to the adjunct TCR activating molecules of the plurality of co-activating molecular ligands is about 100:1 to about 1:100.

270. The method of any one of embodiments 242 to 269, where a ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, where each of the foregoing values is modified by "about".

271. The method of any one of embodiments 242 to 270, where the ratio of the TCR co-activating molecules to the adjunct TCR activating molecules of the plurality of co-activating molecular ligands is from about 20:1 to about 1:20 or about 3:1 to about 1:3.

272. The method of any one of embodiments 242 to 271, where the plurality of specifically bound primary activating molecular ligands has a density of at least about $1 \times 10^2$ molecules per square micron or from about $1 \times 10^2$ to about $1 \times 10^5$ molecules per square micron in the antigen-presenting covalently functionalized region.

273. The well plate of any one of embodiments 242 to 272, where the plurality of specifically bound co-activating molecular ligands has a density from about $1 \times 10^2$ to about $1 \times 10^5$ molecules per square micron or about $1 \times 10^3$ to about $1 \times 10^5$ molecules per square micron on the antigen-presenting synthetic surface in the antigen-presenting covalently functionalized region.

274. The method of any one of embodiments 242 to 273, where the T cell receptor (TCR) co-activating molecule includes a CD28 binding protein or a fragment thereof which retains binding ability to CD28.

275. The method of embodiment 274, where the CD28 binding protein or the fragment thereof further includes a site-specific C-terminal biotin moiety.

276. The method of any one of embodiments 242 to 273, where the T cell receptor (TCR) co-activating molecule includes a CD80 molecule or a fragment thereof, where the fragment retains binding activity to CD28.

277. The method of any one of embodiments 242 to 273, where the T cell receptor (TCR) co-activating molecule includes an anti-CD28 antibody or a fragment thereof.

278. The method of any one of embodiments 242 to 277, where the adjunct TCR activating molecule includes a CD2 binding protein.

279. The method of embodiment 278, where the CD2 binding protein or the fragment thereof further includes a site-specific C-terminal biotin moiety.

280. The method of any one of embodiments 242 to 277, where the adjunct TCR activating molecule includes a CD58 molecule or fragment thereof, where the fragment retains binding activity with CD2.

281. The method of any one of embodiments 242 to 277, where the adjunct TCR activating molecule includes an anti-CD2 antibody or a fragment thereof.

282. The method of any one of embodiments 242 to 281, where each of the surface blocking ligands includes a hydrophilic or negatively charged moiety.

283. The method of any one of embodiments 242 to 282, where the surface blocking ligands include polyethylene glycol (PEG) moieties.

284. A method of preparing a well plate including a surface having a lymphocyte activating covalently functionalized region, including contacting a streptavidin-presenting covalently functionalized region of the well plate with a plurality of first activating molecules each including a binding moiety, where the binding moieties of the first activating molecules are configured to bind a binding site of streptavidin, thereby providing the lymphocyte activating covalently functionalized region.

285. The method of embodiment 284, further including contacting the surface of the well plate with a reagent including surface blocking ligands linked to a reactive group, where the reactive group is configured to react with reactive moieties of the surface, thereby providing a blocking ligand-modified region of the surface.

286. The method of embodiment 285, where the blocking ligand-modified region and the lymphocyte activating covalently functionalized region cover the entire surface, and optionally, where the blocking ligand-modified region and the lymphocyte activating covalently functionalized region are non-overlapping regions of the surface.

287. The method of any one of embodiments 284 to 286, where contacting the streptavidin-presenting covalently functionalized region of the well plate with the plurality of first activating molecules includes contacting a surface within each of one or more wells of the well plate.

288. The method of embodiment 287, where contacting each of the one or more wells further includes contacting each of the one or more wells at a bottom surface of the corresponding well with the plurality of first activating molecules, thereby producing the lymphocyte activating covalently functionalized region on the bottom surface of the corresponding well.

289. The method of embodiment 288, where the lymphocyte activating covalently functionalized region is formed only on the bottom surface of the corresponding well.

290. The method of any one of embodiments 284 to 287, where the streptavidin-presenting covalently functionalized region has a density of streptavidin functionalities of at least $50/um^2$.

291. The method of any one of embodiments 287 to 290, where the lymphocyte activating covalently functionalized region has an area of less than about 50% of an area of the bottom of the one or more wells.

292. The method of any one of embodiments 287 to 291, where an area of the lymphocyte activating covalently functionalized region is less than about 25%, less than about 15%, less than about 10%, less than about 5%, less than about 2%, or less than about 1% of the area of the bottom of the one or more wells.

293. The method of any one of embodiments 284 to 292, where an area of the lymphocyte activating covalently functionalized region has an area of less than about 35 mm$^2$, about 20 mm$^2$, about 12 mm$^2$, about 5 mm$^2$, less than about 2 mm$^2$, or less than about 1 mm$^2$.

294. The method of any one of embodiments 284 to 293, where the lymphocyte activating covalently functionalized region has a dimension of about 0.5 mm to about 4.0 mm (e.g., about 1.0 mm to about 35 mm, or about 1.5 mm to about 3.0 mm).

295. The method of any one of embodiments 284 to 294, where the lymphocyte activating covalently functionalized region is substantially circular and has a diameter of about 0.5 mm to about 4.0 mm (e.g., about 1.0 mm to about 35 mm, or about 1.5 mm to about 3.0 mm).

296. The method of any one of embodiments 284 to 295, where contacting the streptavidin-presenting covalently functionalized region of the well plate with the plurality of first activating molecules further includes contacting a plurality of streptavidin-presenting covalently functionalized regions with the plurality of first activating molecules within each of one or more wells of the well plate, thereby producing a plurality of lymphocyte activating covalently functionalized regions in each of the one or more wells.

297. The well plate of embodiment 296, where an area of each of the plurality of lymphocyte activating covalently functionalized regions is less than about 5% of an area of the bottom of the one or more wells, and further where a total area of the plurality of lymphocyte activating covalently functionalized regions is less than about 50%, about 25%, or about 10% of the area of the bottom of the one or more wells.

298. The method of any one of embodiments 284 to 297, where the reactive moieties of the surface are azido or alkynyl reactive moieties.

299. The method of any one of embodiments 284 to 298, where the well plate includes glass, polystyrene, polypropylene, polycarbonate, polyethylene, cycloolefin copolymer or melamine 300. The method of any one of embodiments 284 to 299, where the lymphocyte is a T cell, a Natural Killer T (NKT) cell, or a B cell.

301. The method of any one of embodiments 284 to 300, where the plurality of first activating molecules are cell surface clusters of differentiation binding molecules, cell surface immunoglobulin binding molecules, T-cell receptor molecule activating molecules, TNF receptor superfamily binding molecules, chemokine receptor binding molecules, growth factor molecules, or adhesion promoting molecules.

302. The method of embodiment 301, where the plurality of first activating molecules include an MHC molecule, a protein or fragment thereof retaining cell surface clusters of differentiation binding activity, a protein or fragment thereof retaining cell surface immunoglobulin binding ability, a protein or fragment thereof retaining T cell receptor binding activity, a protein or fragment thereof retaining TNF receptor superfamily binding activity, a protein or fragment thereof retaining chemokine receptor binding activity, a protein or fragment thereof retaining growth stimulatory activity or a protein or fragment thereof retaining adhesion promoting activity.

303. The method of embodiment 301 or 302, where the plurality of first activating molecules include a protein or fragment thereof retaining cell surface clusters of differentiation binding activity, a protein or fragment thereof retaining growth stimulatory activity or a protein or fragment thereof retaining adhesion promoting activity.

304. The method of any one of embodiments 284 to 303, where the plurality of specifically bound first activating molecular ligands has a density of at least about $1\times10^2$ molecules per square micron or from about $1\times10^2$ to about $1\times10^5$ molecules per square micron in the lymphocyte activating covalently functionalized region.

305. The method of any one of embodiments 284 to 304, further including contacting the streptavidin-presenting covalently functionalized region of the well plate with a plurality of second activating molecules each including a binding moiety, where the binding moieties of the second activating molecules are configured to bind a binding site of streptavidin, thereby providing a plurality of specifically bound second activating molecular ligands in the lymphocyte activating covalently functionalized region.

306. The method of embodiment 305, where the plurality of second activating molecules are T cell receptor (TCR) co-activating molecules, cell surface immunoglobulin binding molecules, growth factor molecules, adhesion promoting molecules.

307. The well plate of embodiment 304 or 305, where the plurality of specifically bound co-activating molecular ligands has a density from about 1×10² to about 1×10⁵ molecules per square micron or about 1×10³ to about 1×10⁵ molecules per square micron in the lymphocyte activating covalently functionalized region.

308. The method of any one of embodiments 284 to 307, where a ratio of the primary activating molecular ligands to the co-activating molecular ligands in the lymphocyte-activating covalently functionalized region is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

309. The method of any one of embodiments 285 to 308, where the blocking ligand-modified region and the antigen-presenting covalently functionalized region cover the entire surface, and optionally, where the blocking ligand-modified region and the lymphocyte activating covalently functionalized region are non-overlapping regions of the surface.

310. The method of any one of embodiments 285 to 309, where each of the surface blocking ligands includes a hydrophilic or negatively charged moiety.

311. The method of any one of embodiments 285 to 310, where the surface blocking ligands include polyethylene glycol (PEG) moieties.

312. A kit for preparing a well plate including a surface having an antigen-presenting covalently functionalized region, including a well plate including a surface including a biotin-presenting covalently functionalized region; and a surface functionalization reagent including streptavidin.

313. The kit of embodiment 312, where the well plate including the surface including the biotin-presenting covalently functionalized region is the well plate of any one of embodiments 1 to 11 where the reactive moiety is biotin, or any one of embodiments 31 to 33 where the reactive moiety is biotin, or any one of embodiments 126 to 136.

314. The kit of embodiment 312 or 313, further including a first activating reagent including a plurality of major histocompatibility complex (MHC) molecules (e.g., Class I or Class II) configured to bind with a T cell receptor of the T cell, and further where the MHC molecules are configured to bind to a binding site of streptavidin.

315. The kit of any one of embodiments 312 to 314, where each of the plurality of MHC molecules further includes at least one biotin functionality.

316. The kit of any one of embodiments 312 to 315, further including a reagent including a plurality of co-activating molecules, each configured to bind a binding site of streptavidin, and where each of the co-activating molecules includes a T cell receptor (TCR) co-activating molecule or an adjunct TCR activating molecule.

317. The kit of embodiment 316, where the plurality of co-activating molecules includes T cell receptor (TCR) co-activating molecules and adjunct TCR activating molecules.

318. The kit of embodiment 317, where a container containing the reagent including the plurality of co-activating molecules contains a ratio of the TCR co-activating molecules to the adjunct TCR activating molecules from about 20:1 to about 1:20.

319. The kit of any one of embodiments 312 to 318, where the TCR co-activating molecules are agonists of a CD28 receptor.

320. The kit of any one of embodiments 312 to 319, where the adjunct TCR activating molecules are agonists of a CD2 receptor.

321. The kit of any one of embodiments 312 to 320, further including a reagent including growth stimulatory molecules, where each growth stimulatory molecule includes a growth factor receptor ligand.

322. The kit of embodiment 321, where the growth factor receptor ligand includes IL-21 or a fragment thereof.

323. The kit of embodiment 321 or 322, further including a second growth stimulatory molecule including IL-7 or IL-2.

324. A kit for preparing a well plate including a surface having an antigen-presenting covalently functionalized region, including a well plate including a surface including an azido-presenting covalently functionalized region; and a first surface functionalization reagent.

325. The kit of embodiment 324, where the well plate including the surface having the azido-presenting covalently functionalized region is the well plate of any one of embodiments 1 to 11, where the reactive moiety is azido, any one of embodiments 31 to 33 where the reactive moiety is azido, or any one of embodiments 122-129.

326. The kit of embodiment 324 or 325, where the first surface functionalization reagent includes a reagent including a biotin moiety linked to a reactive group, where the reactive group is configured to react with the azido moieties of the surface.

327. The kit of embodiment 326, further including a second surface functionalization reagent including streptavidin.

328. The kit of embodiment 326 or 327, where the first functionalization reagent includes a streptavidin moiety linked to a reactive group, where the reactive group is configured to react with azido moieties.

329. The kit of any one of embodiments 324 to 328, further including a surface blocking reagent including a surface blocking moiety linked to a reactive group configured to react with the azido moieties.

330. The kit of embodiment 329, where the surface blocking moiety includes a hydrophilic or negatively charged moiety.

331. The kit of embodiment 329 or 330, where the surface blocking reagent include polyethylene glycol (PEG) moieties.

332. The kit of any one of embodiments 324 to 331, further including a first activating reagent including a plurality of major histocompatibility complex (MHC) molecules (e.g., Class I or Class II) configured to bind with a T cell receptor of the T cell, and further where the MHC molecules are configured to bind to a binding site of streptavidin.

333. The kit of embodiment 332, where each of the plurality of MHC molecules further includes at least one biotin functionality 334. The kit of any one of embodiments 324 to 333, further including a reagent including a plurality of co-activating molecules, each having a binding moiety configured to bind a binding site of streptavidin, and where each of the co-activating molecules includes a T cell receptor (TCR) co-activating molecule or an adjunct TCR activating molecule.

335. The kit of embodiment 334, where the plurality of co-activating molecules includes T cell receptor (TCR) co-activating molecules and adjunct TCR activating molecules.

336. The kit of embodiment 335, where a container containing the reagent including the plurality of co-activating molecules contains a ratio of the TCR co-activating molecules to the adjunct TCR activating molecules from about 20:1 to about 1:20.

337. The kit of any one of embodiments 324 to 336, where the TCR co-activating molecules are agonists of a CD28 receptor.

338. The kit of any one of embodiments 324 to 337, where the adjunct TCR activating molecules are agonists of a CD2 receptor.

339. The kit of any one of embodiments 324 to 338, further including a reagent including growth stimulatory molecules, where each growth stimulatory molecule includes a growth factor receptor ligand.

340. The kit of embodiment 339, where the growth factor receptor ligand includes IL-21 or a fragment thereof.

341. The kit of embodiment 339 or 340, further including a second growth stimulatory molecule including IL-7 or IL-2.

342. A kit for preparing a well plate including a surface having an antigen-presenting covalently functionalized region for antigen-specific activation of a T lymphocyte (T cell) including a well plate including a surface having a streptavidin-presenting covalently functionalized region; and a first activating reagent including a plurality of major histocompatibility complex (MHC) molecules (e.g., Class I or Class II) configured to bind with a T cell receptor of the T cell, and further where the MHC molecules are configured to bind to a binding site of streptavidin.

343. The kit of embodiment 342, where the well plate is the well plate including a surface having a streptavidin-presenting covalently functionalized region of any one of embodiments 1 to 38, where the reactive moiety is streptavidin, or any one of embodiments 141 to 162.

344. The kit of embodiment 343, where each of the plurality of MHC molecules further includes at least one biotin functionality 345. The kit of any one of embodiments 342 to 344, further including a reagent including a plurality of co-activating molecules, each having a binding moiety configured to bind a binding site of streptavidin, and where each of the co-activating molecules includes a T cell receptor (TCR) co-activating molecule or an adjunct TCR activating molecule.

346. The kit of embodiment 345, where the plurality of co-activating molecules includes T cell receptor (TCR) co-activating molecules and adjunct TCR activating molecules.

347. The kit of embodiment 346, where a container containing the reagent including the plurality of co-activating molecules contains a ratio of the TCR co-activating molecules to the adjunct TCR activating molecules from about 20:1 to about 1:20.

348. The kit of any one of embodiments 342 to 347, where the TCR co-activating molecules are agonists of a CD28 receptor.

349. The kit of any one of embodiments 342 to 348, where the adjunct TCR activating molecules are agonists of a CD2 receptor.

350. The kit of any one of embodiments 342 to 349, further including a reagent including growth stimulatory molecules, where each growth stimulatory molecule includes a growth factor receptor ligand.

351. The kit of embodiment 350, where the growth factor receptor ligand includes IL-21 or a fragment thereof.

352. The kit of embodiment 350 or 351, further including a second growth stimulatory molecule including IL-7 or IL-2.

353. A method of treating a subject in need of treating a cancer; including obtaining a plurality of T lymphocytes (T cells) from the subject; contacting the plurality of T cells with a surface of a well plate including an antigen-presenting covalently functionalized region, where the antigen-presenting covalently functionalized region includes a plurality of major histocompatibility complex (MHC) molecules (e.g., Class I or Class II) configured to bind to a T cell receptor of each of the plurality of T cells, where the MHC molecules include an antigen specific for the cancer of the subject; producing a plurality of activated T cells, where the activation is configured to be specific against the cancer of the subject; separating the plurality of specific activated T cells from unactivated cells; and, introducing the plurality of antigen-specific activated T cells into the subject.

354. The method of embodiment 353, where the well plate including the surface having the antigen-presenting covalently functionalized region is the well plate of any one of embodiments 12 to 38, where the lymphocyte activating moiety includes primary and co-activating moieties, or the well plate of any one of embodiments 159 to 182.

355. The method of embodiment 353 or 354, where the well plate including the surface having the antigen-presenting covalently functionalized region is produced by the method of any one of embodiments 242 to 283.

356. A method of treating a subject in need of treating a cancer; including obtaining a plurality of T lymphocytes (T cells) from the subject; producing a plurality of activated T cells by the method of any one of embodiments 38 to 87, where the activation is configured to be specific against the cancer of the subject; separating the plurality of specific activated T cells from unactivated cells; and, introducing the plurality of antigen-specific activated T cells into the subject.

What is claimed:

1. A well plate comprising a surface for presenting an antigen, wherein the surface has a first region which is an activating moiety-presenting covalently functionalized region comprising a plurality of specifically bound primary activating molecular ligands and a plurality of specifically bound co-activating molecular ligands, wherein the first region has an area of 2 mm$^2$ to 35 mm$^2$.

2. The well plate of claim 1, wherein the first region is substantially circular and has a diameter of 2.0 mm to 4.0 mm.

3. The well plate of claim 1, wherein the surface of the well plate further comprises a second region which is a covalently modified region comprising surface blocking ligands, wherein the second region surrounds the first region.

4. The well plate of claim 3, wherein each of the surface blocking ligands comprises a hydrophilic or negatively charged moiety.

5. The well plate of claim 1, wherein the surface of the well plate comprises glass, polystyrene, polypropylene, polycarbonate, polyethylene, cycloolefin copolymer, or melamine.

6. The well plate of claim 1, wherein the first region has a density of activating moieties of at least 50/um$^2$.

7. The well plate of claim 1, wherein the first region comprises the plurality of specifically bound primary activating molecular ligands and the plurality of specifically bound co-activating molecular ligands linked covalently to the surface via a linker having from 5 to 20 backbone atoms, 10 to 40 backbone atoms, or 15 to 50 backbone atoms selected from carbon, silicon, nitrogen, and oxygen.

8. The well plate of claim 1, wherein a ratio of the primary activating molecular ligands to the co-activating molecular ligands on the first region of the surface is 1:5 to 2:1, or 1:2 to 1:1.

9. The well plate of claim 1, wherein each ligand of the plurality of specifically bound primary activating molecular ligands comprises a major histocompatibility complex (WIC) molecule configured to bind to a T cell receptor (TCR) of a T cell.

10. The well plate of claim 9, wherein the WIC molecule comprises an WIC Class I protein sequence and a beta microglobulin protein sequence.

11. The well plate of claim 9, wherein the WIC molecule further comprises an antigenic peptide.

12. The well plate of claim 11, wherein the antigenic peptide is a tumor-associated antigen.

13. The well plate of claim 1, wherein the plurality of specifically bound co-activating molecular ligands comprises T cell receptor (TCR) co-activating molecules and adjunct TCR activating molecules.

14. The well plate of claim 13, wherein a ratio of the TCR co-activating molecules to the adjunct TCR activating molecules of the plurality of specifically bound co-activating molecular ligands is 3:1 to 1:3.

15. The well plate of claim 13, wherein the TCR co-activating molecules comprise a CD28 binding protein, or a fragment thereof which retains binding ability to CD28.

16. The well plate of claim 13, wherein the TCR co-activating molecules comprise a CD80 molecule or a fragment thereof, wherein the fragment retains binding activity to CD28.

17. The well plate of claim 13, wherein the TCR co-activating molecules comprises an anti-CD28 antibody or a fragment thereof, wherein the fragment retains binding activity to CD28.

18. The well plate of claim 13, wherein the adjunct TCR activating molecule comprises a CD2 binding protein, or a fragment thereof which retains binding activity to CD2, and/or a CD58 molecule or fragment thereof, wherein the fragment retains binding activity with CD2.

19. The well plate of claim 13, wherein the adjunct TCR activating molecule includes an anti-CD2 antibody or a fragment thereof, wherein the fragment retains binding activity with CD2.

20. The well plate of claim 1, wherein the plurality of specifically bound primary activating molecular ligands has a density of at least $1\times10^2$ molecules per square micron in the first region; and/or the plurality of specifically bound co-activating molecular ligands has a density of at least $1\times10^2$ molecules per square micron in the first region.

21. A kit for preparing a well plate comprising a surface for presenting an antigen, wherein the surface has an activating moiety-presenting covalently functionalized region, comprising:
a well plate comprising a surface comprising a reactive moiety-presenting covalently functionalized region, wherein the reactive moiety is an azido moiety, an alkynyl moiety, a biotin moiety, or a streptavidin moiety; and
an activating reagent comprising a primary activating reagent and a co-activating reagent,
wherein the reactive moiety-presenting covalently functionalized region has an area of 2 mm$^2$ to 35 mm$^2$.

22. The kit of claim 21, wherein the kit further comprises a surface functionalization reagent, and wherein the surface functionalization reagent is a biotin containing reagent or a streptavidin containing reagent configured to react with the reactive moiety.

23. The kit of claim 21, wherein the primary activating reagent comprises a plurality of major histocompatibility complex (WIC) molecules configured to bind with a T cell receptor of the T cell, and configured to bind to a binding site of streptavidin or a plurality of CD3 binding molecules.

24. The kit of claim 23, wherein the co-activating reagent comprises a plurality of co-activating molecules, each configured to bind a binding site of streptavidin, and wherein each of the co-activating molecules comprises a CD2 binding molecule or a CD28 binding molecule.

25. The kit of claim 21, wherein the surface of the well plate further comprises a surface blocking region, comprising a surface blocking ligand linked to a reactive moiety-presenting covalently functionalized region, wherein the reactive moiety is an azido moiety or an alkynyl moiety.

26. The kit of claim 21, further comprising a surface blocking reagent comprising a surface blocking moiety linked to a reactive group, wherein the reactive group is configured to:
react with an oxide moiety of the surface of the well plate and thereby link the surface blocking moiety with the surface; or
react with the reactive moiety comprising an azido moiety or an alkynyl moiety of the surface of the well plate and thereby couple the surface blocking moiety with the reactive moiety.

27. The kit of claim 26, wherein the surface blocking moiety is a hydrophilic or negatively charged moiety.

* * * * *